US006093795A

United States Patent [19]
Olsen et al.

[11] Patent Number: 6,093,795
[45] Date of Patent: Jul. 25, 2000

[54] ISOLATED HUMAN PRT1 PROTEIN

[75] Inventors: Henrik Steen Olsen, Gaithersburg; Steven Michael Ruben, Olney, both of Md.; Nahum Sonenberg, Cote st. Luc; Nathalie Methot, Hull, both of Canada; Eran Rom, Rehovot, Israel

[73] Assignees: Human Genome Sciences, Inc., Rockville, Md.; McGill University, Quebec, Canada

[21] Appl. No.: 08/990,140

[22] Filed: Dec. 12, 1997

Related U.S. Application Data

[60] Provisional application No. 60/033,151, Dec. 13, 1996.

[51] Int. Cl.[7] .............................. C07K 14/47; C07K 4/12; C07K 7/00
[52] U.S. Cl. ......................... 530/300; 530/324; 530/325; 530/326; 530/327; 530/328; 530/350
[58] Field of Search ..................................... 530/300, 324, 530/325, 326, 350, 327, 328; 514/12

[56] References Cited

U.S. PATENT DOCUMENTS 5,002,874  3/1991  Kaufman ................................ 435/69.1

OTHER PUBLICATIONS

Berendsen, Science, Vo. 282: pp. 642–643, Oct. 1998.
Caldwell, Yakubutsu Dotai (Xenobiotic Metabolism and Disposition), vol. 11(1): pp. 119–125, 1996.
Genbank Report, Imataka, H. et al., Accession No. U73824. (Mar. 1997).
Genbank Report, Yamanaka, S. et al., Accession No. U76111. (Mar. 1997).
Genbank Report, Levy–Strumpf, N. et al., Accession No. X89713. (Mar. 1997).
Genbank Report, Méthot, N. et al., Accession No. U62583. (Jan. 1997).
Genbank Report, Chaudhuri, J. et al., Accession No. U78525. (Feb. 1997).
Imataka, H. et al., "A new translational regulator with homology to eukaryotic translation initiation factor 4G," *EMBO J.* 16:817–825 (Feb. 1997).
Levy–Strumpf, N. et al., "DAP–5, a Novel Homolog of Eukaryotic Translation Initiation Factor 4G Isolated as a Putative Modulator of Gamma Interferon–Induced Programmed Cell Death," *Mol. Cell. Biol.* 17:1615–1625 (Mar. 1997).
Shaughnessy Jr., J.D. et al., "cDNA Cloning, Expression Analysis, and Chromosomal Localization of a Gene with High Homology to Wheat eIF–(iso)4F and Mammalian eIF–4G," *Genomics* 39:192–197 (Jan. 1997).
Yamanaka, S. et al., "A novel translational repressor mRNA is edited extensively in livers containing tumors caused by the transgene expression of the apoB mRNA–editing enzyme," *Genes & Develop.* 11:321–333 (Feb. 1997).
Abramson, R. et al., "Initiation Factors That Bind mRNA, A Comparison of Mammalian Factors With Wheat Germ Factors," *J. Biol. Chem* 263(11):5462–5467 (1988).

Acland, P. et al., "Subcellular fate of the Int–2 oncoprotein is determined by choice of initiation codon," *Nature* 343(6259):662–665 (1990).
Adams, M. et al., "Initial assessment of human gene diversity and expression patterns based upon 83 million nucleotides of cDNA sequence," *Nature* 377(6547 Suppl):3–174 (Sep. 1995).
Allen, M. et al., "Isolation and Sequence of the cDNAs Encoding the Subunits of the Isozyme Form of Wheat Protein Synthesis Initiation Factor 4F," *J. Biol. Chem.* 267(32):23232–23236 (1992).
Beauparlant, P. et al., "The Role of the C–terminal Domain of IκBα in Protein Degradation and Stabilization," *J. Biol. Chem.* 271(18):10690–10696 (May 1996).
Behlke, J. et al., "Structure of initiation factor eIF–3 from rat liver, Hydrodynamic and electron microscopic investigations," *Eur. J. Biochem.* 157(3):523–530 (1986).
Benne, R. and J. Hershey, "Purification and characterization of initiation factor IF–E3 from rabbit reticulocytes," *Proc. Natl. Acad. Sci. USA* 73(9):3005–3009 (1976).
Benne, R. et al., "Protein Synthesis Initiation Factors from Rabbit Reticulocytes: Purification, Characterization, and Radiochemical Labeling," *Meth. Enzymology* 60:15–35 (1979).
Beretta, L. et al., "Rapamycin blocks the phosphorylation of 4E–BP1 and inhibits cap–dependent initiation of translation," *EMBO J.* 15(3):658–664 (Feb. 1996).
Birney, E. et al., "Analysis of the RNA–recognition motif and RS and RGG domains: conservation in metazoan pre–mRNA splicing factors," *Nucleic Acids Research* 21(25):5803–5816 (1993).
Blanar, M. and W. Rutter, "Interaction Cloning: Identification of a Helix–Loop–Helix Zipper Protein That Interacts with c–Fos," *Science* 256:1014–1018 (1992).
Boeck, R. and D. Kolakofsky, "Positions +5 and +6 can be major determinants of the efficiency of non–AUG initiation codons for protein synthesis," *EMBO J.* 13(15):3608–3617 (1994).
Browning, K. et al., "Determination of the Amounts of the Protein Synthesis Initiation and Elongation Factors in Wheat Germ," *J. Biol. Chem.* 265(29):17967–17973 (1990).

(List continued on next page.)

*Primary Examiner*—Terry McKelvey
*Attorney, Agent, or Firm*—Sterne, Kessler, Goldstein & Fox, P.L.L.C.

[57] ABSTRACT

The present invention relates to novel human Prt1 (hPrt1) and eIF4G-like (p97) proteins which are involved in eukaryotic transcription. In particular, isolated nucleic acid molecules are provided encoding the human hPrt1 and p97 proteins. hPrt1 and p97 polypeptides are also provided, as are vectors, host cells and recombinant methods for producing the same. The invention further relates to screening methods for identifying agonists and antagonists of hPrt1 and p97 activity. Also provided are therapeutic methods for treating disease states associated with the hPrt1 and p97 proteins.

151 Claims, 9 Drawing Sheets

OTHER PUBLICATIONS

Brown–Luedi, M. et al., "Protein Synthesis Initiation Factors from Human HeLa Cells and Rabbit Reticulocytes Are Similar: Comparison of Protein Structure, Activities, and Immunochemical Properties," *Biochem.* 21(18):4202–4206 (1982).

Bruening, W. and J. Pelletier, "A Non–AUG Translational Initiation Event Generates Novel WT1 Isoforms," *J. Biol. Chem.* 271(15):8646–8654 (Apr. 1996).

Bugler, B. et al., "Alternative Initiation of Translation Determines Cytoplasmic or Nuclear Localization of Basic Fibroblast Growth Factor," *Mol. Cellular Biol.* 11(1):573–577 (1991).

Burd, C. and G. Dreyfuss, "Conserved Structures and Diversity of Functions of RNA–Binding Proteins," *Science* 266:615–621 (1994).

Chambers, J. et al., "Genomic Structure and Amino Acid Sequence Domains of the Human La Autoantigen," *J. Biol. Chem.* 263(34):18043–18051 (1988).

Charest, A. et al., "Murine protein tyrosine phosphatase–P-EST, a stable cytosolic protein tyrosine phosphatase," *Biochem. J.* 308(Pt 2):425–432 (Jun. 1995).

Chaudhuri, J., "Role of Protein Factors In Initiation Of Translation In Eukaryotic Cells," *Dissertation Abstracts International* 58(5B):2266 No. AAR9717861 (Dec. 1996).

Chaudhuri, J., "Biochemical Characterization of Mammalian Translation Initiation Factor 3 (eIF3)," *J. Biol. Chem.* 272(49):30975–30983 (Dec. 1997).

Danaie, P. et al., "Isolation of a Protein Complex Containing Translation Initiation Factor Prt1 from *Saccharomyces cerevisiae*," *J. Biol. Chem.* 270(9):4288–4292 (Mar. 1995).

Duncan, R. et al., "Regulated Phosphorylation and Low Abundance of HeLa Cells Initiation Factor eIF–4F Suggest a Role in Translational Control," *J. Biol. Chem.* 262(1):380–388 (1987).

Evans, D. et al., "Mutational Analysis of the Prt1 Protein Subunit of Yeast Translation Initiation Factor 3," *Mol. Cellular Biol.* 15(8):4525–4535 (Aug. 1995).

Feinberg, B. et al., "Analysis of Temperature–sensitive Mutant ts 187 of *Saccharomyces cerevisiae* Altered in a Component Required for the Initiation of Protein Synthesis," *J. Biol. Chem.* 257(18):10846–10851 (1982).

Florkiewicz, R. and A. Sommer, "Human basic fibroblast growth factor gene encodes four polypeptides: Three initiate translation from non–AUG codons," *Proc. Natl. Acad. Sci. USA* 86(11):3978–3981 (1989).

Garcia–Barrio, M. et al., "GCD10, a translational repressor of GCN4, is the RNA–binding subunit of eukaryotic translation initiation factor–3," *Genes and Development* 9(14):1781–1796 (Jul. 1995).

Gorman, C. et al., "Recombinant Genomes Which Express Chloramphenicol Acetyltransferase in Mammalian Cells," *Mol. Cellular Biol.* 2(9):1044–1051 (1982).

Goumans, H. et al., "The Role of eIF–4C in Protein Synthesis Initiation Complex Fromation," *Biochimica et Biophysica Acta* 608(1):39–46 (1980).

Goyer, C. et al., "TIF4631 and TIF4632: Two Yeast Genes Encoding the High–Molecular–Weight Subunits of the Cap–Binding Protein Complex(Eukaryotic Initiation Factor 4F) Contain an RNA Recognition Motif–Like Sequence and Carry Out an Essential Function," *Mol. Cellular Biol.* 13(8):4860–4874 (1993).

Grünert, S. and R. Jackson, "The immediate downstream codon strongly influences the efficiency of utilization of eukaryotic translation initiation codons," *EMBO J.* 13(15):3618–3630 (1994).

Haghighat, A. et al., "Repression of cap–dependent translation by 4E–binding protein 1: competition with p220 for binding to eukaryotic initiation factor–4E," *EMBO J.* 14(22):5701–5709 (Nov. 1995).

Hanic–Joyce, P. et al., "Molecular Characterization of the Yeast PRT1 Gene in Which Mutations Affect Translation Initiation and Regulation of Cell Proliferation," *J. Biol. Chem.* 262(6):2845–2851 (1987).

Hannig, E., "Protein synthesis in eukaryotic organisms: new insights into the function of translation initiation factor eIF–3," *BioEssays* 17(11):915–919 (Nov. 1995).

Hann, S. et al., "A Non–AUG Translational Initiation in c–myc Exon 1 Generates an N–terminally Distinct Protein Whose Synthesis Is Disrupted in Burkitt's Lymphomas," *Cell* 52(2):185–195 (1988).

Hann, S. et al., "Translational activation of the non–AUG–initiated c–myc 1 protein at high cell densities due to methionine deprivation," *Genes and Development* 6(7):1229–1240 (1992).

Hartwell, L. and C. McLaughlin, "Temperature–sensitive Mutants of Yeast Exhibiting a Rapid Inhibition of Protein Synthesis," *J. Bacteriology* 96(5):1664–1671 (1968).

Hartwell, L. and C. McLaughlin, "A Mutant of Yeast Apparently Defective in the Initiation of Protein Synthesis," *Proc. Natl. Acad. Sci. USA* 62(2):468–474 (1969).

Imataka, H. et al., "Two regulatory proteins that bind to the basic transcription element (BTE), a GC box sequence in the promoter region of the rat P–4501A1 gene," *EMBO J.* 11(10):3663–3671 (1992).

Kevil, C. et al., "Translational enhancement of FGF–2 by eIF–4 factors, and alternate utilization of CUG and AUG codons for translation initiation," *Oncogene* 11(11):2339–2348 (Dec. 1995).

Lamphear, B. et al., "Mapping of Functional Domains in Eukaryotic Protein Synthesis Initiation Factor 4G (eIF4G) with Picornaviral Proteases," *J. Biol. Chem.* 270(37):21975–21983 (Sep. 1995).

Ledda–Columbano, G. et al., "Rapid Induction of Apoptosis in Rat Liver by Cycloheximide," *Am. J. Path.* 140(3):545–549 (1992).

Lin, T. et al., "PHAS–1 as a Link Between Mitogen–Activated Protein Kinase and Translation Initiation," *Science* 266:653–656 (1994).

Mader, S. et al., "The Translation Initiation Factor eIF–4E Binds to a Common Motif Shared by the Translation Factor eIF–4y and the Translational Repressors 4E–Binding Proteins," *Mol. Cellular Biol.* 15(9):4990–4997 (Sep. 1995).

Martin, D. et al., "Inhibitors of Protein Synthesis and RNA Synthesis Prevent Neuronal Death Caused by Nerve Growth Factor Deprivation," *J. Cell Biol.* 106(3):829–844 (1988).

Mehdi, H. et al., "Initiation of translation at CUG, GUG, and ACG codons in mammalian cells," *Gene* 91(2):173–178 (1990).

Mengod, G. and H. Trachsel, "Eukaryotic protein synthesis initiation factor eIF–3: determination of concentration and association with ribosomes in rabbit reticulocyte adn HeLa cell lysates," *Biochimica et Biophysica Acta* 825(2):169–174 (1985).

Merrick, W. and J. Hershey, "The Pathway and Mechanism of Eukaryotic Protein Syntheis," In:Translational Control, Cold Spring Harbor Laboratory Press publ. New York pp. 31–69 (1996).

Méthot, N. et al., "The Translation Initiation Factor eIF–4B Contains an RNA–Binding Region That Is Distinct and Independent from Its Ribonucleoprotein Consensus Sequence," Mol. Cellular Biol. 14(4):2307–2316 (1994).

Méthot, N. et al., "In vitro RNA selection identifies RNA ligands that specifically bind to eukaryotic translation intiation factor 4B: The role of the RNA recognition motif," RNA 2(1):38–50 (Jan. 1996).

Méthot, N. et al., "A Region Rich in Aspartic Acid, Arginine, Tyrosine, and Glycine (DRYG) Mediates Eukaryotic Initiation Factor 4B (eIF4B) Self–Association and Interaction with eIF3," Mol. Cellular Biol. 16(10):5328–5334 (Oct. 1996).

Méthot, N. et al., "The Human Homologue of the Yeast Prt1 Protein Is an Integral Part of the Eukaryotic Initiation Factor 3 Complex and Interacts with p170," J. Biol. Chem. 272(2):1110–1116 (Jan. 1997).

Meyer, L. et al., "Immunochemical Characterization of Mammalian Protein Synthesis Initiation Factors," Biochem. 21(18):4206–4212 (1982).

Milburn, S. et al., "Immunoblot Analysis of the Structure of Protein Synthesis Initiation Factor eIF3 from HeLa Cells," Arch. Biochem. Biophysics 276(1):6–11 (1990).

Nagai, K. et al., "The RNP domain: a sequence–specific RNA–binding domain involved in processing and transport of RNA," TIBS 20:235–240 (Jun. 1995).

Naranda, T. et al., "Purified Yeast Translational Initiation Factor eIF–3 Is an RNA–binding Protein Complex that Contains the PRT1 Protein," J. Biol. Chem. 269(51):32286–32292 (1994).

Nygård, O. and P. Westermann, "Specific interaction of one subunit of eukaryotic initiation factor eIF–3 with 18S ribosomal RNA within the binary complex, eIF–3 small ribosomal subunit, as shown by cross–linking experiments," Nucleic Acids Research 10(4):1327–1334 (1982).

Ohlmann, T. et al., "The C–terminal domain of eukaryotic protein synthesis initiation factor (eIF) 4G is sufficient to support cap–independent translation in the absence of eIF4E," EMBO J. 15(6):1371–1382 (Mar. 1996).

Pain, V., "Initiation of protein synthesis in eukaryotic cells," Eur. J. Biochem. 236(3):747–771 (Mar. 1996).

Pause, A. et al., "Insulin–dependent stimulation of protein synthesis by phosphorylation of a regulator of 5'–cap function," Nature 371(6500):762–767 (1994).

Peterson, D. et al., "Binding and Release of Radiolabeled Eukaryotic Initiation Factors 2 and 3 during 80S Initiation Complex Formation," J. Biol. Chem. 254(7):2509–2516 (1979).

Polunovsky, V. et al., "Induction of Endothelial Cell Apoptosis by TNFα: Modulation by Inhibitors of Protein Synthesis," Exper. Cell Res. 214(2):584–594 (1994).

Rau, M. et al., "A Reevaluation of the Cap–binding Protein, eIF4E, as a Rate–limiting Factor for Initiation of Translation in Retculocyte Lysate," J. Biol. Chem. 271(15):8983–8990 (Apr. 1996).

Rozen, F. et al., "Bidirectional RNA Helicase Activity of Eucaryotic Translation Initiation Factors 4A and 4F," Mol. Cellular Biol. 10(3):1134–1144 (1990).

Scherly, D. et al., "Major determinants of the specificity of interaction between small nuclear ribonucleoproteins U1A and U2B$^{ll}$ and their cognate RNAs," Nature 345(6275):502–506 (1990).

Scherly, D. et al., "The U2B$^{ll}$ RNP motif as a site of protein–protein interaction," EMBO J. 9(11):3675–3681 (1990).

Schreier, M. et al., "Initiation of Mammalian Protein Synthesis, I. Purification and Characterization of Seven Initiation Factors," J. Mol. Biol. 116(4):727–753 (1977).

Shockett, P. et al., "A modified tetracycline–regulated system provides autoregulatory, inducible gene expression in cultured cells and transgenic mice," Proc. Natl. Acad. Sci. USA 92(14):6522–6526 (Jul. 1995).

Trachsel, H. et al., "Initiation of Mammalian Protein Synthesis, II. The Assembly of the Initiation Complex with Purified Initiation Factors," J. Mol. Biol. 116(4):755–767 (1977).

Westermann, P. and O. Nygård, "Cross–linking of mRNA to initiation factor eIF–3, 24 kDa cap binding protein and ribosomal proteins S1, S3/3a, S6 and S11 within the 48S pre–initiation complex," Nucleic Acids Research 12(23):8887–8897 (1984).

Yan, R. et al., "Amino Acid Sequence of the Human Protein Synthesis Initiation Factor eIF–4$_γ$," J. Biol. Chem. 267(32): 23226–23231 (1992).

Méthot, N. et al., "A Region Rich in Aspartic Acid, Arginine, Tyrosine, and Glycine (DRYG) Mediates Eukaryotic Initiation Factor 4B (eIF4B) Self–Association and Interaction with eIF3," Chem. Abstracts 125(21):427, Abstract No. 268332 (Nov. 1996).

Figure 1A

```
      ccctcgagtcgacggtatcgataagcttatcgataccgtcgactgctaccgaaggccggc
  1   ---------+---------+---------+---------+---------+---------+    60
      ggccgcggagccctgcgagtaggcagcgttgggcccatgcaggacgcggagaacgtggcg
 61   ---------+---------+---------+---------+---------+---------+   120
                                       MetGlnAspAlaGluAsnValAla
                                        M  Q  D  A  E  N  V  A
      gtgcccgaggcggccgaggagcgcgccgagcccggccagcagcagccggccgccgagccg
121   ---------+---------+---------+---------+---------+---------+   180
      ValProGluAlaAlaGluGluArgAlaGluProGlyGlnGlnGlnProAlaAlaGluPro
       V  P  E  A  A  E  E  R  A  E  P  G  Q  Q  Q  P  A  A  E  P
      ccgccagccgaggggctgctgcggcccgcggggcccggcgctccggaggccgcggggacc
181   ---------+---------+---------+---------+---------+---------+   240
      ProProAlaGluGlyLeuLeuArgProAlaGlyProGlyAlaProGluAlaAlaGlyThr
       P  P  A  E  G  L  L  R  P  A  G  P  G  A  P  E  A  A  G  T
      gaggcctccagtgaggaggtggggatcgcggaggccgggccggagcccgaggtgaggacc
241   ---------+---------+---------+---------+---------+---------+   300
      GluAlaSerSerGluGluValGlyIleAlaGluAlaGlyProGluProGluValArgThr
       E  A  S  S  E  E  V  G  I  A  E  A  G  P  E  P  E  V  R  T
      gagccggcggccgaggcagaggcggcctccggcccgtccgagtcgccctcgccgccggcc
301   ---------+---------+---------+---------+---------+---------+   360
      GluProAlaAlaGluAlaGluAlaAlaSerGlyProSerGluSerProSerProProAla
       E  P  A  A  E  A  E  A  A  S  G  P  S  E  S  P  S  P  P  A
      gccgaggagctgcccgggtcgcatgctgagccccctgtcccggcacagggcgaggcccca
361   ---------+---------+---------+---------+---------+---------+   420
      AlaGluGluLeuProGlySerHisAlaGluProProValProAlaGlnGlyGluAlaPro
       A  E  E  L  P  G  S  H  A  E  P  P  V  P  A  Q  G  E  A  P
      ggagagcaggctcgggacgcaggctccgacagccgggcccaggcggtgtccgaggacgcg
421   ---------+---------+---------+---------+---------+---------+   480
      GlyGluGlnAlaArgAspAlaGlySerAspSerArgAlaGlnAlaValSerGluAspAla
       G  E  Q  A  R  D  A  G  S  D  S  R  A  Q  A  V  S  E  D  A
      ggaggaaacgagggcagagcggccgaggccgaaccccgggcgctggagaacggcgacgcg
481   ---------+---------+---------+---------+---------+---------+   540
      GlyGlyAsnGluGlyArgAlaAlaGluAlaGluProArgAlaLeuGluAsnGlyAspAla
       G  G  N  E  G  R  A  A  E  A  E  P  R  A  L  E  N  G  D  A
      gacgagccctccttcagcgaccccgaggacttcgtggacgacgtgagcgaggaagaatta
541   ---------+---------+---------+---------+---------+---------+   600
      AspGluProSerPheSerAspProGluAspPheValAspAspValSerGluGluGluLeu
       D  E  P  S  F  S  D  P  E  D  F  V  D  D  V  S  E  E  E  L
      ctggagatgtactcaaagatcggccccaggaagcagatggaatcgattcggtgattgta
601   ---------+---------+---------+---------+---------+---------+   660
      LeuGlyAspValLeuLysAspArgProGlnGluAlaAspGlyIleAspSerValIleVal
       L  G  D  V  L  K  D  R  P  Q  E  A  D  G  I  D  S  V  I  V
      gtggacaatgtccctcaggtgggacccgaccgacttgagaaactcaaaaatgtcatccac
661   ---------+---------+---------+---------+---------+---------+   720
      ValAspAsnValProGlnValGlyProAspArgLeuGluLysLeuLysAsnValIleHis
       V  D  N  V  P  Q  V  G  P  D  R  L  E  K  L  K  N  V  I  H
      aagatcttttccaagtttgggaaaatcacaaatgatttttatcctgaagaggatgggaag
721   ---------+---------+---------+---------+---------+---------+   780
      LysIlePheSerLysPheGlyLysIleThrAsnAspPheTyrProGluGluAspGlyLys
       K  I  F  S  K  F  G  K  I  T  N  D  F  Y  P  E  E  D  G  K
      acaaaagggtatattttcctggagtacgcgtcccctgcccacgctgtggatgctgtgaag
781   ---------+---------+---------+---------+---------+---------+   840
      ThrLysGlyTyrIlePheLeuGluTyrAlaSerProAlaHisAlaValAspAlaValLys
       T  K  G  Y  I  F  L  E  Y  A  S  P  A  H  A  V  D  A  V  K
      aacgccgacggctacaagcttgacaagcagcacacattccgggtcaacctctttacggat
841   ---------+---------+---------+---------+---------+---------+   900
      AsnAlaAspGlyTyrLysLeuAspLysGlnHisThrPheArgValAsnLeuPheThrAsp
       N  A  D  G  Y  K  L  D  K  Q  H  T  F  R  V  N  L  F  T  D
      tttgacaagtatatgacgatcagtgacgagtgggatattccagagaaacagcctttcaaa
901   ---------+---------+---------+---------+---------+---------+   960
      PheAspLysTyrMetThrIleSerAspGluTrpAspIleProGluLysGlnProPheLys
       F  D  K  Y  M  T  I  S  D  E  W  D  I  P  E  K  Q  P  F  K
      gacctggggaacttacgttactggcttgaagaggcagaatgcagagatcagtacagtgtg
961   ---------+---------+---------+---------+---------+---------+  1020
```

Figure 1B

```
          AspLeuGlyAsnLeuArgTyrTrpLeuGluGluAlaGluCysArgAspGlnTyrSerVal
           D   L   G   N   L   R   Y   W   L   E   E   A   E   C   R   D   Q   Y   S   V
          attttttgagagtggagaccgcacttccatattctggaatgacgtaaaagaccctgtctca
1021      ---------+---------+---------+---------+---------+---------+  1080
          IlePheGluSerGlyAspArgThrSerIlePheTrpAsnAspValLysAspProValSer
           I   F   E   S   G   D   R   T   S   I   F   W   N   D   V   K   D   P   V   S
          attgaagaaagagcgagatggacagagacgtatgtgcgttggtctcctaagggcacctac
1081      ---------+---------+---------+---------+---------+---------+  1140
          IleGluGluArgAlaArgTrpThrGluThrTyrValArgTrpSerProLysGlyThrTyr
           I   E   E   R   A   R   W   T   E   T   Y   V   R   W   S   P   K   G   T   Y
          ctggctacctttcatcaaagaggcattgctctatggggggagagaaattcaagcaaatt
1141      ---------+---------+---------+---------+---------+---------+  1200
          LeuAlaThrPheHisGlnArgGlyIleAlaLeuTrpGlyGlyGluLysPheLysGlnIle
           L   A   T   F   H   Q   R   G   I   A   L   W   G   G   E   K   F   K   Q   I
          cagagattcagccaccaaggggttcagcttattgacttctccacttgtgaaaggtacctg
1201      ---------+---------+---------+---------+---------+---------+  1260
          GlnArgPheSerHisGlnGlyValGlnLeuIleAspPheSerProCysGluArgTyrLeu
           Q   R   F   S   H   Q   G   V   Q   L   I   D   F   S   P   C   E   R   Y   L
          gtgacctttagcccccctgatggacacgcaggatgaccctcaggccataatcatctgggac
1261      ---------+---------+---------+---------+---------+---------+  1320
          ValThrPheSerProLeuMetAspThrGlnAspAspProGlnAlaIleIleIleTrpAsp
           V   T   F   S   P   L   M   D   T   Q   D   D   P   Q   A   I   I   I   W   D
          atccttacggggcacaagaagagggggttttcactgtgagagctcagcccattggcctatt
1321      ---------+---------+---------+---------+---------+---------+  1380
          IleLeuThrGlyHisLysLysArgGlyPheHisCysGluSerSerAlaHisTrpProIle
           I   L   T   G   H   K   K   R   G   F   H   C   E   S   S   A   H   W   P   I
          tttaagtggagccatgatggcaaattctttgccagaatgaccctggatacgcttagcatc
1381      ---------+---------+---------+---------+---------+---------+  1440
          PheLysTrpSerHisAspGlyLysPhePheAlaArgMetThrLeuAspThrLeuSerIle
           F   K   W   S   H   D   G   K   F   F   A   R   M   T   L   D   T   L   S   I
          tatgaaactccttctatgggtctttggacaagaagagtttgaagatctctgggataaaa
1441      ---------+---------+---------+---------+---------+---------+  1500
          TyrGluThrProSerMetGlyLeuLeuAspLysLysSerLeuLysIleSerGlyIleLys
           Y   E   T   P   S   M   G   L   L   D   K   K   S   L   K   I   S   G   I   K
          gactttcttggtctcctggtggtaacataatcgccttctgggtgcctgaagacaaagat
1501      ---------+---------+---------+---------+---------+---------+  1560
          AspPheSerTrpSerProGlyGlyAsnIleIleAlaPheTrpValProGluAspLysAsp
           D   F   S   W   S   P   G   G   N   I   I   A   F   W   V   P   E   D   K   D
          attccagccagggtaaccctgatgcagctccctaccaggcaagagatccgagtgaggaac
1561      ---------+---------+---------+---------+---------+---------+  1620
          IleProAlaArgValThrLeuMetGlnLeuProThrArgGlnGluIleArgValArgAsn
           I   P   A   R   V   T   L   M   Q   L   P   T   R   Q   E   I   R   V   R   N
          ctgttcaatgtggtggactgcaagctccattggcagaagaacggagactacttgtgtgtg
1621      ---------+---------+---------+---------+---------+---------+  1680
          LeuPheAsnValValAspCysLysLeuHisTrpGlnLysAsnGlyAspTyrLeuCysVal
           L   F   N   V   V   D   C   K   L   H   W   Q   K   N   G   D   Y   L   C   V
          aaagtagataggactccgaaaggcacccagggtgttgtcacaaattttgaaattttccga
1681      ---------+---------+---------+---------+---------+---------+  1740
          LysValAspArgThrProLysGlyThrGlnGlyValValThrAsnPheGluIlePheArg
           K   V   D   R   T   P   K   G   T   Q   G   V   V   T   N   F   E   I   F   R
          atgagggagaaacaggtacctgtggatgtggtcgagatgaaagaaaccatcatagcctt
1741      ---------+---------+---------+---------+---------+---------+  1800
          MetArgGluLysGlnValProValAspValValGluMetLysGluThrIleIleAlaPhe
           M   R   E   K   Q   V   P   V   D   V   V   E   M   K   E   T   I   I   A   F
          gcctgggaaccaaatggaagtaagtttgctgtgctgcacggagaggctccgcggatatct
1801      ---------+---------+---------+---------+---------+---------+  1860
          AlaTrpGluProAsnGlySerLysPheAlaValLeuHisGlyGluAlaProArgIleSer
           A   W   E   P   N   G   S   K   F   A   V   L   H   G   E   A   P   R   I   S
          gtgtctttctaccacgtcaaaaacaacgggaagattgaactcatcaagatgttcgacaag
1861      ---------+---------+---------+---------+---------+---------+  1920
          ValSerPheTyrHisValLysAsnAsnGlyLysIleGluLeuIleLysMetPheAspLys
           V   S   F   Y   H   V   K   N   N   G   K   I   E   L   I   K   M   F   D   K
          cagcaggcgaacaccatcttctggagcccccaaggacagttcgtggtgttggcggcctg
1921      ---------+---------+---------+---------+---------+---------+  1980
```

Figure 1C

```
              GlnGlnAlaAsnThrIlePheTrpSerProGlnGlyGlnPheValValLeuAlaGlyLeu
              Q  Q  A  N  T  I  F  W  S  P  Q  G  Q  F  V  V  L  A  G  L
              aggagtatgaacggtgccttagcgtttgtggacacttcggactgcacggtcatgaacatc
1981          ---------+---------+---------+---------+---------+---------+   2040
              ArgSerMetAsnGlyAlaLeuAlaPheValAspThrSerAspCysThrValMetAsnIle
              R  S  M  N  G  A  L  A  F  V  D  T  S  D  C  T  V  M  N  I
              gcagagcactacatggcttccgacgtcgaatgggatcctactgggcgctacgtcgtcacc
2041          ---------+---------+---------+---------+---------+---------+   2100
              AlaGluHisTyrMetAlaSerAspValGluTrpAspProThrGlyArgTyrValValThr
              A  E  H  Y  M  A  S  D  V  E  W  D  P  T  G  R  Y  V  V  T
              tctgtgtcctggtggagccataaggtggacaacgcgtactggctgtggactttccaggga
2101          ---------+---------+---------+---------+---------+---------+   2160
              SerValSerTrpTrpSerHisLysValAspAsnAlaTyrTrpLeuTrpThrPheGlnGly
              S  V  S  W  W  S  H  K  V  D  N  A  Y  W  L  W  T  F  Q  G
              cgcctcctgcagaagaacaacaaggaccgcttctgccagctgctgtggcggcccggcct
2161          ---------+---------+---------+---------+---------+---------+   2220
              ArgLeuLeuGlnLysAsnAsnLysAspArgPheCysGlnLeuLeuTrpArgProArgPro
              R  L  L  Q  K  N  N  K  D  R  F  C  Q  L  L  W  R  P  R  P
              cccacactcctgagccaggaacagatcaagcaaattaaaaaggatctgaagaaatactct
2221          ---------+---------+---------+---------+---------+---------+   2280
              ProThrLeuLeuSerGlnGluGlnIleLysGlnIleLysLysAspLeuLysLysTyrSer
              P  T  L  L  S  Q  E  Q  I  K  Q  I  K  K  D  L  K  K  Y  S
              aagatctttgaacagaaggatcgtttgagtcagtccaaagcctcaaaggaattggtggag
2281          ---------+---------+---------+---------+---------+---------+   2340
              LysIlePheGluGlnLysAspArgLeuSerGlnSerLysAlaSerLysGluLeuValGlu
              K  I  F  E  Q  K  D  R  L  S  Q  S  K  A  S  K  E  L  V  E
              agaaggcgcaccatgatggaagatttccggaagtaccggaaaatggcccaggagctctat
2341          ---------+---------+---------+---------+---------+---------+   2400
              ArgArgArgThrMetMetGluAspPheArgLysTyrArgLysMetAlaGlnGluLeuTyr
              R  R  R  T  M  M  E  D  F  R  K  Y  R  K  M  A  Q  E  L  Y
              atggagcagaaaaacgagcgcctggagttgcgaggaggggtggacactgacgagctggac
2401          ---------+---------+---------+---------+---------+---------+   2460
              MetGluGlnLysAsnGluArgLeuGluLeuArgGlyGlyValAspThrAspGluLeuAsp
              M  E  Q  K  N  E  R  L  E  L  R  G  G  V  D  T  D  E  L  D
              agcaacgtggacgactgggaagaggagaccattgagttcttcgtcactgaagaaatcatt
2461          ---------+---------+---------+---------+---------+---------+   2520
              SerAsnValAspAspTrpGluGluGluThrIleGluPhePheValThrGluGluIleIle
              S  N  V  D  D  W  E  E  E  T  I  E  F  F  V  T  E  E  I  I
              cccctcggaatcaggagtgacctggagcactgtgcgcagccgtgtgtgctgtggagccga
2521          ---------+---------+---------+---------+---------+---------+   2580
              ProLeuGlyIleArgSerAspLeuGluHisCysAlaGlnProCysValLeuTrpSerArg
              P  L  G  I  R  S  D  L  E  H  C  A  Q  P  C  V  L  W  S  R
              ggccgtcctgcaggaagccgcgtgactcccgcctcctccctgtgctctctggctctggac
2581          ---------+---------+---------+---------+---------+---------+   2640
              GlyArgProAlaGlySerArgValThrProAlaSerSerLeuCysSerLeuAlaLeuAsp
              G  R  P  A  G  S  R  V  T  P  A  S  S  L  C  S  L  A  L  D
              tgtgactgcgcctggattctgccattgcgacacattttgtgcctttcagcccctggtgt
2641          ---------+---------+---------+---------+---------+---------+   2700
              CysAspCysAlaTrpIleLeuProLeuArgHisIlePheValProPheSerProTrpCys
              C  D  C  A  W  I  L  P  L  R  H  I  F  V  P  F  S  P  W  C
              ctgcagtggggatttaaggcacccgcttccacttctttcttgtttggagttttctgttg
2701          ---------+---------+---------+---------+---------+---------+   2760
              LeuGlnTrpGlyIleEnd
              L  Q  W  G  I  * gaaccgccggcgttggctccgaagacttagcgacgcactggcggcaccttctcctgcgcc
2761          ---------+---------+---------+---------+---------+---------+   2820 cagtgatgtttccacggtgcctgtacacagccgagcagcatttccgttgaaggacttgca
2821          ---------+---------+---------+---------+---------+---------+   2880 tcccccattgcgggcagtgctggacgtgtcccggagacccaccggagggcgccgcatgcct
2881          ---------+---------+---------+---------+---------+---------+   2940
```

Figure 1D

```
      tgtacccccaccgtgcaggttgtggccggttttctccgcaggttgaacatggaaataaaa
2941  ---------+---------+---------+---------+---------+---------+  3000 gcaaacttgtatgaaaaaaaaaaaaaaaaaa
3001  ---------+---------+---------+--  3032
```

Figure 2A

```
       cagcagtgagtcggagctctatggaggtggcagcgggtaccgagtggcggctgcagcagc
  1    ---------+---------+---------+---------+---------+---------+    60 gactcctctgagctgagtttgaggccgtccccgactccttcctccccttccctccccct
 61    ---------+---------+---------+---------+---------+---------+   120 ttttttttgttttccgttcccctttcccctcccttccctatccccgacgaccggatcctga
121    ---------+---------+---------+---------+---------+---------+   180 ggaggcagctgcggtggcagctgctgagttctcggtgaaggtatttcatttctcctgtcc
181    ---------+---------+---------+---------+---------+---------+   240 cctcccctccccaccccatctattaatattattcttttgaagattcttcgttgtcaagcc
241    ---------+---------+---------+---------+---------+---------+   300 gccaaagtggagagtgcgattgcagaagggggtgcttctcgtttcagtgcttcttcgggc
301    ---------+---------+---------+---------+---------+---------+   360
              ValGluSerAlaIleAlaGluGlyGlyAlaSerArgPheSerAlaSerSerGly
               V   E   S   A   I   A   E   G   G   A   S   R   F   S   A   S   S   G ggaggaggaagtaggggtgcacctcagcactatcccaagactgctggcaacagcgagttc
361    ---------+---------+---------+---------+---------+---------+   420
       GlyGlyGlySerArgGlyAlaProGlnHisTyrProLysThrAlaGlyAsnSerGluPhe
        G   G   G   S   R   G   A   P   Q   H   Y   P   K   T   A   G   N   S   E   F ctggggaaaaccccagggcaaaacgctcagaaatggattcctgcacgaagcactagacga
421    ---------+---------+---------+---------+---------+---------+   480
       LeuGlyLysThrProGlyGlnAsnAlaGlnLysTrpIleProAlaArgSerThrArgArg
        L   G   K   T   P   G   Q   N   A   Q   K   W   I   P   A   R   S   T   R   R gatgacaactccgcagcaaacaactccgcaaacgaaaaagaacgacatgatgcaatcttc
481    ---------+---------+---------+---------+---------+---------+   540
       AspAspAsnSerAlaAlaAsnAsnSerAlaAsnGluLysGluArgHisAspAlaIlePhe
        D   D   N   S   A   A   N   N   S   A   N   E   K   E   R   H   D   A   I   F aggaaagtaagaggcatactaaataagcttactcctgaaaagtttgacaagctatgcctt
541    ---------+---------+---------+---------+---------+---------+   600
       ArgLysValArgGlyIleLeuAsnLysLeuThrProGluLysPheAspLysLeuCysLeu
        R   K   V   R   G   I   L   N   K   L   T   P   E   K   F   D   K   L   C   L gagctcctcaatgtgggtgtagagtctaaactcatccttaaaggggtcatactgctgatt
601    ---------+---------+---------+---------+---------+---------+   660
       GluLeuLeuAsnValGlyValGluSerLysLeuIleLeuLysGlyValIleLeuLeuIle
        E   L   L   N   V   G   V   E   S   K   L   I   L   K   G   V   I   L   L   I gtggacaaagccctagaagagccaaagtatagctcactgtatgctcagctatgtctgcga
661    ---------+---------+---------+---------+---------+---------+   720
       ValAspLysAlaLeuGluGluProLysTyrSerSerLeuTyrAlaGlnLeuCysLeuArg
        V   D   K   A   L   E   E   P   K   Y   S   S   L   Y   A   Q   L   C   L   R ttggcagaagatgcaccaaactttgatggcccagcagcagagggtcaaccaggacagaag
721    ---------+---------+---------+---------+---------+---------+   780
       LeuAlaGluAspAlaProAsnPheAspGlyProAlaAlaGluGlyGlnProGlyGlnLys
        L   A   E   D   A   P   N   F   D   G   P   A   A   E   G   Q   P   G   Q   K caaagcaccacattcagacgcctcctaatttccaaattacaagatgaatttgaaaaccga
781    ---------+---------+---------+---------+---------+---------+   840
       GlnSerThrThrPheArgArgLeuLeuIleSerLysLeuGlnAspGluPheGluAsnArg
        Q   S   T   T   F   R   R   L   L   I   S   K   L   Q   D   E   F   E   N   R actagaaatgttgatgtctatgataagcgtgaaaatcccctcctccccgaggaggaggaa
841    ---------+---------+---------+---------+---------+---------+   900
       ThrArgAsnValAspValTyrAspLysArgGluAsnProLeuLeuProGluGluGluGlu
```

Figure 2B

```
        T  R  N  V  D  V  Y  D  K  R  E  N  P  L  L  P  E  E  E  E
      cagagagccattgctaagatcaagatgttgggaaacatcaaattcattggagagcttggc
 901  ---------+---------+---------+---------+---------+---------+  960
      GlnArgAlaIleAlaLysIleLysMetLeuGlyAsnIleLysPheIleGlyGluLeuGly
       Q  R  A  I  A  K  I  K  M  L  G  N  I  K  F  I  G  E  L  G aagcttgatcttattcacgaatctatccttcataagtgcatcaaaacacttttggaaaag
 961  ---------+---------+---------+---------+---------+---------+ 1020
      LysLeuAspLeuIleHisGluSerIleLeuHisLysCysIleLysThrLeuLeuGluLys
       K  L  D  L  I  H  E  S  I  L  H  K  C  I  K  T  L  L  E  K aagaagagagtccaactcaaagatatgggagaggatttggagtgcctctgtcagataatg
1021  ---------+---------+---------+---------+---------+---------+ 1080
      LysLysArgValGlnLeuLysAspMetGlyGluAspLeuGluCysLeuCysGlnIleMet
       K  K  R  V  Q  L  K  D  M  G  E  D  L  E  C  L  C  Q  I  M aggacagtgggacctagattagaccatgaacgagccaagtccttaatggatcagtacttt
1081  ---------+---------+---------+---------+---------+---------+ 1140
      ArgThrValGlyProArgLeuAspHisGluArgAlaLysSerLeuMetAspGlnTyrPhe
       R  T  V  G  P  R  L  D  H  E  R  A  K  S  L  M  D  Q  Y  F gcccgaatgtgctccttgatgttaagtaaggaattgccagcaaggattcgtttcctgctg
1141  ---------+---------+---------+---------+---------+---------+ 1200
      AlaArgMetCysSerLeuMetLeuSerLysGluLeuProAlaArgIleArgPheLeuLeu
       A  R  M  C  S  L  M  L  S  K  E  L  P  A  R  I  R  F  L  L caggataccgtagagttgcgagaacaccattgggttcctcgcaaggcttttcttgacaat
1201  ---------+---------+---------+---------+---------+---------+ 1260
      GlnAspThrValGluLeuArgGluHisHisTrpValProArgLysAlaPheLeuAspAsn
       Q  D  T  V  E  L  R  E  H  H  W  V  P  R  K  A  F  L  D  N ggaccaaagacgatcaatcaaattcgtcaagatgcagtaaaagatctagggtgtttatt
1261  ---------+---------+---------+---------+---------+---------+ 1320
      GlyProLysThrIleAsnGlnIleArgGlnAspAlaValLysAspLeuGlyValPheIle
       G  P  K  T  I  N  Q  I  R  Q  D  A  V  K  D  L  G  V  F  I cctgctcctatggctcaagggatgagaagtgacttctttctggagggaccgttcatgcca
1321  ---------+---------+---------+---------+---------+---------+ 1380
      ProAlaProMetAlaGlnGlyMetArgSerAspPhePheLeuGluGlyProPheMetPro
       P  A  P  M  A  Q  G  M  R  S  D  F  F  L  E  G  P  F  M  P cccaggatgaaaatggatagggacccacttggaggacttgctgatatgtttggacaaatg
1381  ---------+---------+---------+---------+---------+---------+ 1440
      ProArgMetLysMetAspArgAspProLeuGlyGlyLeuAlaAspMetPheGlyGlnMet
       P  R  M  K  M  D  R  D  P  L  G  G  L  A  D  M  F  G  Q  M ccaggtagcggaattggtactggtccaggagttatccaggatagattttcacccaccatg
1441  ---------+---------+---------+---------+---------+---------+ 1500
      ProGlySerGlyIleGlyThrGlyProGlyValIleGlnAspArgPheSerProThrMet
       P  G  S  G  I  G  T  G  P  G  V  I  Q  D  R  F  S  P  T  M ggacgtcatcgttcaaatcaactcttcaatggccatggggacacatcatgcctcccaca
1501  ---------+---------+---------+---------+---------+---------+ 1560
      GlyArgHisArgSerAsnGlnLeuPheAsnGlyHisGlyGlyHisIleMetProProThr
       G  R  H  R  S  N  Q  L  F  N  G  H  G  G  H  I  M  P  P  T caatcgcagtttggagagatggggaggcaagtttatgaaaagccaggggctaagccagctc
1561  ---------+---------+---------+---------+---------+---------+ 1620
      GlnSerGlnPheGlyGluMetGlyGlyLysPheMetLysSerGlnGlyLeuSerGlnLeu
       Q  S  Q  F  G  E  M  G  G  K  F  M  K  S  Q  G  L  S  Q  L taccataaccagagtcagggactcttatcccagctgcaaggacagtcgaaggatatgcca
1621  ---------+---------+---------+---------+---------+---------+ 1680
```

Figure 2C

```
            TyrHisAsnGlnSerGlnGlyLeuLeuSerGlnLeuGlnGlyGlnSerLysAspMetPro
             Y   H   N   Q   S   Q   G   L   L   S   Q   L   Q   G   Q   S   K   D   M   P cctcggttttctaagaaaggacagcttaatgcagatgagattagcctgaggcctgctcag
     1681   ---------+---------+---------+---------+---------+---------+   1740
            ProArgPheSerLysLysGlyGlnLeuAsnAlaAspGluIleSerLeuArgProAlaGln
             P   R   F   S   K   K   G   Q   L   N   A   D   E   I   S   L   R   P   A   Q tcgttcctaatgaataaaaatcaagtgccaaagcttcagccccagataactatgattcct
     1741   ---------+---------+---------+---------+---------+---------+   1800
            SerPheLeuMetAsnLysAsnGlnValProLysLeuGlnProGlnIleThrMetIlePro
             S   F   L   M   N   K   N   Q   V   P   K   L   Q   P   Q   I   T   M   I   P cctagtgcacaaccaccacgcactcaaacaccacctctgggacagacacctcagcttggt
     1801   ---------+---------+---------+---------+---------+---------+   1860
            ProSerAlaGlnProProArgThrGlnThrProProLeuGlyGlnThrProGlnLeuGly
             P   S   A   Q   P   P   R   T   Q   T   P   P   L   G   Q   T   P   Q   L   G ctcaaaactaatccaccacttatccaggaaaagcctgccaagaccagcaaaaagccacca
     1861   ---------+---------+---------+---------+---------+---------+   1920
            LeuLysThrAsnProProLeuIleGlnGluLysProAlaLysThrSerLysLysProPro
             L   K   T   N   P   P   L   I   Q   E   K   P   A   K   T   S   K   K   P   P ccgtcaaaggaagaactccttaaactaactgaaactgttgtgactgaatatctaaatagt
     1921   ---------+---------+---------+---------+---------+---------+   1980
            ProSerLysGluGluLeuLeuLysLeuThrGluThrValValThrGluTyrLeuAsnSer
             P   S   K   E   E   L   L   K   L   T   E   T   V   V   T   E   Y   L   N   S ggaaatgcaaatgaggctgtcaatggtgtaagagaaatgagggctcctaaacactttctt
     1981   ---------+---------+---------+---------+---------+---------+   2040
            GlyAsnAlaAsnGluAlaValAsnGlyValArgGluMetArgAlaProLysHisPheLeu
             G   N   A   N   E   A   V   N   G   V   R   E   M   R   A   P   K   H   F   L cctgagatgttaagcaaagtaatcatcctgtcactagatagaagcgatgaagataaagaa
     2041   ---------+---------+---------+---------+---------+---------+   2100
            ProGluMetLeuSerLysValIleIleLeuSerLeuAspArgSerAspGluAspLysGlu
             P   E   M   L   S   K   V   I   I   L   S   L   D   R   S   D   E   D   K   E aaagcaagttctttgatcagtttactcaaacaggaagggatagccacaagtgacaacttc
     2101   ---------+---------+---------+---------+---------+---------+   2160
            LysAlaSerSerLeuIleSerLeuLeuLysGlnGluGlyIleAlaThrSerAspAsnPhe
             K   A   S   S   L   I   S   L   L   K   Q   E   G   I   A   T   S   D   N   F atgcaggctttcctgaatgtattggaccagtgtcccaaactggaggttgacatcccttttg
     2161   ---------+---------+---------+---------+---------+---------+   2220
            MetGlnAlaPheLeuAsnValLeuAspGlnCysProLysLeuGluValAspIleProLeu
             M   Q   A   F   L   N   V   L   D   Q   C   P   K   L   E   V   D   I   P   L gtgaaatcctatttagcacagtttgcagctcgtgccatcatttcagagctggtgagcatt
     2221   ---------+---------+---------+---------+---------+---------+   2280
            ValLysSerTyrLeuAlaGlnPheAlaAlaArgAlaIleIleSerGluLeuValSerIle
             V   K   S   Y   L   A   Q   F   A   A   R   A   I   I   S   E   L   V   S   I tcagaactagctcaaccactagaaagtggcacccatttttcctctcttcctactttgtctt
     2281   ---------+---------+---------+---------+---------+---------+   2340
            SerGluLeuAlaGlnProLeuGluSerGlyThrHisPheProLeuPheLeuLeuCysLeu
             S   E   L   A   Q   P   L   E   S   G   T   H   F   P   L   F   L   L   C   L cagcagttagctaaattacaagatcgagaatggttaacagaacttttcaacaaagcaag
     2341   ---------+---------+---------+---------+---------+---------+   2400
            GlnGlnLeuAlaLysLeuGlnAspArgGluTrpLeuThrGluLeuPheGlnGlnSerLys
             Q   Q   L   A   K   L   Q   D   R   E   W   L   T   E   L   F   Q   Q   S   K gtcaatatgcagaaaatgctcccagaaattgatcagaataaggaccgcatgttggagatt
```

Figure 2D

```
2401    ----------+---------+---------+---------+---------+---------+    2460
        ValAsnMetGlnLysMetLeuProGluIleAspGlnAsnLysAspArgMetLeuGluIle
         V  N  M  Q  K  M  L  P  E  I  D  Q  N  K  D  R  M  L  E  I ttggaaggaaagggactgagtttcttattcccactcctcaaattggagaaggaactgttg
2461    ----------+---------+---------+---------+---------+---------+    2520
        LeuGluGlyLysGlyLeuSerPheLeuPheProLeuLeuLysLeuGluLysGluLeuLeu
         L  E  G  K  G  L  S  F  L  F  P  L  L  K  L  E  K  E  L  L aagcaaataaagttggatccatcccctcaaaccatatataaatggattaaagataacatc
2521    ----------+---------+---------+---------+---------+---------+    2580
        LysGlnIleLysLeuAspProSerProGlnThrIleTyrLysTrpIleLysAspAsnIle
         K  Q  I  K  L  D  P  S  P  Q  T  I  Y  K  W  I  K  D  N  I tctcccaaacttcatgtagataaaggatttgtgaacatcttaatgactagcttcttacag
2581    ----------+---------+---------+---------+---------+---------+    2640
        SerProLysLeuHisValAspLysGlyPheValAsnIleLeuMetThrSerPheLeuGln
         S  P  K  L  H  V  D  K  G  F  V  N  I  L  M  T  S  F  L  Q tacatttctagtgaagtaaacccccccagcgatgaaacagattcatcctctgctccttcc
2641    ----------+---------+---------+---------+---------+---------+    2700
        TyrIleSerSerGluValAsnProProSerAspGluThrAspSerSerSerAlaProSer
         Y  I  S  S  E  V  N  P  P  S  D  E  T  D  S  S  S  A  P  S aaagaacagttagagcaggaaaaacaactactactatctttcaagccagtaatgcagaaa
2701    ----------+---------+---------+---------+---------+---------+    2760
        LysGluGlnLeuGluGlnGluLysGlnLeuLeuLeuSerPheLysProValMetGlnLys
         K  E  Q  L  E  Q  E  K  Q  L  L  L  S  F  K  P  V  M  Q  K tttcttcatgatcacgttgatctacaagtcagtgccctgtatgctctccaggtgcactgc
2761    ----------+---------+---------+---------+---------+---------+    2820
        PheLeuHisAspHisValAspLeuGlnValSerAlaLeuTyrAlaLeuGlnValHisCys
         F  L  H  D  H  V  D  L  Q  V  S  A  L  Y  A  L  Q  V  H  C tataacagcaacttcccaaaaggcatgttacttcgcttttttgtgcacttctatgacatg
2821    ----------+---------+---------+---------+---------+---------+    2880
        TyrAsnSerAsnPheProLysGlyMetLeuLeuArgPhePheValHisPheTyrAspMet
         Y  N  S  N  F  P  K  G  M  L  L  R  F  F  V  H  F  Y  D  M gaaattattgaagaagaagctttcttggcttggaaagaagatataacccaagagtttccg
2881    ----------+---------+---------+---------+---------+---------+    2940
        GluIleIleGluGluGluAlaPheLeuAlaTrpLysGluAspIleThrGlnGluPhePro
         E  I  I  E  E  E  A  F  L  A  W  K  E  D  I  T  Q  E  F  P ggaaaaggcaaggctttgttccaggtgaatcagtggctaacctggttagaaactgctgaa
2941    ----------+---------+---------+---------+---------+---------+    3000
        GlyLysGlyLysAlaLeuPheGlnValAsnGlnTrpLeuThrTrpLeuGluThrAlaGlu
         G  K  G  K  A  L  F  Q  V  N  Q  W  L  T  W  L  E  T  A  E gaagaagaatcagaggaagaagctgactaaagaaccagccaaagccttaaattgtgcaaa
3001    ----------+---------+---------+---------+---------+---------+    3060
        GluGluGluSerGluGluGluAlaAspEnd
         E  E  E  S  E  E  E  A  D  * acatactgttgctatgatgtaactgcatttgacctaaccactgcgaaaattcattccgct
3061    ----------+---------+---------+---------+---------+---------+    3120 gtaatgttttcacaatatttaaagcagaagcacgtcagttaggatttccttctgcataag
3121    ----------+---------+---------+---------+---------+---------+    3180 gttttttttgtagtgtaatgtcttaatcatagtctaccatcaaatatttttaggagtatctt
3181    ----------+---------+---------+---------+---------+---------+    3240 taatgtttagatagtatattagcagcatgcaataattacatcataagttctcaagcagag
```

*Figure 2E*

```
3241      ---------+---------+---------+---------+---------+---------+    3300 gcagtctattgcaaggaccttctttgctgccagttatcataggctgttttaagttagaaa
3301      ---------+---------+---------+---------+---------+---------+    3360 actgaatagcaacactgaatactgtagaaatgcactttgctcagtaatacttgagttgtt
3361      ---------+---------+---------+---------+---------+---------+    3420 gcaatatttgattatccatttggttgttacagaaaaattcttaactgtaattgatggttg
3421      ---------+---------+---------+---------+---------+---------+    3480 ttgccgtaatagtatattgcctgtatttctacctctagtaatgggctttatgtgctagat
3481      ---------+---------+---------+---------+---------+---------+    3540 tttaatatccttgagcctgggcaagtgcacaagtcttttaaaagaaacatggtttactt
3541      ---------+---------+---------+---------+---------+---------+    3600 gcacaaaactgatcagttttgagagatcgttaatgcccttgaagtggtttttgtgggtgt
3601      ---------+---------+---------+---------+---------+---------+    3660 gaaacaaatggtgagaatttgaattggtccctcctattatagtattgaaattaagtctac
3661      ---------+---------+---------+---------+---------+---------+    3720 ttaatttatcaagtcatgttcatgccctgattttatatacttgtatctatcaataaacat
3721      ---------+---------+---------+---------+---------+---------+    3780 tgtgatacttgaaaaaaaaaaaaaaaaaaaaaaaaaaaaa
3781      ---------+---------+---------+---------+    3820
```

ISOLATED HUMAN PRT1 PROTEIN

This application claims the benefit of the filing date of provisional application No. 60/033,151 filed on Dec. 13, 1996, which is herein incorporated by reference.

BACKGROUND OF THE INVENTION

1. Field of the Invention

The present invention relates to novel proteins involved in the initiation of eukaryotic transcription. More specifically, isolated nucleic acid molecules are provided encoding a human Prt1-like subunit protein (hPrt1) and a human eIF4G-like protein (p97). Also provided are hPrt1 and p97 polypeptides, as are vectors, host cells and recombinant methods for producing the same. The invention further relates to screening methods for identifying agonists and antagonists of hPrt1 and p97 activity.

2. Related Art

Eukaryotic protein synthesis requires the participation of translation initiation factors, which assist in the binding of the mRNA to the 40S ribosomal subunit (reviewed in Merrick & Hershey, in *Translational Control*, Hershey et al., eds., Cold Spring Harbour Laboratory Press, (1996), pp. 31–69 and Pain, *Eur. J. Biochem* 236:747–771 (1996)). Ribosome binding is facilitated by the cap structure ($m^7$GpppN, where N is any nucleotide) that is present at the 5' end of all cellular mRNAs (except organellar). Biochemical fractionation studies elucidated the general pathway for translation initiation and led to the characterization of several translation initiation factors (reviewed in Merrick & Hershey supra). It is believed that the mRNA cap structure is initially bound by eukaryotic initiation factor (eIf) 4F, which, in conjunction with eIF4B, melts RNA secondary structure in the 5' untranslated region (UTR) of the mRNA to promote ribosome binding. eIF4F is a more efficient RNA helicase than free eIF4A (Rozen et al., *Mol. Cell. Biol.* 10:1134–1144 (1990)), consistent with the idea that eIF4A recycles through the eIF4F protein complex to function in unwinding (Pause et al., *Nature* 371:762–767 (1994)). The 40S ribosomal subunit, in a complex with eIF3, eIF1A and eIF2-GTP-tRNAimet, binds at or near the cap structure and scans vectorially the 5' UTR in search of the initiator AUG codon (reviewed in Merrick & Hershey, supra).

eIF3 is the largest translation initiation factor, with at least 8 different polypeptide subunits and a total mass of approximately 550 to 700 kDa (Schreier, et al., *J. Mol. Biol.* 116:727–753 (1977); Benne & Hershey, *Proc. Natl. Acad. Sci. USA* 73:3005–3009 (1976); Behlke et al., *Eur. J. Biochem.* 157:523–530 (1986)). In mammals, the apparent molecular masses of the eIF3 subunits are 35, 36, 40, 44, 47, 66, 115 and 170 kDa (Behlke, supra; Meyer, et al., *Biochemistry* 21:4206–4212 (1982); Milburn et al., *Arch. Biochem. Biophys* 276:6–11 (1990)). eIF3 is a moderately abundant translation initiation factor, with 0.5 to 1 molecule per ribosome in HeLa cells and rabbit reticulocyte lysates (Meyer, supra; Mengod & Trachsel, *Biochem. Acta* 825:169–174 (1985)). This protein complex assumes several functions during translation initiation (reviewed in Hannig, *BioEssays* 17:915–919 (1995)). eIF3 binds to the 40S ribosomal subunit and prevents joining with the 60S subunit. It interacts with the ternary complex and stabilizes the binding of the latter to the 40S ribosomal subunit (Trachsel et al., *J. Mol. Biol.* 116:755–767 (1977); Gupta et al., (1990); Goumans et al., *Biochem. Biophys. Acta* 608:39–46 (1980); Peterson et al., *J. Biol. Chem.* 254:2509–2510 (1979)). eIF3 crosslinks to mRNA and 18S rRNA (Nygard & Westermann, *Nucl. Acids Res.* 10:1327–1334 (1982); Westermann & Nygard, *Nucl. Acids Res.* 12:8887–8897 (1984)), an activity mainly attributed to the 66 kDa subunit (or 62 kDa in yeast; Garcia-Barrio, et al., *Genes Dev.* 9:1781–1796 (1995); Naranda, et al., *J. Biol. Chem.* 269:32286–32292 (1994)). eIF3 co-purifies with eIF4F and eIF4B, two initiation factors involved in the mRNA binding step (Schreier et al., *J. Mol. Biol.* 116:727–753 (1977)). A direct interaction between the 220 kDa subunit of eIF4F and eIF3 has been demonstrated (Lamphear et al., *J. Biol. Chem.* 270:21975–21983 (1995)) and a role for eIF3 serving as a bridge between the 40S ribosomal subunit and eIF4F-bound mRNA has been postulated (Lamphear, supra).

The complex structure of eIF3 and its pleiotropic roles in translation initiation have rendered the study of this factor difficult. The protein sequence for only three of the yeast subunits (SUI1/p16, p62 and PRT1/p90) have been published (Garcia-Barrio et al., *Genes Dev.* 9:1781–1796 (1995); Naranda, supra; Hanic-Joyce et al., *J. Biol. Chem.* 262:2845–2851 (1987)). However, several other mammalian and yeast subunits have been recently cloned. The yeast protein p90, also known as Prt1, is the most well characterized of those identified to date. Prt1 is an integral subunit of eIF3 (Naranda, supra; Danaie et al., *J. Biol. Chem.* 270:4288–4292 (1995)). A conditional lethal mutation in the PRT1 gene reduces the binding of the ternary to the 40S ribosomal subunit (Feinberg et al., *J. Biol. Chem.* 257:10846–10851 (1982)). Other mutations which confer temperature sensitivity are located in the central and carboxy-terminal portion of Prt1. An N-terminal deletion which removes the Prt1 putative RNA Recognition Motif (RRM; for reviews see Birney, et al., *Nucl. Acids Res.* 21:5803–5816 (1993); Burd & Dreyfuss, *Science* 265:615–621 (1994b); Nagai et al., *Trends Biochem. Sci.* 20:235–240 (1995)), acts a trans-dominant negative inhibitor (Evans et al., *Mol. Cell. Biol.* 15:4525–4535 (1995)).

Proteins that specifically inhibit cap-dependent translation have been described (Pause, supra; Lin et al., *Science* 266:653–656 (1994)): 4E-binding protein-1 and -2 (4E-BP1 and 4E-BP2) bind to eIF4E and prevent their association with eIF4G, because 4E-BPs and eIF4G share a common site for eIF4E binding (Haghighat et al., *EMBO J.* 14:5701–5709 (1995); Mader et al., *Mol. Cell. Biol.* 15:4990–4997 (1995)). Upon treatment of cells with insulin and growth factors, 4E-BPs become phosphorylated. This leads to dissociation of the 4E-BPs from eIF4E and formation of the eIF4F complex, which results in stimulation of translation (Pause, supra; Lin, supra; Beretta, et al., *EMBO J.* 15:658–664 (1996)).

SUMMARY OF THE INVENTION

The present invention provides isolated nucleic acid molecules comprising polynucleotides encoding the hPrt1 and p97 polypeptides having the amino acid sequences shown in FIGS. 1A–1D (SEQ ID NO:2) and FIGS. 2A–2E (SEQ ID NO:4) or the amino acid sequences encoded by the cDNA clones deposited as ATCC Deposit Number 97766 on Oct. 18, 1996 and ATCC Deposit Number 97767 on Oct. 18, 1996.

The present invention also relates to recombinant vectors, which include the isolated nucleic acid molecules of the present invention, and to host cells containing the recombinant vectors, as well as to methods of making such vectors and host cells and for using them for production of hPrt1 and p97 polypeptides or peptides by recombinant techniques.

The invention further provides isolated hPrt1 and p97 polypeptides having amino acid sequences encoded by polynucleotides described herein.

The present invention also provides a screening method for identifying compounds capable of enhancing or inhibiting a cellular response induced by hPrt1 and/or p97 polypeptides, which involves contacting cells which express hPrt1 and/or p97 polypeptides with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

Additional aspects of the invention relate to methods for treating an individual in need of either an increased or decreased level of hPrt1 and/or p97 activity in the body comprising administering to such an individual a composition comprising a therapeutically effective amount of either an isolated hPrt1 and/or p97 polypeptides of the invention (or an agonist thereof) or an hPrt1 and/or p97 antagonist.

The present invention also provides components for use in in vitro translation systems. Two individual components of such translation systems, hPrt1 and p97, are provided herein.

BRIEF DESCRIPTION OF THE FIGURES

FIGS. 1A–1D show the nucleotide (SEQ ID NO:1) and deduced amino acid (SEQ ID NO:2) sequence of the hPrt1 polypeptide. The protein has a molecular weight of about 116 kDa, as shown in Example 1. The standard one-letter abbreviations for amino acids are used.

FIGS. 2A–2E show the nucleotide (SEQ ID NO:3) and deduced amino acid (SEQ ID NO:4) sequence of the p97 polypeptide. The protein has a molecular weight of about 97 kDa, as shown in Example 2. Abbreviations are as in FIGS. 1A–1D.

DETAILED DESCRIPTION OF THE INVENTION

The present invention provides isolated nucleic acid molecules comprising a polynucleotide encoding an hPrt1 polypeptide having the amino acid sequence shown in FIGS. 1A–1D (SEQ ID NO:2). The hPrt1 protein of the present invention shares sequence homology with the Prt1 protein of Saccharomyces cerevisiae. The nucleotide sequence shown in FIGS. 1A–1D (SEQ ID NO:1) was obtained by sequencing a cDNA clone, which was deposited on Oct. 18, 1996 at the American Type Culture Collection, 10801 University Blvd., Manassas, Va. 20110-2209, USA, and given accession number 97766. The deposited clone is contained in the pbluescript SK(−) plasmid (Stratagene, LaJolla, Calif.).

In addition, the present invention also provides isolated nucleic acid molecules comprising a polynucleotide encoding an p97 polypeptide having the amino acid sequence shown in FIGS. 2A–2E (SEQ ID NO:4). The p97 protein of the present invention shares sequence homology with the human eIF4G protein. The nucleotide sequence shown in FIGS. 2A–2E (SEQ ID NO:3) was obtained by sequencing a cDNA clone, which was deposited on Oct. 18, 1996 at the American Type Culture Collection, 10801 University Blvd., Manassas, Va. 20110-2209, USA, and given accession number 97767. The deposited clone is contained in the pcDNAIII plasmid (Invitrogen, Inc.).

Nucleic Acid Molecules

Using the information provided herein, such as the nucleotide sequence in FIGS. 1A–1D (SEQ ID NO:1), nucleic acid molecules of the present invention encoding the hPrt1 polypeptide may be obtained using standard cloning and screening procedures, such as those for cloning cDNAs using mRNA as starting material. While the hPRT1 gene was found to be present in cDNA libraries produced from RNA from multiple tissues, the nucleic acid molecule described in FIGS. 1A–1D (SEQ ID NO:1) was isolated from a cDNA library derived from human bone marrow cells. The determined nucleotide sequence of the hPrt1 cDNA of FIGS. 1A–1D (SEQ ID NO:1) contains an open reading frame encoding a protein of 873 amino acid residues, with an initiation codon at positions 97–99 of the nucleotide sequence in FIGS. 1A–1D (SEQ ID NO:1) and a molecular weight of about 116 kDa, as shown in Example 1. The hPrt1 protein shown in FIGS. 1A–1D (SEQ ID NO:2) is about 31% identical and about 50% similar to the Prt1 protein of Saccharomyces cerevisiae (GenBank Accession No. J02674).

In addition, using the information provided herein, such as the nucleotide sequence in FIGS. 2A–2E (SEQ ID NO:3), a nucleic acid molecule of the present invention encoding a p97 polypeptide may also be obtained using standard cloning and screening procedures. While the p97 gene was identified in cDNA libraries produced from RNA from several tissues, the nucleic acid molecule described in FIGS. 2A–2E (SEQ ID NO:3) was isolated from a cDNA library derived from human fetal heart. The determined nucleotide sequence of the p97 cDNA of FIGS. 2A–2E (SEQ ID NO:3) contains an open reading frame encoding a protein of 907 amino acid residues, with an initiation codon at positions 307–309 of the nucleotide sequence in FIGS. 2A–2E (SEQ ID NO:3) and a molecular weight of about 97 kDa, as shown in Example 2. The p97 protein shown in FIGS. 2A–2E (SEQ ID NO:4) is about 28% identical and about 36% similar to approximately the C-terminal two thirds of eIF4G (GenBank Accession No. D12686). The N-terminal third of eIF4G bears no similarity to the p97 protein of the present invention.

As one of ordinary skill would appreciate, due to the possibilities of sequencing errors discussed above the actual hPrt1 polypeptide encoded by the deposited cDNA comprises about 873 amino acids, but may be anywhere in the range of about 850 to about 896 amino acids. Similarly, the actual p97 polypeptide encoded by the deposited cDNA comprises about 907 amino acids, but may be anywhere in the range of about 882 to about 932 amino acids.

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules further includes such molecules produced synthetically.

Isolated nucleic acid molecules of the present invention include DNA molecules comprising open reading frames (ORF) with initiation codons at positions 97–99 of the nucleotide sequence shown in FIGS. 1A–1D (SEQ ID NO:1) for hPrt1 and positions 307–309 of the nucleotide sequence shown in FIGS. 2A–2E (SEQ ID NO:3) for p97; and DNA molecules which comprise a sequence substantially different from those described above but which, due to the degeneracy of the genetic code, still encode either the hPrt1 or p97 proteins.

In another aspect, the invention provides isolated nucleic acid molecules encoding the hPrt1 and p97 polypeptides having amino acid sequences encoded by the cDNA clones contained in the plasmids deposited as ATCC Deposit No. 97766 on Oct. 18, 1996 and ATCC Deposit No. 97767 on Oct. 18, 1996, respectively. The invention further provides isolated nucleic acid molecules having the nucleotide sequences shown in FIGS. 1A–1D (SEQ ID NO:1), FIGS. 2A–2E (SEQ ID NO:3), the nucleotide sequence of the hPrt1 and p97 cDNA contained in the above-described deposited clones, or a nucleic acid molecule having a sequence complementary to any one of the above sequences. In a further embodiment, isolated nucleic acid molecules are provided encoding the full-length hPrt1 and p97 polypeptides lacking the N-terminal amino acid residue.

The present invention is further directed to fragments of the isolated nucleic acid molecules described herein. By a fragment of an isolated nucleic acid molecule having the nucleotide sequences of the deposited cDNAs or the nucleotide sequences shown in FIGS. 1A–1D (SEQ ID NO:1) or FIGS. 2A–2E (SEQ ID NO:3) is intended fragments at least about 15 nt, and more preferably at least about 20 nt, still more preferably at least about 30 nt, and even more preferably, at least about 40 nt in length which are useful as diagnostic probes and primers as discussed herein. Of course larger DNA fragments 50, 100, 150, 200, 250, 300, 350, 400, 450, 500, 550, 600, 650, 700, 750, 800, 850, 900, 100,1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, or 3010 nt in length of the sequence shown in SEQ ID NO:1 are also useful according to the present invention as are fragments corresponding to most, if not all, of the nucleotide sequence of the cDNA clone contained in the plasmid deposited as ATCC Deposit No. 97766 or as shown in SEQ ID NO:1. Similarly, larger DNA fragments 50, 100, 150, 200, 250, 300, 350, 400, 450, 500, 550, 600, 650, 700, 750, 800, 850, 900, 100, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, or 3790 nt in length of the sequence shown in SEQ ID NO:3 are also useful according to the present invention as are fragments corresponding to most, if not all, of the nucleotide sequence of the cDNA clone contained in the plasmid deposited as ATCC Deposit No. 97767 or as shown in SEQ ID NO:3. By a fragment at least 20 nt in length, for example, is intended fragments which include 20 or more contiguous bases from the nucleotide sequences of the deposited cDNAs or the nucleotide sequences as shown in FIGS. 1A–1D (SEQ ID NO:1) or FIGS. 2A–2E (SEQ ID NO:3). Since the genes have been deposited and the nucleotide sequences shown in FIGS. 1A–1D (SEQ ID NO:1) and FIGS. 2A–2E (SEQ ID NO:3) are provided, generating such DNA fragments would be routine to the skilled artisan.

Preferred nucleic acid fragments of the present invention include nucleic acid molecules encoding epitope-bearing portions of the hPrt1 protein. In particular, such nucleic acid fragments of the present invention include nucleic acid molecules encoding: a polypeptide comprising amino acid residues from about 1 to about 188 in FIGS. 1A–1D (SEQ ID NO:2); a polypeptide comprising amino acid residues from about 193 to about 235 in FIGS. 1A–1D (SEQ ID NO:2); a polypeptide comprising amino acid residues from about 248 to about 262 in FIGS. 1A–1D (SEQ ID NO:2); a polypeptide comprising amino acid residues from about 270 to about 350 in FIGS. 1A–1D (SEQ ID NO:2); a polypeptide comprising amino acid residues from about 361 to about 449 in FIGS. 1A–1D (SEQ ID NO:2); a polypeptide comprising amino acid residues from about 458 to about 620 in FIGS. 1A–1D (SEQ ID NO:2); and a polypeptide comprising amino acid residues from about 639 to about 846 in FIGS. 1A–1D (SEQ ID NO:2). The inventors have determined that the above polypeptide fragments are antigenic regions of the hPrt1 protein. Methods for determining other such epitope-bearing portions of the hPrt1 protein are described in detail below.

Preferred nucleic acid fragments of the present invention also include nucleic acid molecules encoding epitope-bearing portions of the p97 protein. In particular, such nucleic acid fragments of the present invention include nucleic acid molecules encoding: a polypeptide comprising amino acid residues from about 1 to about 98 in FIGS. 2A–2E (SEQ ID NO:4); a polypeptide comprising amino acid residues from about 121 to about 207 in FIGS. 2A–2E (SEQ ID NO:4); a polypeptide comprising amino acid residues from about 232 to about 278 in FIGS. 2A–2E (SEQ ID NO:4); a polypeptide comprising amino acid residues from about 287 to about 338 in FIGS. 2A–2E (SEQ ID NO:4); a polypeptide comprising amino acid residues from about 347 to about 578 in FIGS. 2A–2E (SEQ ID NO:4); a polypeptide comprising amino acid residues from about 593 to about 639 in FIGS. 2A–2E (SEQ ID NO:4); a polypeptide comprising amino acid residues from about 681 to about 770 in FIGS. 2A–2E (SEQ ID NO:4); a polypeptide comprising amino acid residues from about 782 to about 810 in FIGS. 2A–2E (SEQ ID NO:4); and a polypeptide comprising amino acid residues from about 873 to about 905 in FIGS. 2A–2E (SEQ ID NO:4). The inventors have determined that the above polypeptide fragments are antigenic regions of the p97 protein. Methods for determining other such epitope-bearing portions of the p97 protein are also described in detail below.

In another aspect, the invention provides isolated nucleic acid molecules comprising polynucleotides which hybridize under stringent hybridization conditions to a portion of a polynucleotide in nucleic acid molecules of the invention described above, for instances, the cDNA clones contained in ATCC Deposits Nos. 97766 and 97767. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 Mg/ml denatured, sheared salmon sperm DNA, followed by washing the filters in 0.1×SSC at about 65° C.

By polynucleotides which hybridize to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNAs or the nucleotide sequences as shown in FIGS. 1A–1D (SEQ ID NO:1) and FIGS. 2A–2E (SEQ ID NO:3)). Of course, a polynucleotide which hybridizes only to a poly A sequence (such as the 3' terminal poly(A) tract of the hPrt1 and p97 cDNAs, shown in FIGS. 1A–1D (SEQ ID NO:1) and FIGS. 2A–2E (SEQ ID NO:3)), or to a complementary stretch of T (or U) resides, would not be included in polynucleotides of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

Nucleic acid molecules of the present invention which encode the hPrt1 and p97 polypeptides may include, but are not limited to those encoding the amino acid sequences of the mature polypeptides, by themselves; the coding sequences for the mature polypeptides and additional sequences, such as those encoding amino acid leaders or secretory sequences, such as a pre-, or pro- or preproprotein sequences; the coding sequences of the mature polypeptides, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequences encoding the polypeptides of the present invention may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the hPrt1 or p97 fused to Fc at the N- or C-terminus.

The present invention further relates to variants of the nucleic acid molecules of the present invention, which encode portions, analogs or derivatives of the hPrt1 and p97 proteins. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the full-length hPrt1 or p97 polypeptide having the complete amino acid sequence in FIGS. 1A–1D (SEQ ID NO:2) (amino acid residues from about 1 to about 873) and FIGS. 2A–2E (SEQ ID NO:4) (amino acid residues from about 1 to about 907); (b) a nucleotide sequence encoding the full-length hPrt1 or p97 polypeptide having the complete amino acid sequence in FIGS. 1A–1D (SEQ ID NO:2) (amino acid residues from about 2 to about 873) and FIGS. 2A–2E (SEQ ID NO:4) (amino acid residues from about 2 to about 907) but lacking the N-terminal amino acid residue; (c) a nucleotide sequence encoding the hPrt1 or p97 polypeptide having the amino acid sequence encoded by the cDNA clones contained in ATCC Deposit Nos. 97766 and 97767, respectively; or (d) a nucleotide sequence complementary to any of the nucleotide sequences in (a), (b) or (c).

By a polynucleotide having a nucleotide sequence at least, for example, 95% "identical" to a reference nucleotide sequence encoding either an hPrt1 or p97 polypeptide is intended that the nucleotide sequence of a polynucleotide which is identical to the reference sequence except that the polynucleotide sequence may include up to five point mutations per each 100 nucleotides of the reference nucleotide sequences encoding the hPrt1 or p97 polypeptides. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequences shown in FIGS. 1A–1D (SEQ ID NO:1) and FIGS. 2A–2E (SEQ ID NO:3) or to the nucleotide sequences of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981)), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequences shown in FIGS. 1A–1D (SEQ ID NO:1), FIGS. 2A–2E (SEQ ID NO:3), or to the nucleic acid sequence of the deposited cDNAs, irrespective of whether they encode a polypeptide having hPrt1 or p97 activity. This is because even where a particular nucleic acid molecule does not encode a polypeptide having such activity, one of skill in the art would still know how to use the nucleic acid molecule, for instance, as a hybridization probe or a polymerase chain reaction (PCR) primer.

Preferred, however, are nucleic acid molecules having sequences at least 95%, 96%, 97%, 98% or 99% identical to the nucleic acid sequences shown in FIGS. 1A–1D (SEQ ID NO:1), FIGS. 2A–2E (SEQ ID NO:3), or to the nucleic acid sequences of the deposited cDNAs which do, in fact, encode a polypeptide having hPrt1 or p97 protein activity. By "a polypeptide having hPrt1 or p97 activity" is intended polypeptides exhibiting activity similar, but not necessarily identical, to an activity of either the hPrt1 or p97 protein of the invention, as measured in a particular biological assay. For instance, p97 protein activity can be measured using the ability of a p97 homolog to either suppress translation or bind to eIF4A or eIF3, as described in the Examples below. hPrt1 protein activity can be measured, for example, using the ability of an hPrt1 homolog to interact with proteins in the eIF3 complex, also as described in the Examples below.

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequences of the deposited cDNAs or the nucleic acid sequences shown in FIGS. 1A–1D (SEQ ID NO:1) or FIGS. 2A–2E (SEQ ID NO:3) will encode a polypeptide "having hPrt1 or p97 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode polypeptides having hPrt1 or p97 protein activity.

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. These studies have revealed that proteins are surprisingly tolerant of amino acid substitutions. The authors further indicate which amino acid changes are likely to be permissive at a certain position of the protein. Numerous phenotypically silent substitutions are described in Bowie, J. U. et al., supra, and the references cited therein.

Vectors and Host Cells

The present invention also relates to vectors which include the isolated DNA molecules of the present invention, host cells which are genetically engineered with the recombinant vectors, and the production of hPrt1 and p97 polypeptides or fragments thereof by recombinant techniques.

The polynucleotides may be joined to a vector containing a selectable marker for propagation in a host. The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL-5 receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The hPrt1 and p97 proteins can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated.

hPrt1 and p97 Polypeptides and Fragments

The invention further provides isolated hPrt1 and p97 polypeptides having the amino acid sequences encoded by the deposited cDNAs, or the amino acid sequences shown in FIGS. 1A–1D (SEQ ID NO:2) and FIGS. 2A–2E (SEQ ID NO:4), or a peptide or polypeptide comprising a portion of the above polypeptides.

It will be recognized in the art that some amino acid sequences of the hPrt1 and p97 polypeptides can be varied without significant effect on the structure or function of the proteins. Thus, the invention further includes variations of the hPrt1 and p97 polypeptides which show substantial hPrt1 and p97 polypeptide activities or which include regions of hPrt1 and p97 proteins such as the portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptides of FIGS. 1A–1D (SEQ ID NO:2), FIGS. 2A–2E (SEQ ID NO:4), or those encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide.

Of particular interest are substitutions of charged amino acids with another charged amino acid and with neutral or negatively charged amino acids. The latter results in proteins with reduced positive charge to improve the characteristics of the hPrt1 and p97 proteins. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| Aromatic | Phenylalanine |
| | Tryptophan |
| | Tyrosine |

TABLE 1-continued

Conservative Amino Acid Substitutions.

| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above and below. Generally speaking, the number of substitutions for any given hPrt1 or p97 polypeptide, or mutant thereof, will not be more than 50, 40, 30, 20, 10, 5, or 3, depending on the objective.

Amino acids in the hPrt1 and p97 proteins of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such the ability to bind to cellular transcription factors or RNA.

The polypeptides of the present invention are preferably provided in an isolated form. By "isolated polypeptide" is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of the hPrt1 and p97 polypeptides can be substantially purified by the one-step method described in Smith and Johnson, *Gene* 67:31–40 (1988).

The polypeptides of the present invention include the polypeptides encoded by the deposited cDNAs; a polypeptide comprising amino acids from about 1 to about 873 in SEQ ID NO:2; a polypeptide comprising amino acids from about 1 to about 907 in SEQ ID NO:4; a polypeptide comprising amino acids from about 2 to about 873 in SEQ ID NO:2; a polypeptide comprising amino acids from about 2 to about 907 in SEQ ID NO:4; as well as polypeptides which are at least 90% or 95% identical, more preferably at least 96% identical, still more preferably at least 97%, 98% or 99% identical to those described above and also include portions of such polypeptides with at least 30 amino acids and more preferably at least 50 amino acids.

The polypeptides of the present invention include polypeptides at least 90% or 95% identical, more preferably at least 96% identical, still more preferably at least 97%, 98% or 99% identical to either the polypeptides encoded by the deposited cDNAs or the polypeptides of FIGS. 1A–1D (SEQ ID NO:2) or FIGS. 2A–2E (SEQ ID NO:4), and also include portions of such polypeptides with at least 30 amino acids and more preferably at least 50 amino acids.

By a polypeptide having an amino acid sequence at least, for example, 95% "identical" to a reference amino acid sequence of an hPrt1 or p97 polypeptide is intended that the amino acid sequence of the polypeptide is identical to the reference sequence except that the polypeptide sequence may include up to five amino acid alterations per each 100 amino acids of the reference amino acid of either the hPrt1 or p97 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIGS. 1A–1D (SEQ ID NO:2), FIGS. 2A–2E (SEQ ID NO:4) or to the amino acid sequence encoded by one of the deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptides of the present invention are useful as a molecular weight marker on SDS-PAGE gels or on molecular sieve gel filtration columns using methods well known to those of skill in the art.

In another aspect, the invention provides a peptide or polypeptide comprising an epitope-bearing portion of the polypeptides of the invention. The epitope of these polypeptide portions is an immunogenic or antigenic epitope of polypeptides described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

It is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R., *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to polypeptides of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of polypeptides of the invention.

Non-limiting examples of antigenic polypeptides or peptides that can be used to generate hPrt1-specific antibodies include: a polypeptide comprising amino acid residues from about 1 to about 188 in FIGS. 1A–1D (SEQ ID NO:2); a polypeptide comprising amino acid residues from about 193 to about 235 in FIGS. 1A–1D (SEQ ID NO:2); a polypeptide comprising amino acid residues from about 248 to about 262 in FIGS. 1A–1D (SEQ ID NO:2); a polypeptide comprising amino acid residues from about 270 to about 350 in FIGS. 1A–1D (SEQ ID NO:2); a polypeptide comprising amino acid residues from about 361 to about 449 in FIGS. 1A–1D (SEQ ID NO:2); a polypeptide comprising amino acid residues from about 458 to about 620 in FIGS. 1A–1D (SEQ ID NO:2); and a polypeptide comprising amino acid residues from about 639 to about 846 in FIGS. 1A–1D (SEQ ID NO:2). As indicated above, the inventors have determined that the above polypeptide fragments are antigenic regions of the hPrt1 protein.

In addition, non-limiting examples of antigenic polypeptides or peptides that can be used to generate p97-specific antibodies include: a polypeptide comprising amino acid residues from about 1 to about 98 in FIGS. 2A–2E (SEQ ID NO:4); a polypeptide comprising amino acid residues from about 121 to about 207 in FIGS. 2A–2E (SEQ ID NO:4); a polypeptide comprising amino acid residues from about 232 to about 278 in FIGS. 2A–2E (SEQ ID NO:4); a polypeptide comprising amino acid residues from about 287 to about 338 in FIGS. 2A–2E (SEQ ID NO:4); a polypeptide comprising amino acid residues from about 347 to about 578 in FIGS. 2A–2E (SEQ ID NO:4); a polypeptide comprising amino acid residues from about 593 to about 639 in FIGS. 2A–2E (SEQ ID NO:4); a polypeptide comprising amino acid residues from about 681 to about 770 in FIGS. 2A–2E (SEQ ID NO:4); a polypeptide comprising amino acid residues from about 782 to about 810 in FIGS. 2A–2E (SEQ ID NO:4); and a polypeptide comprising amino acid residues from about 873 to about 905 in FIGS. 2A–2E (SEQ ID NO:4). As indicated above, the inventors have determined that the above polypeptide fragments are antigenic regions of the p97 protein.

The epitope-bearing peptides and polypeptides of the invention may be produced by any conventional means. Houghten, R. A., *Proc. Natl. Acad. Sci. USA* 82:5131–5135 (1985). This "Simultaneous Multiple Peptide Synthesis (SMPS)" process is further described in U.S. Pat. No. 4,631,211.

As one of skill in the art will appreciate, the hPrt1 and p97 polypeptides of the present invention and the epitope-bearing fragments thereof described above can be combined with parts of the constant domain of immunoglobulins (IgG), resulting in chimeric polypeptides. Fusion proteins that have a disulfide-linked dimeric structure due to the IgG part can be more efficient in binding and neutralizing other molecules than the monomeric protein or protein fragment alone (Fountoulakis et al., *J. Biochem* 270:3958–3964 (1995)).

hPrt1 and p97Polypeptides: Use for Screening for Agonists and Antagonists of hPrt1 and p97Polypeptide Function In one aspect, the present invention is directed to a method for enhancing an activity of an hPrt1 (e.g., modulation of apoptosis, the ability to bind RNA or other known cellular ligands (such as p170 and eIF4G), participation in the process of translation) or p97 (e.g., modulation of apoptosis, the ability to bind eIF4A and eIF3, suppression of translation) polypeptide of the present invention, which involves administering to a cell which expresses the hPrt1 and/or p97 polypeptide an effective amount of an agonist capable of increasing an activity of either the hPrt1 or p97 protein. Preferably, the hPrt1 or p97 polypeptide mediated activity is increased to treat a disease.

In a further aspect, the present invention is directed to a method for inhibiting an activity of an hPrt1 or p97 polypeptide of the present invention, which involves administering to a cell which expresses the hPrt1 and/or p97 polypeptide an effective amount of an antagonist capable of decreasing an activity of either the hPrt1 or p97 protein. Preferably, hPrt1 or p97 polypeptide mediated activity is decreased to also treat a disease.

By "agonist" is intended naturally occurring and synthetic compounds capable of enhancing or potentiating an activity of an hPrt1 or p97 polypeptide of the present invention. By "antagonist" is intended naturally occurring and synthetic compounds capable of inhibiting an activity of an hPrt1 or p97 polypeptide. Whether any candidate "agonist" or "antagonist" of the present invention can enhance or inhibit an activity can be determined using art-known assays, including those described in more detail below.

Thus, in a further aspect, a screening method is provided for determining whether a candidate agonist or antagonist is capable of enhancing or inhibiting a cellular activity of an hPrt1 or p97 polypeptide. The method involves contacting cells which express one or both of the hPrt1 or p97 polypeptides with a candidate compound, assaying a cellular response, and comparing the cellular response to a standard cellular response, the standard being assayed when contact is made with the polypeptide(s) in absence of the candidate compound, whereby an increased cellular response over the standard indicates that the candidate compound is an agonist of the polypeptide activity and a decreased cellular response compared to the standard indicates that the candidate compound is an antagonist of the activity. By "assaying a cellular response" is intended qualitatively or quantitatively measuring a cellular response to a candidate compound and either an hPrt1 or p97 polypeptide (e.g., modulation of apoptosis, the ability to bind RNA or other known cellular ligands, participation in the process of translation).

Potential antagonists include the hPrt1 RRM and fragments thereof, e.g., hPrt1 polypeptide fragments that include the RNA binding domain. Such forms of the protein, which may be naturally occurring or synthetic, antagonize hPrt1 polypeptide mediated activity by competing for binding to RNA. Thus, such antagonists include fragments of the hPrt1 that contain the ligand binding domains of the polypeptides of the present invention.

Additional agonists according to the present invention include fragments of the p97 polypeptide capable of suppressing translation.

Proteins and other compounds which bind the hPrt1 or p97 polypeptide domains are also candidate agonist and antagonist according to the present invention. Such binding compounds can be "captured" using the yeast two-hybrid system (Fields and Song, *Nature* 340:245–246 (1989); Gyuris et al., *Cell* 75:791–803 (1993); Zervos et al., *Cell* 72:223–232 (1993)).

hPrt1 and p97 polypeptide antagonists also include small molecules which bind to and occupies active regions of the hPrt1 or p97 polypeptide thereby making the polypeptide inaccessible to ligands which bind thereto such that normal biological activity is prevented. Examples of small molecules include but are not limited to nucleotide sequences and small peptides or peptide-like molecules. Such molecules may be produced and screened for activity by a variety of methods (e.g., Light and Lemer, *Bioorganic & Medicinal Chemistry* 3(7):955–967 (1995); Cheng et al., *Gene* 171:1–8 (1996); Gates et al., *J. Mol. Biol.* 255:373–386 (1996)).

In Vitro Translation Systems

The polypeptides of the present invention are also valuable for use in in vitro translation systems. The events leading to the initiation of protein synthesis in eukaryotic cells have been studied using both reconstitution of translational systems using purified components and, more recently, genetic analyses. Hannig, *BioEssays* 17(11):915–919 (1995). There remains, however, a current need for identifying molecules involved in translation and the role each of those molecules play in the process of translation. The present invention provides two such molecules: hPrt1 and p97.

Several commercially available kits are currently on the market for performing translation in vitro. See, e.g., Boehringer Mannheim, Indianapolis, Ind., Cat. Nos:1559 451, 1103 059, 1103 067; Life Technologies, Grand Island, N.Y., Cat. Nos:18127-019, 18128-017. These kits generally provide lysates derived from either whole animal or plant cells which are capable of producing protein from mRNA. These lysates are generally used as part of a translation reaction mixture which contains, in addition to the lysate, mRNA and both labeled and unlabeled amino acids. Thus, while the process of translation can generally be performed to produce a protein of interest, the mechanism by which those proteins are produced has not yet been fully elucidated.

The present invention provides individual components of these cell lysates which are useful for studying the process of translation. The p97 protein, for example, as a putative competitive inhibitor of eIF4G which suppresses both cap dependent and independent translation, is useful for identifying mechanisms by which gene expression is regulated at the translational level. The p97 protein may also be useful for identifying specific genes which are regulated at the translational level.

Similarly, the present invention also provides the hPrt1 protein which is believed to be both a member of the eIF3 complex and a necessary component of translation systems. In order for researchers to fully reconstitute a translation system from individual proteins each of the proteins of that system must be identified and available in purified form. The present invention provides the hPrt1 protein as one of those components. Such reconstitution studies will be useful in elucidating the specific role of each component of the system. For example, the processes of both initiation of proteins synthesis and elongation of the resulting polypeptide chain can be studied by either altering the ratios of the various components or leaving one or more component out of the reaction mixture.

In addition, the present invention provides fragments and homologs of the hPrt1 and p97 polypeptides, produced as described above, which act as either agonists or antagonists of the hPrt1 and p97 proteins. Such fragments of the hPrt1 polypeptide may be useful, for example, for inhibiting translation by blocking the binding of native hPrt1 with either other proteins to form the eIF3 complex or RNA. In addition, such fragments of the p97 polypeptide may be useful, for example, for competitively inhibiting eIF4G.

Having generally described the invention, the same will be more readily understood by reference to the following examples, which are provided by way of illustration and are not intended as limiting.

EXAMPLE 1

Materials

Materials were obtained from the following sources: T7 DNA polymerase sequencing kit, Pharmacia LKB Biotechnologies. Protein A-Sepharose, Repligen. Heart muscle kinase, Sigma. Hybond-N+ nylon membrane, chemiluminescence system, Amersham. Poyvinylidene fluoride membrane, Millipore. $\gamma^{32}$P-ATP (6000 Ci/mmol), $\alpha^{32}$P dCTP (3000 Ci/mmol), $^{35}$S-methionine (1000 Ci/mmol), DuPont-NEN. Oligonucleotides were prepared at the Sheldon Biotechnology Centre, McGill University, Canada.

Isolation of hPrt1 cDNA Clones

The expressed sequence tag used in this study (EST #112738 from Human Genome Science (HGS) Inc.) was identified using established EST methods described previously (Adams, M. D., et al., *Nature* (*London*) 377:3–174 (1995)), and this partial cDNA clone encoding the human homologue of the yeast Prt1 protein was used to obtain the full length cDNA clone. Full length cDNA clones for hPrt1 were isolated from a λgt11 human placenta cDNA library. A 250 bp DNA was generated by the polymerase chain reaction (PCR) using the hPrt1 EST clone as template. The amplified DNA was $^{32}$P-labeled by random priming using a $^{32}$p dCTP, random hexamers and the Klenow fragment of DNA polymerase (Feinberg, A. P., & Vogelstein, B., *Analytical Biochem.* 137:266–267 (1984)), and used as a probe in cDNA screening and Northern blot analysis. For cDNA screening, 5×10$^5$ phages displayed on duplicate sets of filters (Hybond-N+, Amersham) were prehybridized in 5×SSPE (20×SSPE is 3.6 M NaCl, 0.2 M Na$_3$PO4, 0.02 M EDTA, pH 7.7), 5×Denhardt's solution (1×Denhardt's is 0.1% bovine serum albumin, 0.1% Ficoll, 0.1% polyvinylpyrrolidone), 0.5% SDS and 40 μg/ml heat-denatured salmon sperm DNA, for 4 hours at 65° C. Hybridization was performed in the same buffer containing the hPrt1 probe at 1×10$^6$ cpm/ml for 16 hours at 65° C. Filters were washed to a final stringency of 0.1×SSPE/0.1% SDS at 65° C., and exposed to Kodak XAR films for 72 hours with intensifying screens. Phages from positive clones were used to prepare plate lysates and DNA was purified, digested with SalI and ligated into pBluescript that had been digested with SalI. Oligonucleotides used for sequencing were derived from either pBluescript or from the hPrt1 EST DNA sequence. The nucleotide sequence for full length hPrt1-1 was obtained from both strands of independent overlapping clones using the dideoxy chain termination method (Sanger, F., et al., *Proc. Natl. Acad. Sci. USA* 74:5463–5467 (1977)) and the T7 polymerase sequencing kit (Pharmacia). Regions of compression were re-sequenced using 7-deaza dGTP.

Vectors, Proteins

The full length cDNA (clone 3–6) was excised from the λgt11 phage by SalI digestion and inserted into pBluescript KS in the T7 promoter orientation. The resulting vector is designated as KST7hPrt1-6. Constructs for truncated hPrt1 proteins were generated by PCR using primers in which an EcoRI site had been engineered. Cleavage of the PCR product with EcoRI and ligation into pAR90[59/69] (Blanar, M. A., & Rutter, W. J., *Science* 256:1014–1018 (1992)) or pGEX2T[128/129] (Blanar, M. A., & Rutter, W, supra) that had been digested with EcoRI preserves the hPrt1 open reading frame and creates a GST-FLAG-HMK or FLAG-HMK fusion protein. For pAR90 N90146, the forward (5') primer was 5' ACCGGAATTCAAAATGGACGCGGAC-GAGCCCTC 3' (SEQ ID NO:5) and the reverse (3') was primer 5' AGCGGAATTCTTAAATCCCCCACTGCAG 3' (SEQ ID NO:6). For pGEX N255, the hPrt1 open reading frame was first amplified by PCR and inserted into pGEX2T [128/129]. The resulting vector was linearized with HindIII, blunt ended with the Klenow fragment of *E. coli* DNA polymerase and religated. Religation creates a stop codon 3 amino acids downstream of hPrt1 residue 255. pGEX 146–255 was obtained by linearizing pGEX N90146 with HindIII, blunt-ending with Klenow and religating. Vectors were transformed in either *E. coli* BL21 or BL21 pLysS. Bacteria were grown in LB broth to an optical density of 0.5 and protein expression was induced with 1 mM IPTG (isopropyl-b-D-thiogalactopyranoside) for 1 h at 37° C. Cells were pelleted and lysed in lysis buffer (PBS, 1 mM EDTA, 1 mM DTT, 0.1 mM phenylmethylsulfonyl fluoride) by 6 sonication cycles. Debris was removed by centrifugation. GST fusion proteins were purified on glutathione-Sepharose (Pharmacia) as described previously (Methot, N., et al., *Molecular and Cell Biology* 14:2307–2316 (1994)). FLAG-HMK fusion proteins were affinity-purified over an anti-FLAG column (Kodak) according to the manufacturer's specifications. pACTAG-hPrt1 was made by linearizing pACTAG-2 (Charest, A., et al., *Biochem. J.* 308:425–432 (1995)) with NotI, and inserting the hPrt1 ORF that had been excised from KST7hPrt1 cut with NotI. hPrt1 is expressed from this vector as a fusion protein bearing three hemagglutinin (HA) tags at its amino terminus.

In Vitro Transcription and Translation

KST7hPrt1-6 was digested with DraI, and the linearized plasmid was used as template for in vitro transcription using T7 RNA polymerase (Promega) under conditions recommended by the supplier. Translation reactions were performed in nuclease-treated rabbit reticulocyte lysate (Promega) in a final volume of 15 μl. Reaction mixtures contained 10 μl lysate, 10 μCi $^{35}$S-methionine (1000 Ci/Mmole), 15 U RNAsin (Promega), 20 μM amino acid mixture (minus methionine) and 100 ng RNA. The reactions were incubated 60 minutes at 30° C. and stopped by the addition of 3 volumes of Laemmli buffer. Translation products were analyzed by SDS-9% polyacrylamide gel electrophoresis. Gels were fixed, treated in 16% salicylic acid, dried and processed for autoradiography.

Immunoprecipitations, Western Blots of hPrt1 Polypeptides

For HA-hPrt1 protein expression, HeLa cells that had been cultured in Dubelco DMEM media supplemented with 10% fetal bovine serum (FBS) were infected for 1 hour with recombinant vaccinia virus vTF7-3 with the T7 RNA polymerase cDNA inserted into its genome (Fuerst, T. R., et al., *Proc. Natl. Acad. Sci. USA* 83:8122–8126 (1986)), and transfected with 5 μg plasmid DNA using lipofectine (Gibco BRL, Gaithersburg, Md.) in DMEM without FBS. Cells were incubated 2 hours with the DNA-lipofectine mixture, and returned to DMEM-10% FBS for 12 hours before harvesting. The cells were lysed in 20 mM Tris-HCl pH 7.4, 75 mM KCl, 5 mM MgCl$_2$, 1 mM DTT, 10% glycerol, 1% Triton X-100, 1 mM PMSF, aprotinin (25 ng/ml) and pepstatin (1 ng/ml). Cellular debris and nuclei were removed by centrifugation, and protein content was assayed by the Bradford method. Immunoprecipitations were performed on 200 μg of extract using a-HA antibody. Briefly, extracts were diluted to 500 μl in RIPA buffer (50 mM Tris-HCl pH 7.4, 150 mM NaCl, 1% NP40, 0.1% SDS, 0.5% Na-deoxycholate) and incubated on ice for 30 minutes with 1 μg of antibody. Protein-A-sepharose was added and allowed to mix at 4° C. for 60 minutes. The beads were washed 5 times in RIPA buffer before addition Laemmli buffer and boiling for 5 minutes. Immunoprecipitates were then loaded on an SDS-10% polyacrylamide gel, blotted onto nitrocellulose and probed with a goat anti-rabbit eIF3 antibody. Immunoreactive species were visualized using the Renaissance chemiluminescence system (ECL; Amersham). Affinity-purified antibodies against recombinant hPrt1 were obtained as described in Harlow and Lane, ANTIBODIES: A LABORATORY MANUAL, Cold Spring Harbor (1988). *E. coli* extracts expressing hPrt1 N90146 were fractionated by SDS-PAGE and transferred onto nitrocellulose. The bands containing N90146 were excised, blocked in Blotto (10 mM Tris-HCl, pH 7.4, 150 mM NaCl, 0.075% Tween-20, 0.5% milk powder) and incubated with crude α-eIF3, and washed. Antibodies bound to the membrane were eluted with 2 M glycine, 1 mM EGTA, pH 2.5, and neutralized by the addition of 1 M Tris-HCl, pH 8.8. To eliminate contamination with p110 (hNip1), 50 μg of GST-p110 immobilizes on nitrocellulose were present during the incubation with crude α-eIF3 antibodies. Western blotting was performed with antibodies at the following dilutions: α-eIF3, 1:3000. α-p170, 1:10. For western blots performed with the monoclonal α-p170 antibody, horseradish-peroxidase α-mouse IgM (Pierce) secondary antibodies were used; For α-eIF3, α-goat IgG-horseradish peroxidase; For α-hPrt1, α-goat IgG-alkaline phosphatase.

Northern Blot of hPrt1 mRNA

Total RNA from HeLa cells was isolated using Trizol (Life Technologies, Grand Island, N.Y.) and fractionated by electrophoresis in a 1% agarose/formaldehyde gel overnight at 40V. RNA was blotted to Hybond-N+ filters overnight and UV cross-linked to the membrane using UV light. The membrane was prehybridized and hybridized under conditions identical to the cDNA library screening, and exposed for 24 hours to a Kodak BioMax film with intensifying screen.

Far Western Blots

Partially purified FLAG-HMK hPrt1 fusion proteins (1–3 μg) were $^{32}$P-labeled using heart muscle kinase as described (Blanar, M. A., & Rutter, W. J., supra). Proteins were resolved by SDS-polyacrylamide gel electrophoresis and blotted on PVDF membranes (Millipore) or nitrocellulose. The membranes were blocked overnight with 5% milk in HBB buffer (25 mM HEPES-KOH, pH 7.5, 25 mM NaCl, 5 mM MgCl$_2$, 1 mM DTT), and incubated 4 hours in hybridization buffer (20 mM HEPES-KOH pH 7.5, 75 mM KCl, 2.5 mM MgCl$_2$, 0.1 mM EDTA, 1 mM DTT, 0.1% NP-40, 1% milk) containing the $^{32}$P-labeled FLAG-HMK- or GST-FLAG-HMK-hPrt1 at 250,000 cpm/ml and unlabeled purified GST at 1 μg/ml. The membranes were washed 3 times with hybridization buffer and processed for autoradiography.

Results

Cloning and Features of hPRT1

Expressed Sequence Tag (EST) #112738 from Human Genome Science (HGS) Inc. encodes a protein with homology to the yeast p90 eIF3 subunit, Prt1. The cDNA sequence, 2 kbp in length, contained a polyadenylation signal and a short polyadenylate tail. An ATG codon was present at the 5' end of the clone. However, this ATG was not preceded by stop codons. It was therefore possible that EST #112738 contains an incomplete cDNA. A $^{32}$P-labeled probe derived from the 5' end of the EST sequence was generated and used in a Northern analysis on HeLa cell RNA. A single RNA species migrating at 3.1 kb, hybridized with the probe. We concluded that 1 kbp was missing from EST #112738. To obtain the full length cDNA sequence, a human placenta λgt11 cDNA library was screened with the same probe used in the Northern analysis. Forty positive were recovered and some of the cDNAs extended further upstream of the 5'-most sequence of EST #112738. One of these clones, 3–6, contained a 3 kbp insert with a predicted open reading frame of 873 amino acids, shown in FIGS. 1A–1D, (SEQ ID NO:2). An ATG codon, located at nucleotide positions 97–99 downstream of the 5' end, was preceded by an in-frame stop-codon (nucleotide positions 22 to 24, shown in FIGS. 1A–1D (SEQ ID NO:1). Thus, it is likely that clone 3–6 encodes the full length cDNA, and the first ATG constitutes the authentic initiation codon. An in frame CTG codon 24 nt upstream of the first AUG is present and could potentially serve as the initiation site (nucleotide positions 73–75 shown in FIGS. 1A–1D (SEQ ID NO:1)). We have named the protein encoded this cDNA hPrt1, for human-Prt1.

The cDNA sequence of hPrt1 is predicted to encode a protein containing a canonical RNA Recognition Motif (RRM) located between amino acids 185 and 270 (FIGS. 1A–1D (SEQ ID NO:2)). The identification of the hPrt1 RRM is based on the consensus structural core sequences of RRMs (Birney, E., et al., *Nucl. Acids Res.* 21:5803–5816 (1993)), which include the presence of RNP-1 and RNP-2 sequence, and hydrophobic amino acids found at specific positions within the RRM. A BLAST search (Altschul, S. F., et al., *J. Mol. Biol.* 215:403–410 (1990)) with only the hPrt1 RRM revealed that the hPrt1 RRM is most highly related to the fourth RRM of the poly(A) binding protein PABP. No other common protein motifs are evident. hPrt1 is acidic, with a predicted PI of 4.8. The middle portion of the protein is unusually rich in tryptophan residues (close to 5% tryptophan content over 400 amino acids). Amino acid sequence comparison between human and *Saccharomyces cerevisiae* Prt1, reveal extensive sequence identity (31% identity, 50% homology) across the entire protein except for the first 140 amino acids. The similarity between yeast and human Prt1 is more striking in the middle portion of the protein which encompasses the RRM. Several but not all of the tryptophan are conserved, suggesting that they are finctionally important. The amino terminus of human Prt1 is not homologous to yeast Prt1, but instead exhibits 25% identity to procollagen a chain precursor protein (data not shown). The significance of this is not clear. The hPrt1 protein also contains two protein kinase A, six protein kinase C and 17 casein kinase II consensus phosphorylation sites.

hPrt1 is a Part of eIF3

It is conceivable that hPrt1 is a subunit of eIF3. To prove this, an immunological characterization of hPrt1 and eIF3 was performed. First, we translated in vitro a synthetic RNA derived from the hPrt1 cDNA. A single polypeptide, migrating at 116 kDa on an SDS-9% polyacrylamide gel, was obtained. The translation product co-migrated with a 116 kDa protein in a HeLa extract that cross-reacted with α-eIF3. Thus, the size of hPrt1 is similar to one of the eIF3 subunits. Next, we tested the ability of a polyclonal α-eIF3 antibody to recognize hPrt1. To this end, we expressed hPrt1 fused to the hemagglutinin (HA) epitope-tag in HeLa cells using a recombinant vaccinia virus expression system (Fuerst et al., supra). Extracts from infected cells were, blotted onto nitrocellulose and probed with a polyclonal α-eIF3 antibody. eIF3 subunits (p170 and p115) in extracts from cells transfected with the parental vector (pACTAG-2; Charest et al., *Biochem. J.* 308: 425–432 (1995)) or pACTAG-hPrt1 were readily identifiable. A 125 kDa protein that cross-reacts with α-eIF3 was present in extracts from cells transfected with pACTAG-hPrt1 but not in cells transfected with the vector alone. To confirm the identity of this protein as HA-hPrt1, immunoprecipitations using α-HA antibody were performed and the products probed with α-eIF3 antibody. The immunoprecipitated HA-hPrt1 co-migrated with the 125 kDa polypeptide, and cross-reacted with the α-eIF3 antibody. The slower mobility of HA-hPrt1 relative to hPrt1 is probably due to the three HA epitopes present in the fusion protein. Immunoprecipitates from cells transfected with the parental vector or with a vector encoding HA-La autoantigen failed to cross-react with α-eIF3. We conclude that hPrt1 is recognized by an antibody directed against eIF3. Finally we wished to determine whether antibodies directed against hPrt1 could recognize a 116 kDa polypeptide in purified human eIF3. Attempts to generate antibodies against hPrt1 in rabbits failed. To circumvent this problem, affinity-purified hPrt1-specific antibodies from α-eIF3 antisera were prepared from crude eIF3 antibodies, using a bacterially expressed hPrt1 fragment. These antibodies recognized a protein migrating at approximately 116 kDa in a highly purified human eIF3 preparation and in HeLa extracts, and did not cross-react with a hNip1 a 110 kDa protein also recently shown to be an eIF3 component (see the discussion below). Together with the previous data, these experiments strongly suggest that hPrt1 is the 115 kDa subunit of eIF3.

hPrt1 Interacts Directly with the p170 Subunit of eIF3

To further substantiate the finding that hPrt1 is a subunit of human eIF3, we examined the possibility that hPrt1 interacts directly with one or more eIF3 subunits. To this end, hPrt1 was tagged with a FLAG peptide linked to a heart muscle kinase site (FLAG-HMK) or fuised to a glutathione-S-transferase-FLAG-HMK sequence (GST-FLAG-HMK). We opted to use fragments of hPrt1 rather than the full length protein due to the low yield and extensive degradation of full length hPrt1 in $E$ $coli$. The proteins were purified using a FLAG antibody or glutathione-sepharose resin, and were $^{32}$P-labeled with heart muscle kinase. The labeled proteins were then used to detect interacting proteins by the Far Western assay with HeLa cytoplasmic extracts, rabbit reticulocyte lysate and different preparations of eIF3. Two of the probes, GST N255 (amino acids 1–255 of hPrt1 shown in FIGS. 1A–1D (SEQ ID NO:2)) and N90146 (amino acids 147–873 shown in FIGS. 1A–1D (SEQ ID NO:2)), interacted with a 170 kDa protein in HeLa and rabbit reticulocyte lysate. The hPrt1 probes reacted with a 140 kDa protein in eIF3 preparation 1 and 140 and 170 kDa polypeptides in eIF3 preparation 2. A $^{32}$P-labeled probe consisting only of a GST-HMK fusion did not recognize any proteins (data not shown).The 170 kDa protein in HeLa, rabbit reticulocytes and eIF3 preparation 2 could the largest subunit of eIF3, p170. This protein is sensitive to degradation, and the two eIF3 preparations used here differ by the extent of p170 proteolysis. An immunoblot using a monoclonal antibody directed against p170 (Mengod, G., & Trachsel, H., $Biochem.$ $Acta$ 825:169–174 (1985)) revealed the extent of p170 degradation in the eIF3 preparations, and clearly shows that a 140 kDa degradation product of p170 is present in preparation 1, and to a lesser extent in preparation 2. This experiment demonstrates that hPrt1 interacts directly with the p170 subunit of eIF3. No other eIF3 subunits were recognized by the hPrt1 probes in this assay (data not shown).

The fact that both the N90146 and N255 fragments of hPrt1 reacted with p170 suggest that the site of protein-protein interaction is located between amino acids 147 and 255 (FIGS. 1A–1D (SEQ ID NO:2)). This segment of hPrt1, which encompasses most of the RRM, was assessed for its ability to interact with p170 independently of other sequences. A fragment containing amino acids 147 to 255 of hPrt1, used as a probe in a Far Western assay, indeed interacted with p170. To further delineate the interaction site, a fragment consisting of amino acids 147–209 (FIGS. 1A–1D (SEQ ID NO:2)) was tested, and failed to interact with p170 (data not shown). This suggests that a portion of the RRM is crucial for the association between hPrt1 and p170.

Discussion

The present invention provides a human cDNA that with homology to the yeast eIF3 subunit, Prt1. In vitro translation of hPrt1 RNA yielded a polypeptide of 116 kDa that co-migrated with one of the eIF3 subunits. Immunological characterization revealed that hPrt1 cross-reacts with α-eIF3 and that affinity-purified α-hPrt1 antibodies recognize a polypeptide of approximately 120 kDa in highly purified eIF3. Thus, a direct interaction between hPrt1 and the p170 subunit of mammalian eIF3 has been demonstrated. Based on these data, the inventors conclude that hPrt1 corresponds to the second largest subunit of eIF3, p115. The immunoprecipitates of HA-hPrt1 did not contain other eIF3 subunits. It is likely that HA-hPrt1 does not incorporate well into the endogenous eIF3 because of the stability of the complex. Alternatively, the HA-tag may hinder association of HA-hPrt1 with eIF3.

Recently, Hershey and co-workers have isolated a human cDNA predicted to encode a 110 kDa protein which showed homology to the yeast Nip1 protein. Although Nip1 is not present in yeast eIF3 complexes, the human homologue is part of mammalian eIF3. The data disclosed herein suggests that mammalian eIF3 contains two subunits that migrate at approximately 115 kDa. Examination of various rat or rabbit eIF3 preparations resolved on SDS-polyacrylamide gel electrophoresis show two polypeptides migrating at this position (Behlke, J. et al., $Eur.$ $J.$ $Biochem.$ 157:523–530 (1986); Meyer, L. et al., $Biochemistry$ 21:4206–4212 (1982)). Thus, the mammalian eIF3 complex consists of at least 9 polypeptides: p170, p116 (hPrt1), p110 (hNip1), p66, p47, p44, p40, p36 and p35.

Mutations in the PRT1 gene of $Saccharomyces$ $cerevisiae$ impair translation initiation in vivo at 37° C. (Hartwell, L. and McLaughlin, C., $J.$ $Bacteriol.$ 96:1664–1671 (1968); Hartwell, L. and McLaughlin, C., $Proc.$ $Natl.$ $Acad.$ $Sci.$ $USA$ 62:468–474 (1969)). One of the mutants, prt1-1, does not promote binding of the ternary complex eIF2-GTP-tRNAimet to the 40S ribosomal subunit (Feinberg, B., et al., $J.$ $Biol.$ $Chem.$ 257:10846–10851 (1982)). Evans et al. (1995) identified six mutations in PRT1 which impair translation initiation (Evans, D. R. H., et al., $Mol.$ $Cell.$ $Biol.$ 15:4525–4535 (1995)). Two of these mutations alter amino acids that are conserved between yeast and human Prt1. Human Prt1, when expressed in the prt1-1 yeast strain, was unable to rescue the temperature sensitive phenotype (N. Methot, unpublished data). This was somewhat surprising since yeast eIF3 functions in a mammalian methionyl-puromycin assay system (Naranda, T., et al., $J.$ $Biol.$ $Chem.$ 269:32286–32292 (1994)). Methionyl-puromycin synthesis is dependent on the binding of the ternary complex to the 40S ribosome, requires only washed ribosomes, tRNAimet, eIF1A, eIF2, eIF3, eIF5 and eIF5A (Benne, R., et al., $Meth.$ $Enzymol.$ 60:15–35), but does not measure mRNA binding to the ribosome. It is clear that yeast eIF3 can replace mammalian eIF3 for some, but not all normal eIF3 functions, and that hPrt1 is unable to fulfill all the roles of yeast Prt1. One of the reasons why hPrt1 was unable to replace Prt1 in vivo is that it may not incorporate into the yeast eIF3 complex. A Far Western analysis on yeast extracts using the hPrt1 N255 fragment did not reveal any interacting proteins.

Both yeast and human Prt1 contain near their amino terminus an RNA recognition motif(RRM; residues 185–270 in hPrt1, shown in FIGS. 1A–1D (SEQ ID NO:2)). The RRM contains the sequence elements that are responsible for specific protein-protein interactions with the p170 subunit of eIF3. It is unlikely that the interaction between hPrt1 and p170 is mediated through RNA since hPrt1 was unable to bind a radiolabeled RNA probe as measured by UV photocrosslinking and Northwestern assays (N. Methot, unpublished observations). Further, treatment of the FLAG-HMK N90146 probe and the nitrocellulose membrane with RNase A did not reduce the intensity of the interaction with p170 (N. Methot, unpublished data). It is possible that the RRM is functional as an RNA binding module only within the eIF3 complex, and that its RNA binding activity and specificity are modulated by p170. Precedents for protein-protein interactions altering the RNA binding activity of an RRM-containing protein exist. The spliceosomal protein U2B" is unable on its own to distinguish between the U1 and U2 snRNAs, but will bind specifically to U2 snRNA in the presence of the U2A' protein (Scherly, D., *Nature* (*London*) 345:502–506 (1990); Scherly, D., et al., *EMBO J.* 9:3675–3681 (1990)). U2A' and U2B" associate in the absence of RNA, an interaction which is mediated by the RRM (Scherly, D., et al., *EMBO J.*, supra). The major RNA binding protein of yeast eIF3 is the p62 subunit (Naranda, supra). It has been previously shown that the p170 subunit of eIF3 interacts directly with eIF4B (Methot, N., et al., *Mol. Cell. Biol.* in press (1996)). eIF4B and hPrt1 do not appear to interact with the same sites on p170 since hPrt1 reacts very strongly with the 140 kDa degradation product of p170, while eIF4B does not. The numerous protein-protein interactions involving p170 suggest that this protein may serve as a scaffold for both the assembly of the eIF3 complex and for the binding of the mRNA to the ribosome.

EXAMPLE 2

Cloning of cDNAs

The cDNA #20881 was obtained from a human embryo brain cDNA library by random cloning. A human placenta cDNA library in λgt11 was screened with a fragment (nucleotide positions, 473 to 1200, shown in FIGS. 2A–2E (SEQ ID NO:3)) of cDNA #20881. 5'-RACE (rapid amplification of cDNA ends, GIBCO-BRL) was performed with HeLa poly (A)+ RNA and sequence specific primers (594 to 614 and 643 to 664 shown in FIGS. 2A–2E (SEQ ID NO:3)) according to the manufacturer's instructions.

Construction of Plasmids

To generate the carboxyl (C)-terminally HA-tagged cDNAs, an antisense primer composed of the sequences encoding the C-terminal six amino acids of p97 followed by the HA epitope peptide, YPYDVPDYAG (SEQ ID NO:13), and nucleotides corresponding to the Xho I site was used for polymerase chain reaction (PCR) with a sense primer (nucleotides 2527 to 2549 shown in FIGS. 2A–2E (SEQ ID NO:3)). pcDNA3, which has a human cytomegalovirus (CMV) and T7 RNA polymerase promoters, was used as an expression vector for most of the experiments. pcDNA3-4-1-A(HA) and pcDNA3-6-4-A(HA) contain the corresponding p97 cDNA sequences downstream of nucleotide positions 12 and 30 in FIGS. 2A–2E (SEQ ID NO:3), respectively. pcDNA3-ATG-A(HA) contains the sequence downstream of nucleotide 473 and a part of the sequence of transcription factor BTEB (−15 to 10, including the initiator ATG) (Imataka, H., et al., *EMBO J.* 11:3633–3671 (1992)).

For an N-terminally HA-tagged construct, the initiator ATG codon and three copies of the HA sequence (Mader, S., et al., *Mol. Cell. Biol.* 15:4990–4997 (1995)) were inserted into pcDNA3 to generate the parental vector, pcDNA3-HA. A PCR amplified fragment from the GTG initiation codon to a SacI site (nucleotide 600) was ligated to a fragment from SacI to the 3'-terminus of cDNA #20881 to construct pcDNA3-HA-p97. An EcoRI fragment of the human eIF4G cDNA (kindly provided by Dr. Rhoads; Yan, R., et al., *J. Biol. Chem.* 267:23226–23231 (1992)) was used to construct pcDNA3-HA-eIF4G. HA-La was inserted into pcDNA3 to obtain pcDNA3-HA-La.

For expression of non-tagged p97, a fragment from a BamHI restriction site (nucleotide 172 (FIGS. 2A–2E (SEQ ID NO:3)) to the 3'-terminus in which the initiator GTG had been mutated into ATG, was inserted into pcDNA3 to generate pcDNA3Bam-ATGp97. A point mutation (GTG to ATG or to GGG) was introduced using a commercial kit (Amersham). To construct pcDNA3-eIF4G, the EcoRI fragment of eIF4G cDNA was inserted into pcDNA3.

The poliovirus internal ribosome entry site (IRES) was inserted into pSP72, which contains the T7 RNA polymerase promoter, to generate pSP72IRES. For expression of p97 or eIF4G in a cap-independent manner, the Bam-ATGp97 and the EcoRI fragment of eIF4G cDNA were inserted downstream of the IRES to construct pSP72IRES-p97 and pSP72IRES-eIF4G.

Transient Transfection

HeLa cells were infected with recombinant vaccinia virus vTF7-3 (Fuerst et al., supra), and then transfected with plasmids (5 μg) using Lipofectin (Gibco-BRL, Gaithersburg, Md.). For expression in COS-1 cells, plasmids (10 μg) were transfected by electroporation (Bio-Rad Gene PulserII, 1200V, 25 mF).

Immunoprecipitation

After transfection, HeLa and COS-1 cells were cultured for 16 hours and 48 hours, respectively, and then labeled with [$^{35}$S] methionine(100 μCi/ml) for 1 hour in 3 cm dishes. Cells were lysed in 0.5 ml buffer A (150 mM NaCl, 1% NP-40, 0.1% deoxycholate, 1 mM phenylmethylsulfonyl fluoride (PMSF), 1 mM dithiothreitol (DTT), 50 mM Tris-HCl, pH 7.4). After centrifugation, the supernatant was mixed with 2 μg of anti-HA antibody (12CA5) for 6 hours in the cold room at 4° C. Protein G sepharose (30 ml of 50% slurry) was added and the mixture was incubated for 2 hours. After washing with buffer A (1 ml, three times), immunoprecipitates were collected by centrifugation and proteins were eluted with Laemmli buffer for SDS-10% polyacrylamide gel electrophoresis (SDS-PAGE). For co-immunoprecipitation experiments, transfected HeLa cells (6 cm dish) were lysed in 1 ml buffer B (100 mM KCl, 0.5 mM EDTA, 20 mM HEPES-KOH pH 7.6, 0.4% NP-40, 20% glycerol, 1 mM DTT, 1 mM PMSF, 5 μg/ml pepstatin, 5 μg/ml leupeptin). After centrifugation, an aliquot (0.5 ml) was mixed with anti-HA antibody (2 μg). Immuprecipitates were washed with buffer B (1 ml, three times), and resolved by SDS-10% PAGE, except for eIF4E experiments where 12.5% polyacrylamide gels were used.

Western Blotting and Antibodies

Immunoprecipitates or cell extracts (60 μg protein) were resolved by SDS-PAGE and transferred to Immobilon polyvinylidene difluoride membrane (Millipore). Protein bands were visualized by chemiluminescence (Amersham). Quantification was done with a laser densitometer (LKB).

Anti-p97 antibodies: The peptide, SDETDSSSAPSKEQ (called INT, amino acids 788 to 802, shown in FIGS. 2A–2E (SEQ ID NO:4)) conjugated with keyhole limpet hemacyanin was used to raise anti-peptide(INT) antibody in rabbits. For absorption experiments, serum was pre-incubated with the INT peptide (10 μg) on ice for 1 hour, and was used for Western blotting. A fusion protein GST-C-terminus, glutathione-S-transferase linked to the peptide ETAEEEE- SEEEAD (amino acids, 895 to 907, shown in FIGS. 2A–2E (SEQ ID NO:4)) was produced in *E. coli* for immunization in rabbits. The resulting serum was passed through a GST or GST-C-terminus column for adsorption.

CAT Assay and RNase Protection Assay

Chloramphenicol acetyltransferase (CAT) assay was performed as described (Gorman, C. M., et al., *Mol. Cell. Biol.* 2:1044–1051 (1982)). RNase protection assay was done as described (Imataka, H., et al., *EMBO J.* 11:3633–3671 (1992)) with modifications as follows: as an internal control, in vitro synthesized unlabeled BTEB RNA and radiolabeled antisense RNA to BTEB sequence (Imataka, H., et al., *EMBO J.* 11:3633–3671 (1992)) were mixed with antisense CAT probe. Intensities of the CAT and BTEB signals were quantified by PhosphorImager BAS 2000. The amount of CAT mRNA was normalized to that of the internal control BTEB RNA. Translation activity was calculated by dividing CAT activity by the normalized CAT mRNA amount.

In Vitro Transcription and Translation

Capped RNA was synthesized by T7 RNA polymerase in the presence of the cap analogue, m$^7$GpppG. Rabbit reticulocyte lysate (25 μl, final volume) was programmed with 0.2 μg of mRNA in the presence of [$^{35}$S]methionine (20 μCi) according to the manufacturer's recommendation.

Binding Assay for in Vitro Translated Factors

Following translation, five microliters of the lysate was incubated on ice for 30 minutes with anti-FLAG resin (20 μl) to which FLAG-eIF4E or FLAG-eIF4A had been bound. After washing with buffer C consisting of 50 mM Tris-HCl (pH, 7.5), 1 mM EDTA, 0.15 M NaCl and 0.1% NP-40 (1 ml, three times), bound proteins were eluted with 40 μl of buffer C containing 100 μg/ml FLAG peptide. pAR(DRI) [59/60] (Blanar, M. A., & Rutter, W. J., supra) was used to express FLAG-eIF4E (Pause, A., et al., *Nature* 371:762–767 (1994)) and FLAG-eIF4A in *E. coli*.

Inducible Expression of p97 p97 cDNA (nucleotides 36 to 3810 in FIGS. 2A–2E (SEQ ID NO:3)), in which the initiator GTG codon was converted to ATG, was inserted into a tetracycline-dependent expression vector, pRep9-CMVt (Beauparlant, P., et al., *J. Biol. Chem.* 271:10690–10696 (1996)) to construct pRep9-CMVt-p97. An NIH3T3-derived cell line, S2-6 (Shockett, P., et al., *Proc. Natl. Acad. Sci. USA* 92:6522–6526 (1995)) was transformed with pRep9-CMVt (control) or with pRep9-CMVt-p97 using G418 (400 μg/ml). S2-6 and the established transformants were maintained in the presence of 1 μg tetracycline/ml. To induce p97 expression, cells were cultured in medium without tetracycline for 40 hours. After induction, cells were processed for Western blotting or labeled with [2, 3, 5-$^3$H] leucine (20 μCi/ml). Cells were lysed with buffer B and extracts (20 μg protein) were applied to filter paper. After washing with trichloroacetic acid (5%), radioactivity remaining on the paper was counted.

Results

The GUG-initiated Open Reading Frame Encodes a Variant of eIF4G

A human cDNA clone #20881 (hereafter called clone A, nucleotide positions 473 to 3820 in FIGS. 2A–2E (SEQ ID NO:3)) was found to possess an open reading frame (ORF) encoding a protein (850 amino acids) similar to eIF4G. RNA synthesized from clone A produced no protein in a reticulocyte lysate translation system (data not shown). The ORF of clone A had no translation initiator ATG; the first in-frame ATG (nucleotide positions 925–927, shown in FIGS. 2A–2E (SEQ ID NO:3)) is unlikely to be the initiation codon, since there are eleven upstream ATGs which are out of frame between nucleotide positions 473 and 927. Thus, upstream sequences which could provide the translation initiator are lacking from clone A. The 3'-terminus is complete because of the presence of the poly (A) signal and a poly (A) tail (FIGS. 2A–2E (SEQ ID NO:3)). To obtain a full length cDNA, we screened a human placenta cDNA library with a 5' sequence of clone A. 14-1, the longest clone obtained, starts at nucleotide position 12 in FIGS. 2A–2E (SEQ ID NO:3) and the sequence was extended by 11 nucleotides by 5'-RACE. The longest sequence (3820 nucleotides) (FIGS. 2A–2E (SEQ ID NO:3)) is close to full-length, since Northern blotting showed that the mRNA is approximately 3.8 kb in length. The mRNA is expressed in every tissue and cell line examined, implying a fundamental role of the protein in cells. The first ATG of the extended ORF is the same as that identified in clone A (nucleotide positions 925–927 shown in FIGS. 2A–2E (SEQ ID NO:3)) and there are in-frame stop codons at nucleotide positions 178 and 205. The sequence 4-1-A (nucleotides 12 to 3820 shown in FIGS. 2A–2E (SEQ ID NO:3)) was used for further studies.

To determine the capacity of the full length cDNA to encode a protein, a modified cDNA, 4-1-A(HA), in which the hemagglutinin (HA) epitope was fused to the C-terminus of the ORF, was transfected into COS-1 and HeLa cells. Western blotting and immunprecipitation with anti-HA antibody demonstrated that a 97 kDa protein (called, p97-HA) was synthesized. Transfection of a truncated cDNA, ATG-A(HA), in which an artificial ATG was inserted in frame to initiate the ORF of clone A, yielded a shorter polypeptide than p97-HA. The apparent molecular mass of this shorter protein is 95 kDa, which is close to the expected size from the sequence of clone A (97 kDa, ORF of clone A plus HA). These results indicate that the full-length cDNA encodes a protein which is larger than that encoded by the ORF starting from position 473. One explanation for this is that translation of this protein starts at a non-AUG initiator 5' upstream of clone A. Although there is one ATG triplet in the 5' upstream region (nucleotide positions 21–23 shown in FIGS. 2A–2E (SEQ ID NO:3)), it is predicted to encode a small polypeptide (16 amino acids), and is out of frame of clone A ORF. Furthermore, transfection of 6-4-A(HA), which does not contain this ATG (FIGS. 2A–2E (SEQ ID NO:3)), produced a protein indistinguishable from p97-HA.

We predicted that GTG at nucleotide positions 307 to 309 (FIGS. 2A–2E (SEQ ID NO:3)) is the translation initiator, since it could potentially start an ORF that encodes a polypeptide of about 100 kDa, and the nucleotide sequence flanking this triplet (GCCGCCAAAGUGGAG, nucleotides 298–312 in FIGS. 2A–2E (SEQ ID NO:3)) is similar to the consensus sequence for non-AUG initiators (Boeck, R. & Kolakofsky, D. *EMBO J.* 13:3608–3617 (1994); Grunert, S. & Jackson, R., *EMBO J.* 13:3618–3630 (1994)). To test this possibility, we mutated the GTG into GGG or ATG in the 4-1-A(HA) construct, and transfected the DNA into HeLa cells. The ATG mutant yielded 4 fold more p97-HA protein than the wild type from similar amounts of RNA, while the GGG mutant failed to produce the protein. In vitro translation experiments confirmed the in vivo results. When the 4-1-A(HA) RNA was translated in a rabbit reticulocyte lysate, p97-HA was synthesized as a single product. A point mutation (GUG to GGG) abolished translation, while a mutation to AUG increased translation of p97-HA by 2 fold. From these data, we conclude that translation of p97 mRNA exclusively starts at the GUG codon (positions 307–309 in FIGS. 2A–2E (SEQ ID NO:3)) to encode a polypeptide of 907 amino acids (FIGS. 2A–2E (SEQ ID NO:3)). This mode of translation is apparently not specific to the human p97 mRNA, since the cDNA sequence of the mouse p97 homologue also lacks an initiator ATG, and the GTG codon is conserved.

To verify the presence of p97 protein in cells, we used two different antisera raised against the same p97 peptide sequences as were used above in Western blotting. Experiments were performed with extracts from a mouse cell line Neuro2A, since anti-GST-C serum pre-incubated with GST or GST-C detects polypeptides between 95 and 100 kDa with extracts from primate cell lines, including HeLa and COS-1, and these non-specific bands obscure the p97 band (data not shown). Anti-GST-C-terminal peptide antiserum detected two bands with apparent molecular masses of 97 and 65 kDa, both of which disappeared when the serum was absorbed with the antigen. The 65 kDa polypeptide is likely a cross-reacting material, since another serum, anti-peptide (INT) serum, did not detect this band. In contrast, the 97 kDa band was also detected by the latter serum, and disappeared by treatment of the serum with the peptide (INT). Thus, the 97 kDa polypeptide is the only common polypeptide that is specifically recognized by the two different antisera. To further substantiate the authenticity of the 97 kDa polypeptide, we expressed non-tagged p97 from a cDNA. HeLa cells were employed for transfection because of their better transfection efficiency. The amount of p97 was increased by 4 fold following transfection with a non-tagged p97 expression plasmid, pcDNA3-Bam-ATGp97. Therefore, clearly, p97 is translated from the endogenous mRNA.

p97 Binds to eIF4A and eIF3, but not to eIF4E

Alignment of human p97 and eIF4G amino acid sequences reveals that p97 exhibits 28% identity and 36% similarity to the C-terminal two thirds of eIF4G. The N-terminal third of eIF4G, to which eIF4E binds (Lamphear, B., supra; Mader, S., et al., supra), bears no similarity to p97. Therefore, no canonical eIF4E-binding site (Mader, S., et al., supra) is found in p97. Lamphear, B., et al., supra showed that the C-terminal two thirds of the poliovirus protease-cleaved eIF4G contains the binding sites for eIF4A and eIF3. Thus, it is predicted that p97 would bind to eIF4A and eIF3, but not to eIF4E. To examine this, HA-tagged p97 and eIF4G were expressed in HeLa cells, and cell extracts were immunoprecipitated with anti-HA antibody. The immunoprecipitates were assayed by Western blotting for eIF4A, eIF3 and HA-tagged protein expression. Both eIF4A and eIF3 were co-precipitated with p97 and eIF4G, while an RNA binding protein, La autoantigen (Chambers, J. C., et al., *J. Biol. Chem.* 263:18043–18051 (1988)) failed to precipitate either factor.

The light chain of the HA-antibody co-migrates with eIF4E on SDS-PAGE, rendering detection of immunoprecipitated eIF4E difficult. To circumvent this problem, we co-expressed FLAG-tagged eIF4E, which migrates slower than non-tagged eIF4E, with HA-tagged proteins. Cell extracts were immunoprecipitated with anti-HA, and the immunoprecipitates were examined by Western blotting for eIF4E and HA-tagged proteins. No detectable FLAG-eIF4E was co-precipitated with p97 or with La, while eIF4G was able to precipitate FLAG-eIF4E.

To further substantiate these results, p97 or eIF4G was synthesized in vitro and mixed with bacterially expressed FLAG-eIF4E or FLAG-eIF4A bound to the anti-FLAG resin. Proteins bound to the anti-FLAG resin were eluted with the FLAG peptide. p97 and eIF4G specifically bound to eIF4A. In contrast, binding of p97 to eIF4E was not detectable, while interaction between eIF4G and eIF4E was evident. La failed to bind to either resin. We were not able to perform similar experiments for eIF3, since it consists of multi-subunits, and it is not known which subunit(s) interact(s) with eIF4G or p97. Thus, we conclude that p97 forms a protein complex which includes eIF4A and eIF3, but excludes eIF4E.

p97 Suppresses Cap-dependent and Cap-independent Translation

Ohlmann, T., et al., *EMBO J.* 15:1371–1382 (1996) showed that the C-terminal two thirds of eIF4G supports cap-independent translation. Based on its homology to eIF4G, p97 might also promote cap-independent translation. To explore this possibility, we expressed p97 and eIF4G in HeLa cells together with a reporter CAT (chloramphenicol acetyltransferase) mRNA, whose ORF is preceded by the encephalomyocarditis virus internal ribosome entry site (EMCV-IRES). Translation of EMCV-IRES-CAT mRNA was repressed 2 fold by expression of p97. In contrast, eIF4G stimulated cap-independent translation by 2 fold (these experiments were repeated 4 times with less than 10% variation between the results). Moreover, eIF4G relieved the p97-induced repression of translation, indicating that p97 inhibits cap-independent translation by competing with eIF4G. To study the effect of p97 on cap-dependent translation, CAT mRNA was used as the reporter. Similarly to its effect on cap-independent translation, p97 inhibited cap-dependent translation by 2 fold and the inhibition was partially relieved by co-expression of eIF4G.

To study how p97 expression affects overall protein synthesis in cells, we established a cell line that expresses p97 under a tetracycline-regulatable promoter (Beauparlant, P., et al., *J. Biol. Chem.* 271:10690–10696 (1996)). Withdrawal of tetracycline from the medium increased the amount of p97 about 4-fold without noticeable change of the amounts of eIF4G, eIF4E or eIF4A. Overexpression of p97 decreased the rate of protein synthesis by 20 to 25% as determined by incorporation of [$^3$H] leucine. We performed similar labeling experiments with [$^{35}$S] methionine and obtained essentially similar results (data not shown). These functional assays, combined with the binding results, suggest that p97 is a general suppressor of translation by forming a translationally inactive protein complex that includes eIF4A and eIF3, but excludes eIF4E.

Discussion

The present invention further provides a new translational regulator, p97, which is homologous to the C-terminal two thirds of eIF4G. This region of eIF4G contains binding sites for eIF4A and eIF3, while the binding site for eIF4E is present in the N-terminal third of the protein (Lamphear, B., et al., supra; Mader, S., et al., supra). p97 binds to eIF4A and eIF3, but not to eIF4E. While the C-terminal two thirds fragment of eIF4G is able to support translation initiation from the internal ribosome entry site (IRES) of hepatitis C virus and Theiler's murine encephalomyelitis virus (Ohlmann, T., et al., supra), p97 inhibits EMCV-IRES dependent translation. It is unlikely that the opposite effects on translation are due to different IRES elements, since poliovirus IRES-mediated translation is promoted by the C-terminus of eIF4G, while transient expression of p97 repressed translation of poliovirus IRES-CAT mRNA. Thus, it is likely that p97 generally inhibits IRES-dependent translation, while the C-terminal two thirds of eIF4G generally supports IRES-independent translation.

p97 most likely inhibits translation by sequestration of eIF4A and eIF3, thus keeping these proteins from interacting with eIF4G. eIF4A is absolutely required for cap-dependent and cap-independent translation (Pause, A., et al., supra) and eIF3 is essential for recruitment of ribosomes to mRNA (Pain, V. M., *Eur. J. Biochem.* 236:747–771 (1996)). p97 and eIF4G are likely to compete for eIF4A and eIF3 binding since, expression of eIF4G relieves p97-dependent repression of translation. This model of translational inhibition is reminiscent of the mechanism by which eIF4E-binding proteins inhibit translation. 4E-BP-1 competes with eIF4G for binding to eIF4E, and thereby inhibits formation of the complete eIF4F complex (Haghighat, A., et al., *EMBO J*. 14:5701–5709 (1995)). While 4E-BP-1 and eIF4E were reported to exist in reticulocyte lysate at an approximately 1:1 molar ratio (Rau, M., et al., *J. Biol. Chem.* 271:8983–8990 (1996)), the present inventors could not determine the molar ratio of p97 to other translation factors because of the difficulty in obtaining pure recombinant protein. The relative ratios of eIF4A, eIF4G (Duncan, R., et al., *J. Biol. Chem.* 262:380–388 (1987)) and eIF3 (Meyer, L. J., et al., supra; Mengod, G. & Trachsel, H. *Biochem. Biophys. Acta* 825:169–174 (1985)) to ribosomes in HeLa cells have been reported to be 3, 0.2 and 0.5, respectively.

Plants have two different eIF4F complexes. One is a complex of two polypeptides, p220 and p26, which are homologues of mammalian eIF4G and eIF4E. The other complex, called eIF(iso)4F, consists of p28, another homologue of mammalian eIF4E, and p82 (Browning, K. S., et al., *J. Biol. Chem.* 265:17967–17973 (1990); Allen, M., et al., *J. Biol. Chem.* 267:23232–23236 (1992)). p82 exhibits significant sequence similarity to human eIF4G (Allen, M., et al., supra), and the binding site for eIF4E is present in the N-terminus of p82 (Mader, S., et al., supra). eIF(iso)4F, like eIF4F, stimulates translation in vitro (Abramson et al., *J. Biol. Chem.* 263:5462–5467 (1988)). Yeast also has two genes encoding eIF4G homologues, TIF4631 and TIF4632 (Goyer, C., et al., *Mol. Cell. Biol.* 13:4860–4874 (1993)). Although both contain an eIF4E-binding site (Mader, S., et al., supra), there seems to be a functional difference between two proteins, since TIF4631-disrupted strains exhibited a slow-growth, cold sensitive phenotype, while disruption of TIF4632 failed to show any phenotype. Double gene disruption engendered lethality (Goyer, C., et al., *Mol. Cell. Biol.* 13:4860–4874 (1993)). It is possible that p97 has evolved from eIF4G to become a repressor by losing the binding site for eIF4E.

Why is GUG Employed Instead of AUG?

p97 mRNA has no initiator AUG and translation exclusively starts at a GUG codon. The nucleotide sequence surrounding the initiator GUG is GCCAAAGUGGAG (nucleotides 301–312 in FIGS. 2A–2E (SEQ ID NO:3)), which matches the consensus rule that purines are favorable at positions –3 and +4 (the first nucleotide of the initiation codon is defined as +1, shown herein as nucleotide 307 in FIGS. 2A–2E (SEQ ID NO:3)) (Kozak, M., *J. Cell. Biol.* 108:229–241 (1989)). More importantly, p97 mRNA has adenine at the +5 position. Translation starting at a non-AUG is efficient when the second codon is GAU, where G at +4 and A at +5 are more important than U at +6 (Boeck, R. & Kolakofsky, D. *EMBO J*. 13:3608–3617 (1994); Grunert, S. & Jackson, R., *EMBO J*. 13:3618–3630 (1994)).

Several important regulatory genes including c-myc (Hann, S. R., et al., *Cell* 52:185–195 (1988)), int-2 (Acland, P., et al., *Nature* 343:662–665 (1990)), pim-1, FGF-2 (Florkiewicz, R. Z. & Sommer, A., *Proc. Natl. Acad. Sci. USA* 86:3978–3981 (1989)) and WT-1 (Bruening, W. & Pelletier, J., *J. Biol. Chem.* 271:8446–8454 (1996)) have non-AUG initiators in addition to a downstream and in-frame AUG initiation codon, so that non-AUG initiated translation generates amino-terminally extended proteins. Some of the extended proteins show different intracellular localization than their shorter counterparts (Acland, P., et al., *Nature* 343:662–665 (1990); Bugler, B., et al., *Mol. Cell. Biol.* 11:573–577 (1991)). In contrast, multiple products are not produced from p97 mRNA, since the GUG is the only initiator. Translation initiation at CUG of c-Myc mRNA was enhanced, when culture medium was deprived of methionine (Hann, S. R., et al., *Genes & Dev.* 6:1229–1240 (1992)). For FGF-2, eIF4F seems to activate utilization of CUG more than that of AUG (Kevil, C., et al., *Oncogene* 11:2339–2348 (1996)). The expression of p97 might also be translationally controlled.

What is the Biological Significance of p97?

p97 is a putative modulator of interferon-γ-induced programmed cell death. Also, apoptosis has been shown to be affected by protein synthesis inhibitors (Martin, D. P., et al., *J. Cell Biol.* 106:829–844 (1988); Ledda-Columbano, G. M., et al., *Am. J. Pathol.* 140:545–549 (1992); Polunovsky, V. A., et al., *Exp. Cell Res.* 214:584–594 (1994)), and overexpression of eIF4E in NIH3T3 cells prevents apoptosis induced by serum depletion. Further, p97 mRNA is heavily edited, when apolipoprotein B mRNA-editing protein is overexpressed in the liver of transgenic mice, suggesting that the amount of p97 might be controlled by an editing mechanism.

EXAMPLE 3

Cloning and Expression of hPrt1 and p97 Proteins in a Baculovirus Expression System In this illustrative example, the plasmid shuttle vector pA2 GP is used to insert the cloned DNA encoding the hPrt1 and p97 proteins, both of which lack naturally associated secretory signal (leader) sequences, into a baculovirus to express the mature proteins, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the hPrt1 or p97 proteins in the deposited clones, containing the AUG initiation codon is amplified using PCR oligonucleotide primers corresponding to the 5' and 3' sequences of the gene.

The 5' primer for amplification of the hPrt1 coding sequence has the sequence:

5' GACT<u>TCTAGA</u>CCGCCATCATGCAGGACGCG GAGAACGTGGCG 3' (SEQ ID NO:7) containing the underlined XbaI restriction enzyme site followed by 24 bases of the sequence of the hPrt1 protein shown in FIGS. 1A–1D, beginning with the N-terminus of the protein. The 3' primer has the sequence:

5' GACTTCTAGAGGCGCAGGAGAAGGTGCCGCC 3' (SEQ ID NO:8) containing the underlined XbaI restriction site followed by 21 nucleotides complementary to the 3' noncoding sequence shown in FIGS. 1A–1D.

The 5' primer for amplification of the p97 coding sequence has the sequence:

5' GACTGGTACCGCCATCATGGAGAGTGCGATT GCAGAAGGG 3' (SEQ ID NO:9) containing the underlined Asp718 restriction enzyme site followed by 21 bases of the sequence of the p97 protein shown in FIGS. 2A–2E, beginning with the N-terminus of the protein. The 3' primer has the sequence:

5' GACTGGTACCCGCAGTGGTTAGGTCAAATGC 3' (SEQ ID NO:10) containing the underlined Asp718 restriction site followed by 21 nucleotides complementary to the 3' noncoding sequence shown in FIGS. 2A–2E.

The amplified fragment encoding either hPrt1 or p97 is isolated from a 1% agarose gel using a commercially available kit ("Geneclean," BIO 101 Inc., La Jolla, Calif.). The hPrt1 coding fragment then is digested with XbaI and the p97 coding fragment then is digested with Asp718. Each fragment is again is purified on a 1% agarose gel. These fragment are designated herein "F1".

The plasmid is digested with the restriction enzymes with either XbaI or Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB 101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with either the human hPrt1 or p97 gene using the PCR method, in which one of the primers that is used to amplify the gene and the second primer is from well within the vector so that only those bacterial colonies containing the hPrt1 or p97 gene fragment will show amplification of the DNA. The sequence of the cloned fragment is confirmed by DNA sequencing. These plasmids are designated herein pBac hPrt1 and pBac(p97).

Five µg of either pBac hPrt1 and pBac(p97) plasmid is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 µg of BaculoGold™ virus DNA and 5 µg of the plasmid are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculoviruslogy distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant viruses are called V-hPrt1 and V-p97.

To verify the expression of the hPrt1 and p97 genes, Sf9 cells are grown in Grace's medium supplemented with 10% heat inactivated FBS. The cells are infected with the recombinant baculovirus V-hPrt1 or V-p97 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

EXAMPLE 4

Cloning and Expression of hPrt1 and p97 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 4(a)

Cloning and Expression in COS Cells

The expression plasmids, phPrt1 HA and p(p97) HA, are made by cloning cDNAs encoding the hPrt1 and p97 proteins into the expression vector pcDNAI/Amp or pcDNAIII (which can be obtained from Invitrogen, Inc.).

The expression vector pcDNAIII contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) and a CMV promoter, a polylinker, an SV40 intron followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

With respect to the hPrt1 protein, a DNA fragment encoding the protein is cloned into the polylinker region of the vector so that recombinant protein expression is directed by the CMV promoter. The plasmid construction strategy is as follows. The hPrt1 cDNA of the deposited clone is amplified using primers that contain convenient restriction sites, much as described above for construction of vectors for expression of hPrt1 protein in *E. Coli*. Suitable primers include the following, which are used in this example. The 5' primer, containing the underlined XbaI site, a Kozak sequence, an AUG start codon and 7 additional codons of the 5' coding region of the complete hPrt1 protein has the following sequence:

5' GACT<u>TCTAGA</u>CCGCCATCATGCAGGACGCGGA GAACGTGGCG 3' (SEQ ID NO:7). The 3' primer, containing the underlined XbaI site, a stop codon, the HA tag sequence, and 19 bp of 3' coding sequence has the following sequence (at the 3' end):

5' GAC<u>TCTAGA</u>TTAAGCGTAGTCTGGGACGTCG ATGGGTAAA TCCCCCACTGCAGACAC 3' (SEQ ID NO:11).

Similarly, a DNA fragment encoding the p97 protein is cloned into the polylinker region of the same vector. The plasmid construction strategy is as follows. The p97 cDNA of the deposited clone is also amplified using primers that contain convenient restriction sites. Suitable primers include the following, which are used in this example. The 5' primer, containing the underlined Asp718 site, a Kozak sequence, an AUG start codon and 7 additional codons of the 5' coding region of the complete p97 protein has the following sequence:

5' GACT<u>GGTACC</u>GCCATCATGGAGAGTGCGATTG CAGAAGGG 3' (SEQ ID NO:9). The 3' primer, containing the underlined Asp718 site, a stop codon, the HA tag sequence, and 18 bp of 3' coding sequence has the following sequence (at the 3' end):

5' GAC<u>GGTACC</u>TTAAGCGTAGTCTGGGACGTCGT ATGGGTAGTC AGCTTCTTCCTCTGA 3' (SEQ ID NO:12).

The PCR amplified DNA fragments and the vector, pcDNAIII, are digested with XbaI for insertion of the hPrt1 coding sequences and Asp718 for insertion of the p97 coding sequences, and then ligated. The ligation mixture is transformed into *E. coli* strain SURE (available from Stratagene Cloning Systems, 11099 North Torrey Pines Road, La Jolla, Calif. 92037), and the—transformed culture is plated on ampicillin media plates which then are incubated to allow growth of ampicillin resistant colonies. Plasmid DNA is isolated from resistant colonies and examined by restriction analysis or other means for the presence of either the hPrt1 or p97 encoding fragment.

For expression of recombinant hPrt1 and p97, COS cells are transfected with an expression vector, as described above, using DEAE-DEXTRAN, as described, for instance, in Sambrook et al., *Molecular Cloning: a Laboratory Manual*, Cold Spring Laboratory Press (1989). Cells are incubated under conditions for expression of either hPrt1 or p97 by the vector.

Expression of the hPrt1-HA or p97-HA fusion proteins is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 4(b)

Cloning and Expression in CHO Cells

The vector pC4 is used for the expression of hPrt1 and p97 proteins. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J Biol. Chem.* 253:1357–1370, Hamlin, J. L. and Ma, C. 1990, Biochem. et *Biophys. Acta*, 1097:107–143, Page, M. J. and Sydenham, M. A. 1991, *Biotechnology* 9:64–68).

Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter is a BamHI restriction enzyme cleavage site that allows integration of the genes. Behind this cloning site the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the hPrt1 or p97 proteins in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes XbaI for insertion of the hPrt1 encoding fragment and Asp718 for insertion of the p97 encoding fragment. The vectors are then dephosphorylated using calf intestinal phosphatase by procedures known in the art. The vectors are then isolated from a 1% agarose gel.

The DNA sequence encoding the complete hPrt1 protein is amplified using PCR oligonucleotide primers corresponding to the 5' and 3' sequences of the gene. The 5' primer has the sequence:

5' GACT<u>TCTAGA</u>CCGCCATCATGCAGGACGCGG AGAACGTGGCG 3' (SEQ ID NO:7) containing the underlined XbaI restriction enzyme site followed by an efficient signal for initiation of translation in eukaryotes, as described by Kozak, M., *J. Mol. Biol.* 196:947–950 (1987), and 24 bases of the coding sequence of hPrt1 cDNA shown in FIGS. 1A–1D (SEQ ID NO:1). The 3' primer has the sequence:

5' GACT<u>TCTAGA</u>GGCGCAGGAGAAGGTGCCGCC 3' (SEQ ID NO:8) containing the underlined XbaI restriction site followed by 21 nucleotides complementary to the non-translated region of the hPrt1 gene shown in FIGS. 1A–1D (SEQ ID NO:1).

Similarly, the DNA sequence encoding the complete p97 protein is also amplified using PCR oligonucleotide primers corresponding to the 5' and 3' sequences of the gene. The 5' primer has the sequence:

5' GACT<u>GGTACC</u>GCCATCATGGAGAGTGCGATTG CAGAAGGG 3' (SEQ ID NO:9) containing the underlined Asp718 restriction enzyme site followed by an efficient signal for initiation of translation in eukaryotes, as described by Kozak, M., *J. Mol. Biol.* 196:947–950 (1987), and 24 bases of the coding sequence of p97 cDNA shown in FIGS. 2A–2E (SEQ ID NO:3). The 3' primer has the sequence:

5' GACT<u>GGTACC</u>CGCAGTGGTTAGGTCAAATGC 3' (SEQ ID NO:10) containing the underlined Asp718 restriction site followed by 21 nucleotides complementary to the non-translated region of the p97 gene shown in FIGS. 2A–2E (SEQ ID NO:3).

The amplified fragments are then digested with the endonucleases XbaI for insertion of the hPrt1 encoding fragment and Asp718 for insertion of the p97 encoding fragment and then purified again on a 1% agarose gel. The isolated fragments and the dephosphorylated vectors are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 µg of the expression plasmid pC4 is cotransfected with 0.5 µg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reverse phase HPLC analysis.

EXAMPLE 5

Tissue Distribution of hPrt1 and p97 mRNA Expression

Northern blot analysis is carried out to examine hPrt1 and p97 gene expression in human tissues, using methods described by, among others, Sambrook et al., cited above. A cDNA probe containing the entire nucleotide sequence of the hPrt1 (SEQ ID NO:1) or p97 (SEQ ID NO:3) protein is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for either hPrt1 or p97 mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

---

What is claimed is:

1. An isolated protein comprising an amino acid sequence at least 90% identical to amino acids 2 to 873 in SEQ ID NO:2.

2. The isolated protein of claim 1, comprising amino acids 2 to 873 in SEQ ID NO:2.

3. The isolated protein of claim 1, wherein said amino acid sequence is at least 95% identical to amino acids 2 to 873 in SEQ ID NO:2.

4. The isolated protein of claim 2, comprising amino acids 1 to 873 in SEQ ID NO:2.

5. The isolated protein of claim 1, which is produced by a recombinant host cell.

6. The isolated protein of claim 1, which comprises a heterologous polypeptide.

7. A composition comprising the isolated protein of claim 1 and a carrier.

8. An isolated protein comprising 15 contiguous amino acids of SEQ ID NO:2.

9. The isolated protein of claim 8, comprising 30 contiguous amino acids of SEQ ID NO:2.

10. The isolated protein of claim 9, comprising 50 contiguous amino acids of SEQ ID NO:2.

11. The isolated protein of claim 8, which is produced by a recombinant host cell.

12. The isolated protein of claim 8, which comprises a heterologous polypeptide.

13. A composition comprising the isolated protein of claim 8 and a carrier.

14. An isolated protein comprising 15 contiguous amino acids of the complete amino acid sequence encoded by the cDNA clone contained in ATCC Deposit No. 97766.

15. The isolated protein of claim 14, which comprises 30 contiguous amino acids of the complete amino acid sequence encoded by the cDNA clone contained in ATCC Deposit No. 97766.

16. The isolated protein of claim 15, which comprises 50 contiguous amino acids of the complete amino acid sequence encoded by the cDNA clone contained in ATCC Deposit No. 97766.

17. The isolated protein of claim 14, which is produced by a recombinant host cell.

18. The isolated protein of claim 14, which comprises a heterologous polypeptide.

19. A composition comprising the isolated protein of claim 14 and a carrier.

20. An isolated protein comprising amino acid residues encoded by a first polynucleotide which hybridizes to the cDNA clone contained in ATCC Deposit No.97766 under the following conditions:

(a) incubating overnight at 42° C. in a solution consisting of 50% formamide, 5×SSC, 50 mM sodium phosphate (pH 7.6), 5×Denhardt's solution, 10% dextran sulfate, and 20 µg/ml denatured, sheared salmon sperm DNA; and (b) washing at 65° C. in a solution consisting of 0.1×SSC; wherein said first polynucleotide encodes a protein having a biological activity selected from the group consisting of:

(a) binding affinity for the p170 subunit of eIF3; and (b) binding activity for an antibody having specificity for a polypeptide consisting of the complete amino acid sequence of SEQ ID NO:2.

21. The isolated protein of claim 20 which has binding affinity for the p170 subunit of eIF3.

22. The isolated protein of claim 20 which has binding activity for an antibody having specificity for a polypeptide consisting of the complete amino acid sequence of SEQ ID NO:2.

23. The isolated protein of claim 20, which is produced by a recombinant host cell.

24. The isolated protein of claim 20, which comprises a heterologous polypeptide.

25. A composition comprising the isolated protein of claim 20 and a carrier.

26. An isolated fragment of a protein comprising the amino acid sequence of SEQ ID NO:2, wherein said fragment has a biological activity selected from the group consisting of:

(a) binding affinity for the p170 subunit of eIF3; and (b) binding activity for an antibody having specificity for a polypeptide consisting of the complete amino acid sequence of SEQ ID NO:2.

27. The isolated fragment of claim 26 which has binding affinity for the p170 subunit of eIF3.

28. The isolated fragment of claim 26 which has binding activity for an antibody having specificity for a polypeptide consisting of the complete amino acid sequence of SEQ ID NO:2.

29. The isolated fragment of claim 26, which is produced by a recombinant host cell.

30. The isolated fragment of claim 26, which comprises a heterologous polypeptide.

31. A composition comprising the isolated fragment of claim 26 and a carrier.

32. An isolated protein comprising an amino acid sequence at least 90% identical to amino acids 2 to 873 in SEQ ID NO:2;
wherein said isolated protein has a biological activity selected from the group consisting of:
(i) binding affinity for the p170 subunit of eIF3; and
(ii) binding activity for an antibody having specificity for a polypeptide consisting of the complete amino acid sequence of SEQ ID NO:2.

33. The isolated protein of claim 32 which has binding affinity for the p170 subunit of eIF3.

34. The isolated protein of claim 32 which has binding activity for an antibody having specificity for a polypeptide consisting of the complete amino acid sequence of SEQ ID NO:2.

35. The isolated protein of claim 32, wherein said amino acid sequence is at least 95% identical to amino acids 2 to 873 in SEQ ID NO:2.

36. The isolated protein of claim 35 which has binding affinity for the p170 subunit of eIF3.

37. The isolated protein of claim 35 which has binding activity for an antibody having specificity for a polypeptide consisting of the complete amino acid sequence of SEQ ID NO:2.

38. The isolated protein of claim 32, which is produced by a recombinant host cell.

39. The isolated protein of claim 32, which comprises a heterologous polypeptide.

40. A composition comprising the isolated protein of claim 32 and a carrier.

41. An isolated protein comprising a first amino acid sequence which is at least 90% identical to a second amino acid sequence selected from the group consisting of:
(a) amino acids from 147 to 255 in SEQ ID NO:2; and
(b) amino acids from 185 to 270 in SEQ ID NO:2;
wherein said isolated protein has a biological activity selected from the group consisting of:
(i) binding affinity for the p170 subunit of eIF3; and
(ii) binding activity for an antibody having specificity for a polypeptide consisting of the complete amino acid sequence of SEQ ID NO:2.

42. The isolated protein of claim 41, comprising an amino acid sequence which is at least 90% identical to (a).

43. The isolated protein of claim 42 which has binding affinity for the p170 subunit of eIF3.

44. The isolated protein of claim 42 which has binding activity for an antibody having specificity for a polypeptide consisting of the complete amino acid sequence of SEQ ID NO:2.

45. The isolated protein of claim 41, comprising an amino acid sequence which is at least 90% identical to (b).

46. The isolated protein of claim 45 which has binding affinity for the p170 subunit of eIF3.

47. The isolated protein of claim 45 which has binding activity for an antibody having specificity for a polypeptide consisting of the complete amino acid sequence of SEQ ID NO:2.

48. The isolated protein of claim 42, comprising an amino acid sequence which is at least 95% identical to (a).

49. The isolated protein of claim 48 which has binding affinity for the p170 subunit of eIF3.

50. The isolated protein of claim 48 which has binding activity for an antibody having specificity for a polypeptide consisting of the complete amino acid sequence of SEQ ID NO:2.

51. The isolated protein of claim 45, comprising an amino acid sequence which is at least 95% identical to (b).

52. The isolated protein of claim 51 which has binding affinity for the p170 subunit of eIF3.

53. The isolated protein of claim 51 which has binding activity for an antibody having specificity for a polypeptide consisting of the complete amino acid sequence of SEQ ID NO:2.

54. The isolated protein of claim 41, which is produced by a recombinant host cell.

55. The isolated protein of claim 41, which comprises a heterologous polypeptide.

56. A composition comprising the isolated protein of claim 41 and a carrier.

57. An isolated protein comprising a first amino acid sequence which is at least 90% identical to a second amino acid sequence selected from the group consisting of:
(a) amino acids 1 to 188 of SEQ ID NO:2;
(b) amino acids 193 to 235 of SEQ ID NO:2;
(c) amino acids 248 to 262 of SEQ ID NO:2; and
(d) amino acids 270 to 350 of SEQ ID NO:2;
wherein said isolated protein has a biological activity selected from the group consisting of:
(i) binding affinity for the p170 subunit of eIF3; and
(ii) binding activity for an antibody having specificity for a polypeptide consisting of the complete amino acid sequence of SEQ ID NO:2.

58. The isolated protein of claim 57, comprising an amino acid sequence which is at least 90% identical to (a).

59. The isolated protein of claim 58 which has binding affinity for the p170 subunit of eIF3.

60. The isolated protein of claim 58 which has binding activity for an antibody having specificity for a polypeptide consisting of the complete amino acid sequence of SEQ ID NO:2.

61. The isolated protein of claim 57, comprising an amino acid sequence which is at least 90% identical to (b).

62. The isolated protein of claim 61 which has binding affinity for the p170 subunit of eIF3.

63. The isolated protein of claim 61 which has binding activity for an antibody having specificity for a polypeptide consisting of the complete amino acid sequence of SEQ ID NO:2.

64. The isolated protein of claim 57, comprising an amino acid sequence which is at least 90% identical to (c).

65. The isolated protein of claim 64 which has binding affinity for the p170 subunit of eIF3.

66. The isolated protein of claim 64 which has binding activity for an antibody having specificity for a polypeptide consisting of the complete amino acid sequence of SEQ ID NO:2.

67. The isolated protein of claim 57, comprising an amino acid sequence which is at least 90% identical to (d).

68. The isolated protein of claim 67 which has binding affinity for the p170 subunit of eIF3.

69. The isolated protein of claim 67 which has binding activity for an antibody having specificity for a polypeptide consisting of the complete amino acid sequence of SEQ ID NO:2.

70. The isolated protein of claim 58, comprising an amino acid sequence which is at least 95% identical to (a).

71. The isolated protein of claim 70 which has binding affinity for the p170 subunit of eIF3.

72. The isolated protein of claim 70 which has binding activity for an antibody having specificity for a polypeptide consisting of the complete amino acid sequence of SEQ ID NO:2.

73. The isolated protein of claim 61, comprising an amino acid sequence which is at least 95% identical to (b).

74. The isolated protein of claim 73 which has binding affinity for the p170 subunit of eIF3.

75. The isolated protein of claim 73 which has binding activity for an antibody having specificity for a polypeptide consisting of the complete amino acid sequence of SEQ ID NO:2.

76. The isolated protein of claim 64, comprising an amino acid sequence which is at least 95% identical to (c).

77. The isolated protein of claim 76 which has binding affinity for the p170 subunit of eIF3.

78. The isolated protein of claim 76 which has binding activity for an antibody having specificity for a polypeptide consisting of the complete amino acid sequence of SEQ ID NO:2.

79. The isolated protein of claim 67, comprising an amino acid sequence which is at least 95% identical to (d).

80. The isolated protein of claim 79 which has binding affinity for the p170 subunit of eIF3.

81. The isolated protein of claim 79 which has binding activity for an antibody having specificity for a polypeptide consisting of the complete amino acid sequence of SEQ ID NO:2.

82. The isolated protein of claim 57, which is produced by a recombinant host cell.

83. The isolated protein of claim 57, which comprises a heterologous polypeptide.

84. A composition comprising the isolated protein of claim 57 and a carrier.

85. An isolated protein comprising a first amino acid sequence which is at least 90% identical to a second amino acid sequence selected from the group consisting of:
  (a) amino acids 361 to 449 of SEQ ID NO:2;
  (b) amino acids 458 to 620 of SEQ ID NO:2; and
  (c) amino acids 639 to 846 of SEQ ID NO:2;
  wherein said isolated protein has a biological activity selected from the group consisting of:
    (i) binding affinity for the p170 subunit of eIF3; and
    (ii) binding activity for an antibody having specificity for a polypeptide consisting of the complete amino acid sequence of SEQ ID NO:2.

86. The isolated protein of claim 85, comprising an amino acid sequence which is at least 90% identical to (a).

87. The isolated protein of claim 86 which has binding affinity for the p170 subunit of eIF3.

88. The isolated protein of claim 86 which has binding activity for an antibody having specificity for a polypeptide consisting of the complete amino acid sequence of SEQ ID NO:2.

89. The isolated protein of claim 85, comprising an amino acid sequence which is at least 90% identical to (b).

90. The isolated protein of claim 89 which has binding affinity for the p170 subunit of eIF3.

91. The isolated protein of claim 89 which has binding activity for an antibody having specificity for a polypeptide consisting of the complete amino acid sequence of SEQ ID NO:2.

92. The isolated protein of claim 85, comprising an amino acid sequence which is at least 90% identical to (c).

93. The isolated protein of claim 92 which has binding affinity for the p170 subunit of eIF3.

94. The isolated protein of claim 92 which has binding activity for an antibody having specificity for a polypeptide consisting of the complete amino acid sequence of SEQ ID NO:2.

95. The isolated protein of claim 86, comprising an amino acid sequence which is at least 95% identical to (a).

96. The isolated protein of claim 95 which has binding affinity for the p170 subunit of eIF3.

97. The isolated protein of claim 95 which has binding activity for an antibody having specificity for a polypeptide consisting of the complete amino acid sequence of SEQ ID NO:2.

98. The isolated protein of claim 89, comprising an amino acid sequence which is at least 95% identical to (b).

99. The isolated protein of claim 98 which has binding affinity for the p170 subunit of eIF3.

100. The isolated protein of claim 98 which has binding activity for an antibody having specificity for a polypeptide consisting of the complete amino acid sequence of SEQ ID NO:2.

101. The isolated protein of claim 92, comprising an amino acid sequence which is at least 95% identical to (c).

102. The isolated protein of claim 101 which has binding affinity for the p170 subunit of eIF3.

103. The isolated protein of claim 101 which has binding activity for an antibody having specificity for a polypeptide consisting of the complete amino acid sequence of SEQ ID NO:2.

104. The isolated protein of claim 85, which is produced by a recombinant host cell.

105. The isolated protein of claim 85, which comprises a heterologous polypeptide.

106. A composition comprising the isolated protein of claim 85 and a carrier.

107. An isolated protein comprising an amino acid sequence at least 90% identical to the complete amino acid sequence encoded by the cDNA clone contained in ATCC Deposit No. 97766.

108. The isolated protein of claim 107, comprising an amino acid sequence at least 95% identical to the complete amino acid sequence encoded by the cDNA clone contained in ATCC Deposit No. 97766.

109. The isolated protein of claim 107, comprising the complete amino acid sequence encoded by the cDNA clone contained in ATCC Deposit No. 97766.

110. The isolated protein of claim 107, which is produced by a recombinant host cell.

111. The isolated protein of claim 107, which comprises a heterologous polypeptide.

112. A composition comprising the isolated protein of claim 107 and a carrier.

113. An isolated protein comprising a first amino acid sequence which is at least 90% identical to a second amino acid sequence selected from the group consisting of:
  (a) amino acids from 147 to 255 in SEQ ID NO:2; and
  (b) amino acids from 185 to 270 in SEQ ID NO:2.

114. The isolated protein of claim 113, comprising an amino acid sequence which is at least 90% identical to (a).

115. The isolated protein of claim 114, comprising an amino acid sequence which is at least 95% identical to (a).

116. The isolated protein of claim 115, wherein said amino acid sequence is (a).

117. The isolated protein of claim 113, comprising an amino acid sequence which is at least 90% identical to (b).

118. The isolated protein of claim 117, comprising an amino acid sequence which is at least 95% identical to (b).

119. The isolated protein of claim 118, wherein said amino acid sequence is (b).

120. The isolated protein of claim 113, which is produced by a recombinant host cell.

121. The isolated protein of claim 113, which comprises a heterologous polypeptide.

122. A composition comprising the isolated protein of claim 113 and a carrier.

123. An isolated protein comprising a first amino acid sequence which is at least 90% identical to a second amino acid sequence selected from the group consisting of:

(a) amino acids 1 to 188 of SEQ ID NO:2;

(b) amino acids 193 to 235 of SEQ ID NO:2;

(c) amino acids 248 to 262 of SEQ ID NO:2; and (d) amino acids 270 to 350 of SEQ ID NO:2.

124. The isolated protein of claim 123, comprising an amino acid sequence which is at least 90% identical to (a).

125. The isolated protein of claim 124, comprising an amino acid sequence which is at least 95% identical to (a).

126. The isolated protein of claim 125, wherein said amino acid sequence is (a).

127. The isolated protein of claim 123, comprising an amino acid sequence which is at least 90% identical to (b).

128. The isolated protein of claim 127, comprising an amino acid sequence which is at least 95% identical to (b).

129. The isolated protein of claim 128, wherein said amino acid sequence is (b).

130. The isolated protein of claim 123, comprising an amino acid sequence which is at least 90% identical to (c).

131. The isolated protein of claim 130, comprising an amino acid sequence which is at least 95% identical to (c).

132. The isolated protein of claim 131, wherein said amino acid sequence is (c).

133. The isolated protein of claim 123, comprising an amino acid sequence which is at least 90% identical to (d).

134. The isolated protein of claim 133, comprising an amino acid sequence which is at least 95% identical to (d).

135. The isolated protein of claim 134, wherein said amino acid sequence is (d).

136. The isolated protein of claim 123, which is produced by a recombinant host cell.

137. The isolated protein of claim 123, which comprises a heterologous polypeptide.

138. A composition comprising the isolated protein of claim 123 and a carrier.

139. An isolated protein comprising a first amino acid sequence which is at least 90% identical to a second amino acid sequence selected from the group consisting of:

(a) amino acids 361 to 449 of SEQ ID NO:2;

(b) amino acids 458 to 620 of SEQ ID NO:2; and (c) amino acids 639 to 846 of SEQ ID NO:2.

140. The isolated protein of claim 139, comprising an amino acid sequence which is at least 90% identical to (a).

141. The isolated protein of claim 140, comprising an amino acid sequence which is at least 95% identical to (a).

142. The isolated protein of claim 141, wherein said amino acid sequence is (a).

143. The isolated protein of claim 139, comprising an amino acid sequence which is at least 90% identical to (b).

144. The isolated protein of claim 143, comprising an amino acid sequence which is at least 95% identical to (b).

145. The isolated protein of claim 144, wherein said amino acid sequence is (b).

146. The isolated protein of claim 139, comprising an amino acid sequence which is at least 90% identical to (c).

147. The isolated protein of claim 146, comprising an amino acid sequence which is at least 95% identical to (c).

148. The isolated protein of claim 147, wherein said amino acid sequence is (c).

149. The isolated protein of claim 139, which is produced by a recombinant host cell.

150. The isolated protein of claim 139, which comprises a heterologous polypeptide.

151. A composition comprising the isolated protein of claim 139 and a carrier.

\* \* \* \* \*

UNITED STATES PATENT AND TRADEMARK OFFICE
CERTIFICATE OF CORRECTION

PATENT NO. : 6,093,795

DATED : July 25, 2000

INVENTORS : OLSEN et al.

It is certified that an error appears in the above-identified patent and that said Letters Patent is hereby corrected as shown below.

At column 6, line 57, delete "Mg/ml," and insert therefor --µg/ml--.

Signed and Sealed this

First Day of May, 2001

*Attest:*

NICHOLAS P. GODICI

*Attesting Officer*     *Acting Director of the United States Patent and Trademark Office*

SEQUENCE LISTING

<160> NUMBER OF SEQ ID NOS: 13

<210> SEQ ID NO 1
<211> LENGTH: 3032
<212> TYPE: DNA
<213> ORGANISM: Homo sapiens
<220> FEATURE:
<221> NAME/KEY: CDS
<222> LOCATION: (97)..(2718)

<400> SEQUENCE: 1

```
ccctcgagtc gacggtatcg ataagcttat cgataccgtc gactgctacc gaaggccggc      60
ggccgcggag ccctgcgagt aggcagcgtt gggccc atg cag gac gcg gag aac       114
                                       Met Gln Asp Ala Glu Asn
                                         1               5 gtg gcg gtg ccc gag gcg gcc gag gag cgc gcc gag ccc ggc cag cag       162
Val Ala Val Pro Glu Ala Ala Glu Glu Arg Ala Glu Pro Gly Gln Gln
             10                  15                  20 cag ccg gcc gcc gag ccg ccg cca gcc gag ggg ctg ctg cgg ccc gcg       210
Gln Pro Ala Ala Glu Pro Pro Pro Ala Glu Gly Leu Leu Arg Pro Ala
         25                  30                  35 ggg ccc ggc gct ccg gag gcc gcg ggg acc gag gcc tcc agt gag gag       258
Gly Pro Gly Ala Pro Glu Ala Ala Gly Thr Glu Ala Ser Ser Glu Glu
     40                  45                  50 gtg ggg atc gcg gag gcc ggg ccg gag ccc gag gtg agg acc gag ccg       306
Val Gly Ile Ala Glu Ala Gly Pro Glu Pro Glu Val Arg Thr Glu Pro
 55                  60                  65                  70 gcg gcc gag gca gag gcg gcc tcc ggc ccg tcc gag tcg ccc tcg ccg       354
Ala Ala Glu Ala Glu Ala Ala Ser Gly Pro Ser Glu Ser Pro Ser Pro
                 75                  80                  85 ccg gcc gcc gag gag ctg ccc ggg tcg cat gct gag ccc cct gtc ccg       402
Pro Ala Ala Glu Glu Leu Pro Gly Ser His Ala Glu Pro Pro Val Pro
             90                  95                 100 gca cag ggc gag gcc cca gga gag cag gct cgg gac gca ggc tcc gac       450
Ala Gln Gly Glu Ala Pro Gly Glu Gln Ala Arg Asp Ala Gly Ser Asp
        105                 110                 115 agc cgg gcc cag gcg gtg tcc gag gac gcg gga gga aac gag ggc aga       498
Ser Arg Ala Gln Ala Val Ser Glu Asp Ala Gly Gly Asn Glu Gly Arg
    120                 125                 130 gcg gcc gag gcc gaa ccc cgg gcg ctg gag aac ggc gac gcg gac gag       546
Ala Ala Glu Ala Glu Pro Arg Ala Leu Glu Asn Gly Asp Ala Asp Glu
135                 140                 145                 150 ccc tcc ttc agc gac ccc gag gac ttc gtg gac gac gtg agc gag gaa       594
Pro Ser Phe Ser Asp Pro Glu Asp Phe Val Asp Asp Val Ser Glu Glu
                155                 160                 165 gaa tta ctg gga gat gta ctc aaa gat cgg ccc cag gaa gca gat gga       642
Glu Leu Leu Gly Asp Val Leu Lys Asp Arg Pro Gln Glu Ala Asp Gly
            170                 175                 180 atc gat tcg gtg att gta gtg gac aat gtc cct cag gtg gga ccc gac       690
Ile Asp Ser Val Ile Val Val Asp Asn Val Pro Gln Val Gly Pro Asp
        185                 190                 195 cga ctt gag aaa ctc aaa aat gtc atc cac aag atc ttt tcc aag ttt       738
Arg Leu Glu Lys Leu Lys Asn Val Ile His Lys Ile Phe Ser Lys Phe
    200                 205                 210
```

-continued

| | | |
|---|---|---|
| ggg aaa atc aca aat gat ttt tat cct gaa gag gat ggg aag aca aaa<br>Gly Lys Ile Thr Asn Asp Phe Tyr Pro Glu Glu Asp Gly Lys Thr Lys<br>215                     220                    225                   230 | | 786 |
| ggg tat att ttc ctg gag tac gcg tcc cct gcc cac gct gtg gat gct<br>Gly Tyr Ile Phe Leu Glu Tyr Ala Ser Pro Ala His Ala Val Asp Ala<br>                   235                    240                    245 | | 834 |
| gtg aag aac gcc gac ggc tac aag ctt gac aag cag cac aca ttc cgg<br>Val Lys Asn Ala Asp Gly Tyr Lys Leu Asp Lys Gln His Thr Phe Arg<br>           250                    255                    260 | | 882 |
| gtc aac ctc ttt acg gat ttt gac aag tat atg acg atc agt gac gag<br>Val Asn Leu Phe Thr Asp Phe Asp Lys Tyr Met Thr Ile Ser Asp Glu<br>           265                    270                    275 | | 930 |
| tgg gat att cca gag aaa cag cct ttc aaa gac ctg ggg aac tta cgt<br>Trp Asp Ile Pro Glu Lys Gln Pro Phe Lys Asp Leu Gly Asn Leu Arg<br>280                     285                    290 | | 978 |
| tac tgg ctt gaa gag gca gaa tgc aga gat cag tac agt gtg att ttt<br>Tyr Trp Leu Glu Glu Ala Glu Cys Arg Asp Gln Tyr Ser Val Ile Phe<br>295                     300                    305                   310 | | 1026 |
| gag agt gga gac cgc act tcc ata ttc tgg aat gac gta aaa gac cct<br>Glu Ser Gly Asp Arg Thr Ser Ile Phe Trp Asn Asp Val Lys Asp Pro<br>                   315                    320                    325 | | 1074 |
| gtc tca att gaa gaa aga gcg aga tgg aca gag acg tat gtg cgt tgg<br>Val Ser Ile Glu Glu Arg Ala Arg Trp Thr Glu Thr Tyr Val Arg Trp<br>           330                    335                    340 | | 1122 |
| tct cct aag ggc acc tac ctg gct acc ttt cat caa aga ggc att gct<br>Ser Pro Lys Gly Thr Tyr Leu Ala Thr Phe His Gln Arg Gly Ile Ala<br>345                     350                    355 | | 1170 |
| cta tgg gga gag aaa ttc aag caa att cag aga ttc agc cac caa<br>Leu Trp Gly Gly Glu Lys Phe Lys Gln Ile Gln Arg Phe Ser His Gln<br>360                     365                    370 | | 1218 |
| ggg gtt cag ctt att gac ttc tca cct tgt gaa agg tac ctg gtg acc<br>Gly Val Gln Leu Ile Asp Phe Ser Pro Cys Glu Arg Tyr Leu Val Thr<br>375                     380                    385                   390 | | 1266 |
| ttt agc ccc ctg atg gac acg cag gat gac cct cag gcc ata atc atc<br>Phe Ser Pro Leu Met Asp Thr Gln Asp Asp Pro Gln Ala Ile Ile Ile<br>                   395                    400                    405 | | 1314 |
| tgg gac atc ctt acg ggg cac aag aag agg ggt ttt cac tgt gag agc<br>Trp Asp Ile Leu Thr Gly His Lys Lys Arg Gly Phe His Cys Glu Ser<br>           410                    415                    420 | | 1362 |
| tca gcc cat tgg cct att ttt aag tgg agc cat gat ggc aaa ttc ttt<br>Ser Ala His Trp Pro Ile Phe Lys Trp Ser His Asp Gly Lys Phe Phe<br>425                     430                    435 | | 1410 |
| gcc aga atg acc ctg gat acg ctt agc atc tat gaa act cct tct atg<br>Ala Arg Met Thr Leu Asp Thr Leu Ser Ile Tyr Glu Thr Pro Ser Met<br>440                     445                    450 | | 1458 |
| ggt ctt ttg gac aag aag agt ttg aag atc tct ggg ata aaa gac ttt<br>Gly Leu Leu Asp Lys Lys Ser Leu Lys Ile Ser Gly Ile Lys Asp Phe<br>455                     460                    465                   470 | | 1506 |
| tct tgg tct cct ggt ggt aac ata atc gcc ttc tgg gtg cct gaa gac<br>Ser Trp Ser Pro Gly Gly Asn Ile Ile Ala Phe Trp Val Pro Glu Asp<br>                   475                    480                    485 | | 1554 |
| aaa gat att cca gcc agg gta acc ctg atg cag ctc cct acc agg caa<br>Lys Asp Ile Pro Ala Arg Val Thr Leu Met Gln Leu Pro Thr Arg Gln<br>           490                    495                    500 | | 1602 |
| gag atc cga gtg agg aac ctg ttc aat gtg gtg gac tgc aag ctc cat<br>Glu Ile Arg Val Arg Asn Leu Phe Asn Val Val Asp Cys Lys Leu His<br>                 505                    510                    515 | | 1650 |
| tgg cag aag aac gga gac tac ttg tgt gtg aaa gta gat agg act ccg<br>Trp Gln Lys Asn Gly Asp Tyr Leu Cys Val Lys Val Asp Arg Thr Pro<br>520                     525                    530 | | 1698 |

-continued

| | | |
|---|---|---|
| aaa ggc acc cag ggt gtt gtc aca aat ttt gaa att ttc cga atg agg<br>Lys Gly Thr Gln Gly Val Val Thr Asn Phe Glu Ile Phe Arg Met Arg<br>535     540     545     550 | 1746 |
| gag aaa cag gta cct gtg gat gtg gtc gag atg aaa gaa acc atc ata<br>Glu Lys Gln Val Pro Val Asp Val Val Glu Met Lys Glu Thr Ile Ile<br>     555     560     565 | 1794 |
| gcc ttt gcc tgg gaa cca aat gga agt aag ttt gct gtg ctg cac gga<br>Ala Phe Ala Trp Glu Pro Asn Gly Ser Lys Phe Ala Val Leu His Gly<br>  570     575     580 | 1842 |
| gag gct ccg cgg ata tct gtg tct ttc tac cac gtc aaa aac aac ggg<br>Glu Ala Pro Arg Ile Ser Val Ser Phe Tyr His Val Lys Asn Asn Gly<br>585     590     595 | 1890 |
| aag att gaa ctc atc aag atg ttc gac aag cag cag gcg aac acc atc<br>Lys Ile Glu Leu Ile Lys Met Phe Asp Lys Gln Gln Ala Asn Thr Ile<br>     600     605     610 | 1938 |
| ttc tgg agc ccc caa gga cag ttc gtg gtg ttg gcg ggc ctg agg agt<br>Phe Trp Ser Pro Gln Gly Gln Phe Val Val Leu Ala Gly Leu Arg Ser<br>615     620     625     630 | 1986 |
| atg aac ggt gcc tta gcg ttt gtg gac act tcg gac tgc acg gtc atg<br>Met Asn Gly Ala Leu Ala Phe Val Asp Thr Ser Asp Cys Thr Val Met<br>     635     640     645 | 2034 |
| aac atc gca gag cac tac atg gct tcc gac gtc gaa tgg gat cct act<br>Asn Ile Ala Glu His Tyr Met Ala Ser Asp Val Glu Trp Asp Pro Thr<br>  650     655     660 | 2082 |
| ggg cgc tac gtc gtc acc tct gtg tcc tgg tgg agc cat aag gtg gac<br>Gly Arg Tyr Val Val Thr Ser Val Ser Trp Trp Ser His Lys Val Asp<br>665     670     675 | 2130 |
| aac gcg tac tgg ctg tgg act ttc cag gga cgc ctc ctg cag aag aac<br>Asn Ala Tyr Trp Leu Trp Thr Phe Gln Gly Arg Leu Leu Gln Lys Asn<br>  680     685     690 | 2178 |
| aac aag gac cgc ttc tgc cag ctg ctg tgg cgg ccc cgg cct ccc aca<br>Asn Lys Asp Arg Phe Cys Gln Leu Leu Trp Arg Pro Arg Pro Pro Thr<br>695     700     705     710 | 2226 |
| ctc ctg agc cag gaa cag atc aag caa att aaa aag gat ctg aag aaa<br>Leu Leu Ser Gln Glu Gln Ile Lys Gln Ile Lys Lys Asp Leu Lys Lys<br>     715     720     725 | 2274 |
| tac tct aag atc ttt gaa cag aag gat cgt ttg agt cag tcc aaa gcc<br>Tyr Ser Lys Ile Phe Glu Gln Lys Asp Arg Leu Ser Gln Ser Lys Ala<br>  730     735     740 | 2322 |
| tca aag gaa ttg gtg gag aga agg cgc acc atg atg gaa gat ttc cgg<br>Ser Lys Glu Leu Val Glu Arg Arg Arg Thr Met Met Glu Asp Phe Arg<br>745     750     755 | 2370 |
| aag tac cgg aaa atg gcc cag gag ctc tat atg gag cag aaa aac gag<br>Lys Tyr Arg Lys Met Ala Gln Glu Leu Tyr Met Glu Gln Lys Asn Glu<br>  760     765     770 | 2418 |
| cgc ctg gag ttg cga gga ggg gtg gac act gac gag ctg gac agc aac<br>Arg Leu Glu Leu Arg Gly Gly Val Asp Thr Asp Glu Leu Asp Ser Asn<br>775     780     785     790 | 2466 |
| gtg gac gac tgg gaa gag gag acc att gag ttc ttc gtc act gaa gaa<br>Val Asp Asp Trp Glu Glu Glu Thr Ile Glu Phe Phe Val Thr Glu Glu<br>     795     800     805 | 2514 |
| atc att ccc ctc gga atc agg agt gac ctg gag cac tgt gcg cag ccg<br>Ile Ile Pro Leu Gly Ile Arg Ser Asp Leu Glu His Cys Ala Gln Pro<br>  810     815     820 | 2562 |
| tgt gtg ctg tgg agc cga ggc cgt cct gca gga agc cgc gtg act ccc<br>Cys Val Leu Trp Ser Arg Gly Arg Pro Ala Gly Ser Arg Val Thr Pro<br>825     830     835 | 2610 |
| gcc tcc tcc ctg tgc tct ctg gct ctg gac tgt gac tgc gcc tgg att<br>Ala Ser Ser Leu Cys Ser Leu Ala Leu Asp Cys Asp Cys Ala Trp Ile<br>  840     845     850 | 2658 |

```
ctg cca ttg cga cac att ttt gtg cct ttc agc ccc tgg tgt ctg cag    2706
Leu Pro Leu Arg His Ile Phe Val Pro Phe Ser Pro Trp Cys Leu Gln
855                 860                 865                 870 tgg ggg att taa ggcacccgct tccacttctt tcttgtttgg agttttctgt        2758
Trp Gly Ile tggaaccgcc ggcgttggct ccgaagactt agcgacgcac tggcggcacc ttctcctgcg  2818
cccagtgatg tttccacggt gcctgtacac agccgagcag catttccgtt gaaggacttg  2878
catccccatt gcgggcagtg ctggacgtgt cccggagacc caccggaggg cgccgcatgc  2938
cttgtacccc caccgtgcag gttgtggccg gttttctccg caggttgaac atggaaataa  2998
aagcaaactt gtatgaaaaa aaaaaaaaaa aaaa                              3032

<210> SEQ ID NO 2
<211> LENGTH: 873
<212> TYPE: PRT
<213> ORGANISM: Homo sapiens

<400> SEQUENCE: 2

Met Gln Asp Ala Glu Asn Val Ala Val Pro Glu Ala Ala Glu Arg
  1               5                  10                  15

Ala Glu Pro Gly Gln Gln Gln Pro Ala Ala Glu Pro Pro Ala Glu
                 20                  25                  30

Gly Leu Leu Arg Pro Ala Gly Pro Gly Ala Pro Glu Ala Ala Gly Thr
                 35                  40                  45

Glu Ala Ser Ser Glu Glu Val Gly Ile Ala Glu Ala Gly Pro Glu Pro
 50                  55                  60

Glu Val Arg Thr Glu Pro Ala Ala Glu Ala Glu Ala Ala Ser Gly Pro
 65                  70                  75                  80

Ser Glu Ser Pro Ser Pro Pro Ala Ala Glu Glu Leu Pro Gly Ser His
                 85                  90                  95

Ala Glu Pro Pro Val Pro Ala Gln Gly Glu Ala Pro Gly Glu Gln Ala
                100                 105                 110

Arg Asp Ala Gly Ser Asp Ser Arg Ala Gln Ala Val Ser Glu Asp Ala
                115                 120                 125

Gly Gly Asn Glu Gly Arg Ala Ala Glu Ala Glu Pro Arg Ala Leu Glu
    130                 135                 140

Asn Gly Asp Ala Asp Glu Pro Ser Phe Ser Asp Pro Glu Asp Phe Val
145                 150                 155                 160

Asp Asp Val Ser Glu Glu Leu Leu Gly Asp Val Leu Lys Asp Arg
                165                 170                 175

Pro Gln Glu Ala Asp Gly Ile Ser Ser Val Ile Val Asp Asn Val
                180                 185                 190

Pro Gln Val Gly Pro Asp Arg Leu Glu Lys Leu Lys Asn Val Ile His
                195                 200                 205

Lys Ile Phe Ser Lys Phe Gly Lys Ile Thr Asn Asp Phe Tyr Pro Glu
    210                 215                 220

Glu Asp Gly Lys Thr Lys Gly Tyr Ile Phe Leu Glu Tyr Ala Ser Pro
225                 230                 235                 240

Ala His Ala Val Asp Ala Val Lys Asn Ala Asp Gly Tyr Lys Leu Asp
                245                 250                 255

Lys Gln His Thr Phe Arg Val Asn Leu Phe Thr Asp Phe Asp Lys Tyr
                260                 265                 270

Met Thr Ile Ser Asp Glu Trp Asp Ile Pro Glu Lys Gln Pro Phe Lys
    275                 280                 285
```

```
Asp Leu Gly Asn Leu Arg Tyr Trp Leu Glu Ala Glu Cys Arg Asp
290                 295                 300

Gln Tyr Ser Val Ile Phe Glu Ser Gly Asp Arg Thr Ser Ile Phe Trp
305                 310                 315                 320

Asn Asp Val Lys Asp Pro Val Ser Ile Glu Glu Arg Ala Arg Trp Thr
                325                 330                 335

Glu Thr Tyr Val Arg Trp Ser Pro Lys Gly Thr Tyr Leu Ala Thr Phe
            340                 345                 350

His Gln Arg Gly Ile Ala Leu Trp Gly Gly Glu Lys Phe Lys Gln Ile
        355                 360                 365

Gln Arg Phe Ser His Gln Gly Val Gln Leu Ile Asp Phe Ser Pro Cys
370                 375                 380

Glu Arg Tyr Leu Val Thr Phe Ser Pro Leu Met Asp Thr Gln Asp Asp
385                 390                 395                 400

Pro Gln Ala Ile Ile Ile Trp Asp Ile Leu Thr Gly His Lys Lys Arg
                405                 410                 415

Gly Phe His Cys Glu Ser Ser Ala His Trp Pro Ile Phe Lys Trp Ser
            420                 425                 430

His Asp Gly Lys Phe Phe Ala Arg Met Thr Leu Asp Thr Leu Ser Ile
        435                 440                 445

Tyr Glu Thr Pro Ser Met Gly Leu Leu Asp Lys Ser Leu Lys Ile
450                 455                 460

Ser Gly Ile Lys Asp Phe Ser Trp Ser Pro Gly Gly Asn Ile Ile Ala
465                 470                 475                 480

Phe Trp Val Pro Glu Asp Lys Asp Ile Pro Ala Arg Val Thr Leu Met
                485                 490                 495

Gln Leu Pro Thr Arg Gln Glu Ile Arg Val Arg Asn Leu Phe Asn Val
            500                 505                 510

Val Asp Cys Lys Leu His Trp Gln Lys Asn Gly Asp Tyr Leu Cys Val
        515                 520                 525

Lys Val Asp Arg Thr Pro Lys Gly Thr Gln Gly Val Val Thr Asn Phe
530                 535                 540

Glu Ile Phe Arg Met Arg Glu Lys Gln Val Pro Val Asp Val Val Glu
545                 550                 555                 560

Met Lys Glu Thr Ile Ile Ala Phe Ala Trp Glu Pro Asn Gly Ser Lys
                565                 570                 575

Phe Ala Val Leu His Gly Glu Ala Pro Arg Ile Ser Val Ser Phe Tyr
            580                 585                 590

His Val Lys Asn Asn Gly Lys Ile Glu Leu Ile Lys Met Phe Asp Lys
        595                 600                 605

Gln Gln Ala Asn Thr Ile Phe Trp Ser Pro Gln Gly Gln Phe Val Val
610                 615                 620

Leu Ala Gly Leu Arg Ser Met Asn Gly Ala Leu Ala Phe Val Asp Thr
625                 630                 635                 640

Ser Asp Cys Thr Val Met Asn Ile Ala Glu His Tyr Met Ala Ser Asp
                645                 650                 655

Val Glu Trp Asp Pro Thr Gly Arg Tyr Val Val Thr Ser Val Ser Trp
            660                 665                 670

Trp Ser His Lys Val Asp Asn Ala Tyr Trp Leu Trp Thr Phe Gln Gly
        675                 680                 685

Arg Leu Leu Gln Lys Asn Asn Lys Asp Arg Phe Cys Gln Leu Leu Trp
690                 695                 700
```

-continued

```
Arg Pro Arg Pro Pro Thr Leu Leu Ser Gln Glu Gln Ile Lys Gln Ile
705                 710                 715                 720

Lys Lys Asp Leu Lys Lys Tyr Ser Lys Ile Phe Glu Gln Lys Asp Arg
            725                 730                 735

Leu Ser Gln Ser Lys Ala Ser Lys Glu Leu Val Glu Arg Arg Arg Thr
            740                 745                 750

Met Met Glu Asp Phe Arg Lys Tyr Arg Lys Met Ala Gln Glu Leu Tyr
            755                 760                 765

Met Glu Gln Lys Asn Glu Arg Leu Glu Leu Arg Gly Gly Val Asp Thr
        770                 775                 780

Asp Glu Leu Asp Ser Asn Val Asp Asp Trp Glu Glu Glu Thr Ile Glu
785                 790                 795                 800

Phe Phe Val Thr Glu Ile Ile Pro Leu Gly Ile Arg Ser Asp Leu
                805                 810                 815

Glu His Cys Ala Gln Pro Cys Val Leu Trp Ser Arg Gly Arg Pro Ala
            820                 825                 830

Gly Ser Arg Val Thr Pro Ala Ser Ser Leu Cys Ser Leu Ala Leu Asp
            835                 840                 845

Cys Asp Cys Ala Trp Ile Leu Pro Leu Arg His Ile Phe Val Pro Phe
850                 855                 860

Ser Pro Trp Cys Leu Gln Trp Gly Ile
865                 870

<210> SEQ ID NO 3
<211> LENGTH: 3820
<212> TYPE: DNA
<213> ORGANISM: Homo sapiens
<220> FEATURE:
<221> NAME/KEY: CDS
<222> LOCATION: (307)..(3030)

<400> SEQUENCE: 3
cagcagtgag tcggagctct atggaggtgg cagcgggtac cgagtggcgg ctgcagcagc      60
gactcctctg agctgagttt gaggccgtcc ccgactcctt cctccccctt ccctcccccc     120 ttttttttgtt ttccgttccc ctttcccctc ccttccctat ccccgacgac cggatcctga    180
ggaggcagct gcggtggcag ctgctgagtt ctcggtgaag gtatttcatt tctcctgtcc    240
cctcccctcc ccaccccatc tattaatatt attcttttga agattcttcg ttgtcaagcc    300 gccaaa gtg gag agt gcg att gca gaa ggg ggt gct tct cgt ttc agt        348
       Val Glu Ser Ala Ile Ala Glu Gly Gly Ala Ser Arg Phe Ser
         1               5                  10 gct tct tcg ggc gga gga gga agt agg ggt gca cct cag cac tat ccc       396
Ala Ser Ser Gly Gly Gly Gly Ser Arg Gly Ala Pro Gln His Tyr Pro
 15                  20                  25                  30 aag act gct ggc aac agc gag ttc ctg ggg aaa acc cca ggg caa aac      444
Lys Thr Ala Gly Asn Ser Glu Phe Leu Gly Lys Thr Pro Gly Gln Asn
                35                  40                  45 gct cag aaa tgg att cct gca cga agc act aga cga gat gac aac tcc      492
Ala Gln Lys Trp Ile Pro Ala Arg Ser Thr Arg Arg Asp Asp Asn Ser
            50                  55                  60 gca gca aac aac tcc gca aac gaa aaa gaa cga cat gat gca atc ttc      540
Ala Ala Asn Asn Ser Ala Asn Glu Lys Glu Arg His Asp Ala Ile Phe
        65                  70                  75 agg aaa gta aga ggc ata cta aat aag ctt act cct gaa aag ttt gac      588
Arg Lys Val Arg Gly Ile Leu Asn Lys Leu Thr Pro Glu Lys Phe Asp
    80                  85                  90
```

```
aag cta tgc ctt gag ctc ctc aat gtg ggt gta gag tct aaa ctc atc      636
Lys Leu Cys Leu Glu Leu Leu Asn Val Gly Val Glu Ser Lys Leu Ile
 95                 100                 105                 110 ctt aaa ggg gtc ata ctg ctg att gtg gac aaa gcc cta gaa gag cca      684
Leu Lys Gly Val Ile Leu Leu Ile Val Asp Lys Ala Leu Glu Glu Pro
                    115                 120                 125 aag tat agc tca ctg tat gct cag cta tgt ctg cga ttg gca gaa gat      732
Lys Tyr Ser Ser Leu Tyr Ala Gln Leu Cys Leu Arg Leu Ala Glu Asp
                130                 135                 140 gca cca aac ttt gat ggc cca gca gca gag ggt caa cca gga cag aag      780
Ala Pro Asn Phe Asp Gly Pro Ala Ala Glu Gly Gln Pro Gly Gln Lys
            145                 150                 155 caa agc acc aca ttc aga cgc ctc cta att tcc aaa tta caa gat gaa      828
Gln Ser Thr Thr Phe Arg Arg Leu Leu Ile Ser Lys Leu Gln Asp Glu
        160                 165                 170 ttt gaa aac cga act aga aat gtt gat gtc tat gat aag cgt gaa aat      876
Phe Glu Asn Arg Thr Arg Asn Val Asp Val Tyr Asp Lys Arg Glu Asn
175                 180                 185                 190 ccc ctc ctc ccc gag gag gag gaa cag aga gcc att gct aag atc aag      924
Pro Leu Leu Pro Glu Glu Glu Glu Gln Arg Ala Ile Ala Lys Ile Lys
                    195                 200                 205 atg ttg gga aac atc aaa ttc att gga gag ctt ggc aag ctt gat ctt      972
Met Leu Gly Asn Ile Lys Phe Ile Gly Glu Leu Gly Lys Leu Asp Leu
                210                 215                 220 att cac gaa tct atc ctt cat aag tgc atc aaa aca ctt ttg gaa aag     1020
Ile His Glu Ser Ile Leu His Lys Cys Ile Lys Thr Leu Leu Glu Lys
            225                 230                 235 aag aag aga gtc caa ctc aaa gat atg gga gag gat ttg gag tgc ctc     1068
Lys Lys Arg Val Gln Leu Lys Asp Met Gly Glu Asp Leu Glu Cys Leu
        240                 245                 250 tgt cag ata atg agg aca gtg gga cct aga tta gac cat gaa cga gcc     1116
Cys Gln Ile Met Arg Thr Val Gly Pro Arg Leu Asp His Glu Arg Ala
255                 260                 265                 270 aag tcc tta atg gat cag tac ttt gcc cga atg tgc tcc ttg atg tta     1164
Lys Ser Leu Met Asp Gln Tyr Phe Ala Arg Met Cys Ser Leu Met Leu
                    275                 280                 285 agt aag gaa ttg cca gca agg att cgt ttc ctg ctg cag gat acc gta     1212
Ser Lys Glu Leu Pro Ala Arg Ile Arg Phe Leu Leu Gln Asp Thr Val
                290                 295                 300 gag ttg cga gaa cac cat tgg gtt cct cgc aag gct ttt ctt gac aat     1260
Glu Leu Arg Glu His His Trp Val Pro Arg Lys Ala Phe Leu Asp Asn
            305                 310                 315 gga cca aag acg atc aat caa att cgt caa gat gca gta aaa gat cta     1308
Gly Pro Lys Thr Ile Asn Gln Ile Arg Gln Asp Ala Val Lys Asp Leu
        320                 325                 330 ggg gtg ttt att cct gct cct atg gct caa ggg atg aga agt gac ttc     1356
Gly Val Phe Ile Pro Ala Pro Met Ala Gln Gly Met Arg Ser Asp Phe
335                 340                 345                 350 ttt ctg gag gga ccg ttc atg cca ccc agg atg aaa atg gat agg gac     1404
Phe Leu Glu Gly Pro Phe Met Pro Pro Arg Met Lys Met Asp Arg Asp
                    355                 360                 365 cca ctt gga gga ctt gct gat atg ttt gga caa atg cca ggt agc gga     1452
Pro Leu Gly Gly Leu Ala Asp Met Phe Gly Gln Met Pro Gly Ser Gly
                370                 375                 380 att ggt act ggt cca gga gtt atc cag gat aga ttt tca ccc acc atg     1500
Ile Gly Thr Gly Pro Gly Val Ile Gln Asp Arg Phe Ser Pro Thr Met
            385                 390                 395 gga cgt cat cgt tca aat caa ctc ttc aat ggc cat ggg gga cac atc     1548
Gly Arg His Arg Ser Asn Gln Leu Phe Asn Gly His Gly Gly His Ile
        400                 405                 410
```

```
                                                              -continued atg cct ccc aca caa tcg cag ttt gga gag atg gga ggc aag ttt atg           1596
Met Pro Pro Thr Gln Ser Gln Phe Gly Glu Met Gly Gly Lys Phe Met
415                 420                 425                 430 aaa agc cag ggg cta agc cag ctc tac cat aac cag agt cag gga ctc           1644
Lys Ser Gln Gly Leu Ser Gln Leu Tyr His Asn Gln Ser Gln Gly Leu
                435                 440                 445 tta tcc cag ctg caa gga cag tcg aag gat atg cca cct cgg ttt tct           1692
Leu Ser Gln Leu Gln Gly Gln Ser Lys Asp Met Pro Pro Arg Phe Ser
        450                 455                 460 aag aaa gga cag ctt aat gca gat gag att agc ctg agg cct gct cag           1740
Lys Lys Gly Gln Leu Asn Ala Asp Glu Ile Ser Leu Arg Pro Ala Gln
465                 470                 475 tcg ttc cta atg aat aaa aat caa gtg cca aag ctt cag ccc cag ata           1788
Ser Phe Leu Met Asn Lys Asn Gln Val Pro Lys Leu Gln Pro Gln Ile
            480                 485                 490 act atg att cct cct agt gca caa cca cca cgc act caa aca cca cct           1836
Thr Met Ile Pro Pro Ser Ala Gln Pro Pro Arg Thr Gln Thr Pro Pro
495                 500                 505                 510 ctg gga cag aca cct cag ctt ggt ctc aaa act aat cca cca ctt atc           1884
Leu Gly Gln Thr Pro Gln Leu Gly Leu Lys Thr Asn Pro Pro Leu Ile
                515                 520                 525 cag gaa aag cct gcc aag acc agc aaa aag cca cca ccg tca aag gaa           1932
Gln Glu Lys Pro Ala Lys Thr Ser Lys Lys Pro Pro Pro Ser Lys Glu
        530                 535                 540 gaa ctc ctt aaa cta act gaa act gtt gtg act gaa tat cta aat agt           1980
Glu Leu Leu Lys Leu Thr Glu Thr Val Val Thr Glu Tyr Leu Asn Ser
545                 550                 555 gga aat gca aat gag gct gtc aat ggt gta aga gaa atg agg gct cct           2028
Gly Asn Ala Asn Glu Ala Val Asn Gly Val Arg Glu Met Arg Ala Pro
            560                 565                 570 aaa cac ttt ctt cct gag atg tta agc aaa gta atc atc ctg tca cta           2076
Lys His Phe Leu Pro Glu Met Leu Ser Lys Val Ile Ile Leu Ser Leu
575                 580                 585                 590 gat aga agc gat gaa gat aaa gaa aaa gca agt tct ttg atc agt tta           2124
Asp Arg Ser Asp Glu Asp Lys Glu Lys Ala Ser Ser Leu Ile Ser Leu
                595                 600                 605 ctc aaa cag gaa ggg ata gcc aca agt gac aac ttc atg cag gct ttc           2172
Leu Lys Gln Glu Gly Ile Ala Thr Ser Asp Asn Phe Met Gln Ala Phe
        610                 615                 620 ctg aat gta ttg gac cag tgt ccc aaa ctg gag gtt gac atc cct ttg           2220
Leu Asn Val Leu Asp Gln Cys Pro Lys Leu Glu Val Asp Ile Pro Leu
625                 630                 635 gtg aaa tcc tat tta gca cag ttt gca gct cgt gcc atc att tca gag           2268
Val Lys Ser Tyr Leu Ala Gln Phe Ala Ala Arg Ala Ile Ile Ser Glu
            640                 645                 650 ctg gtg agc att tca gaa cta gct caa cca cta gaa agt ggc acc cat           2316
Leu Val Ser Ile Ser Glu Leu Ala Gln Pro Leu Glu Ser Gly Thr His
655                 660                 665                 670 ttt cct ctc ttc cta ctt tgt ctt cag cag tta gct aaa tta caa gat           2364
Phe Pro Leu Phe Leu Leu Cys Leu Gln Gln Leu Ala Lys Leu Gln Asp
                675                 680                 685 cga gaa tgg tta aca gaa ctt ttt caa caa agc aag gtc aat atg cag           2412
Arg Glu Trp Leu Thr Glu Leu Phe Gln Gln Ser Lys Val Asn Met Gln
        690                 695                 700 aaa atg ctc cca gaa att gat cag aat aag gac cgc atg ttg gag att           2460
Lys Met Leu Pro Glu Ile Asp Gln Asn Lys Asp Arg Met Leu Glu Ile
705                 710                 715 ttg gaa gga aag gga ctg agt ttc tta ttc cca ctc ctc aaa ttg gag           2508
Leu Glu Gly Lys Gly Leu Ser Phe Leu Phe Pro Leu Leu Lys Leu Glu
            720                 725                 730
```

-continued

```
aag gaa ctg ttg aag caa ata aag ttg gat cca tcc cct caa acc ata       2556
Lys Glu Leu Leu Lys Gln Ile Lys Leu Asp Pro Ser Pro Gln Thr Ile
735                 740                 745                 750 tat aaa tgg att aaa gat aac atc tct ccc aaa ctt cat gta gat aaa       2604
Tyr Lys Trp Ile Lys Asp Asn Ile Ser Pro Lys Leu His Val Asp Lys
                755                 760                 765 gga ttt gtg aac atc tta atg act agc ttc tta cag tac att tct agt       2652
Gly Phe Val Asn Ile Leu Met Thr Ser Phe Leu Gln Tyr Ile Ser Ser
            770                 775                 780 gaa gta aac ccc ccc agc gat gaa aca gat tca tcc tct gct cct tcc       2700
Glu Val Asn Pro Pro Ser Asp Glu Thr Asp Ser Ser Ser Ala Pro Ser
        785                 790                 795 aaa gaa cag tta gag cag gaa aaa caa cta cta cta tct ttc aag cca       2748
Lys Glu Gln Leu Glu Gln Glu Lys Gln Leu Leu Leu Ser Phe Lys Pro
800                 805                 810 gta atg cag aaa ttt ctt cat gat cac gtt gat cta caa gtc agt gcc       2796
Val Met Gln Lys Phe Leu His Asp His Val Asp Leu Gln Val Ser Ala
815                 820                 825                 830 ctg tat gct ctc cag gtg cac tgc tat aac agc aac ttc cca aaa ggc       2844
Leu Tyr Ala Leu Gln Val His Cys Tyr Asn Ser Asn Phe Pro Lys Gly
                835                 840                 845 atg tta ctt cgc ttt ttt gtg cac ttc tat gac atg gaa att att gaa       2892
Met Leu Leu Arg Phe Phe Val His Phe Tyr Asp Met Glu Ile Ile Glu
            850                 855                 860 gaa gaa gct ttc ttg gct tgg aaa gaa gat ata acc caa gag ttt ccg       2940
Glu Glu Ala Phe Leu Ala Trp Lys Glu Asp Ile Thr Gln Glu Phe Pro
        865                 870                 875 gga aaa ggc aag gct ttg ttc cag gtg aat cag tgg cta acc tgg tta       2988
Gly Lys Gly Lys Ala Leu Phe Gln Val Asn Gln Trp Leu Thr Trp Leu
880                 885                 890 gaa act gct gaa gaa gaa gaa tca gag gaa gaa gct gac taa              3030
Glu Thr Ala Glu Glu Glu Glu Ser Glu Glu Glu Ala Asp
895                 900                 905 agaaccagcc aaagccttaa attgtgcaaa acatactgtt gctatgatgt aactgcattt    3090
gacctaacca ctgcgaaaat tcattccgct gtaatgtttt cacaatattt aaagcagaag    3150
cacgtcagtt aggatttcct tctgcataag gttttttgt agtgtaatgt cttaatcata     3210
gtctaccatc aaatatttta ggagtatctt taatgtttag atagtatatt agcagcatgc    3270
aataattaca tcataagttc tcaagcagag gcagtctatt gcaaggacct tctttgctgc    3330
cagttatcat aggctgtttt aagttagaaa actgaatagc aacactgaat actgtagaaa    3390
tgcactttgc tcagtaatac ttgagttgtt gcaatatttg attatccatt tggttgttac    3450
agaaaaattc ttaactgtaa ttgatggttg ttgccgtaat agtatattgc ctgtatttct    3510
acctctagta atgggcttta tgtgctagat tttaatatcc ttgagcctgg gcaagtgcac    3570
aagtcttttt aaaagaaaca tggtttactt gcacaaaact gatcagtttt gagagatcgt    3630
taatgccctt gaagtggttt tgtgggtgt gaaacaaatg gtgagaattt gaattggtcc     3690
ctcctattat agtattgaaa ttaagtctac ttaatttatc aagtcatgtt catgccctga    3750
ttttatatac ttgtatctat caataaacat tgtgatactt gaaaaaaaaa aaaaaaaaa     3810 aaaaaaaaa                                                             3820
```

<210> SEQ ID NO 4
<211> LENGTH: 907
<212> TYPE: PRT
<213> ORGANISM: Homo sapiens -continued

```
<400> SEQUENCE: 4

Val Glu Ser Ala Ile Ala Glu Gly Gly Ala Ser Arg Phe Ser Ala Ser
 1               5                  10                  15

Ser Gly Gly Gly Gly Ser Arg Gly Ala Pro Gln His Tyr Pro Lys Thr
             20                  25                  30

Ala Gly Asn Ser Glu Phe Leu Gly Lys Thr Pro Gly Gln Asn Ala Gln
         35                  40                  45

Lys Trp Ile Pro Ala Arg Ser Thr Arg Arg Asp Asp Asn Ser Ala Ala
     50                  55                  60

Asn Asn Ser Ala Asn Glu Lys Glu Arg His Asp Ala Ile Phe Arg Lys
 65                  70                  75                  80

Val Arg Gly Ile Leu Asn Lys Leu Thr Pro Glu Lys Phe Asp Lys Leu
                 85                  90                  95

Cys Leu Glu Leu Leu Asn Val Gly Val Glu Ser Lys Leu Ile Leu Lys
            100                 105                 110

Gly Val Ile Leu Leu Ile Val Asp Lys Ala Leu Glu Glu Pro Lys Tyr
        115                 120                 125

Ser Ser Leu Tyr Ala Gln Leu Cys Leu Arg Leu Ala Glu Asp Ala Pro
    130                 135                 140

Asn Phe Asp Gly Pro Ala Ala Glu Gly Gln Pro Gly Gln Lys Gln Ser
145                 150                 155                 160

Thr Thr Phe Arg Arg Leu Leu Ile Ser Lys Leu Gln Asp Glu Phe Glu
                165                 170                 175

Asn Arg Thr Arg Asn Val Asp Val Tyr Asp Lys Arg Glu Asn Pro Leu
            180                 185                 190

Leu Pro Glu Glu Glu Gln Arg Ala Ile Ala Lys Ile Lys Met Leu
        195                 200                 205

Gly Asn Ile Lys Phe Ile Gly Glu Leu Gly Lys Leu Asp Leu Ile His
    210                 215                 220

Glu Ser Ile Leu His Lys Cys Ile Lys Thr Leu Leu Glu Lys Lys Lys
225                 230                 235                 240

Arg Val Gln Leu Lys Asp Met Gly Glu Asp Leu Glu Cys Leu Cys Gln
                245                 250                 255

Ile Met Arg Thr Val Gly Pro Arg Leu Asp His Glu Arg Ala Lys Ser
            260                 265                 270

Leu Met Asp Gln Tyr Phe Ala Arg Met Cys Ser Leu Met Leu Ser Lys
        275                 280                 285

Glu Leu Pro Ala Arg Ile Arg Phe Leu Leu Gln Asp Thr Val Glu Leu
    290                 295                 300

Arg Glu His His Trp Val Pro Arg Lys Ala Phe Leu Asp Asn Gly Pro
305                 310                 315                 320

Lys Thr Ile Asn Gln Ile Arg Gln Asp Ala Val Lys Asp Leu Gly Val
                325                 330                 335

Phe Ile Pro Ala Pro Met Ala Gln Gly Met Arg Ser Asp Phe Phe Leu
            340                 345                 350

Glu Gly Pro Phe Met Pro Pro Arg Met Lys Met Asp Arg Asp Pro Leu
        355                 360                 365

Gly Gly Leu Ala Asp Met Phe Gly Gln Met Pro Gly Ser Gly Ile Gly
    370                 375                 380

Thr Gly Pro Gly Val Ile Gln Asp Arg Phe Ser Pro Thr Met Gly Arg
385                 390                 395                 400

His Arg Ser Asn Gln Leu Phe Asn Gly His Gly Gly His Ile Met Pro
                405                 410                 415
```

-continued

```
Pro Thr Gln Ser Gln Phe Gly Glu Met Gly Gly Lys Phe Met Lys Ser
            420                 425                 430

Gln Gly Leu Ser Gln Leu Tyr His Asn Gln Ser Gln Gly Leu Leu Ser
        435                 440                 445

Gln Leu Gln Gly Gln Ser Lys Asp Met Pro Pro Arg Phe Ser Lys Lys
450                 455                 460

Gly Gln Leu Asn Ala Asp Glu Ile Ser Leu Arg Pro Ala Gln Ser Phe
465                 470                 475                 480

Leu Met Asn Lys Asn Gln Val Pro Lys Leu Gln Pro Gln Ile Thr Met
                485                 490                 495

Ile Pro Pro Ser Ala Gln Pro Arg Thr Gln Thr Pro Pro Leu Gly
                500                 505                 510

Gln Thr Pro Gln Leu Gly Leu Lys Thr Asn Pro Pro Leu Ile Gln Glu
            515                 520                 525

Lys Pro Ala Lys Thr Ser Lys Lys Pro Pro Ser Lys Glu Glu Leu
            530                 535                 540

Leu Lys Leu Thr Glu Thr Val Val Thr Glu Tyr Leu Asn Ser Gly Asn
545                 550                 555                 560

Ala Asn Glu Ala Val Asn Gly Val Arg Glu Met Arg Ala Pro Lys His
                565                 570                 575

Phe Leu Pro Glu Met Leu Ser Lys Val Ile Ile Leu Ser Leu Asp Arg
            580                 585                 590

Ser Asp Glu Asp Lys Glu Lys Ala Ser Ser Leu Ile Ser Leu Leu Lys
        595                 600                 605

Gln Glu Gly Ile Ala Thr Ser Asp Asn Phe Met Gln Ala Phe Leu Asn
        610                 615                 620

Val Leu Asp Gln Cys Pro Lys Leu Glu Val Asp Ile Pro Leu Val Lys
625                 630                 635                 640

Ser Tyr Leu Ala Gln Phe Ala Ala Arg Ala Ile Ile Ser Glu Leu Val
                645                 650                 655

Ser Ile Ser Glu Leu Ala Gln Pro Leu Glu Ser Gly Thr His Phe Pro
                660                 665                 670

Leu Phe Leu Leu Cys Leu Gln Leu Ala Lys Leu Gln Asp Arg Glu
            675                 680                 685

Trp Leu Thr Glu Leu Phe Gln Gln Ser Lys Val Asn Met Gln Lys Met
690                 695                 700

Leu Pro Glu Ile Asp Gln Asn Lys Asp Arg Met Leu Glu Ile Leu Glu
705                 710                 715                 720

Gly Lys Gly Leu Ser Phe Leu Phe Pro Leu Leu Lys Leu Glu Lys Glu
                725                 730                 735

Leu Leu Lys Gln Ile Lys Leu Asp Pro Ser Pro Gln Thr Ile Tyr Lys
            740                 745                 750

Trp Ile Lys Asp Asn Ile Ser Pro Lys Leu His Val Asp Lys Gly Phe
            755                 760                 765

Val Asn Ile Leu Met Thr Ser Phe Leu Gln Tyr Ile Ser Ser Glu Val
        770                 775                 780

Asn Pro Pro Ser Asp Glu Thr Asp Ser Ser Ser Ala Pro Ser Lys Glu
785                 790                 795                 800

Gln Leu Glu Gln Glu Lys Gln Leu Leu Leu Ser Phe Lys Pro Val Met
                805                 810                 815

Gln Lys Phe Leu His Asp His Val Asp Leu Gln Val Ser Ala Leu Tyr
            820                 825                 830
```

```
Ala Leu Gln Val His Cys Tyr Asn Ser Asn Phe Pro Lys Gly Met Leu
        835                 840                 845

Leu Arg Phe Phe Val His Phe Tyr Asp Met Glu Ile Ile Glu Glu Glu
        850                 855                 860

Ala Phe Leu Ala Trp Lys Glu Asp Ile Thr Gln Glu Phe Pro Gly Lys
865                 870                 875                 880

Gly Lys Ala Leu Phe Gln Val Asn Gln Trp Leu Thr Trp Leu Glu Thr
                885                 890                 895

Ala Glu Glu Glu Ser Glu Glu Glu Ala Asp
            900                 905

<210> SEQ ID NO 5
<211> LENGTH: 33
<212> TYPE: DNA
<213> ORGANISM: Homo sapiens

<400> SEQUENCE: 5
accggaattc aaaatggacg cggacgagcc ctc                         33

<210> SEQ ID NO 6
<211> LENGTH: 28
<212> TYPE: DNA
<213> ORGANISM: Homo sapiens

<400> SEQUENCE: 6
agcggaattc ttaaatcccc cactgcag                              28

<210> SEQ ID NO 7
<211> LENGTH: 42
<212> TYPE: DNA
<213> ORGANISM: Homo sapiens

<400> SEQUENCE: 7
gacttctaga ccgccatcat gcaggacgcg gagaacgtgg cg              42

<210> SEQ ID NO 8
<211> LENGTH: 31
<212> TYPE: DNA
<213> ORGANISM: Homo sapiens

<400> SEQUENCE: 8
gacttctaga ggcgcaggag aaggtgccgc c                          31

<210> SEQ ID NO 9
<211> LENGTH: 40
<212> TYPE: DNA
<213> ORGANISM: Homo sapiens

<400> SEQUENCE: 9
gactggtacc gccatcatgg agagtgcgat tgcagaaggg                 40

<210> SEQ ID NO 10
<211> LENGTH: 31
<212> TYPE: DNA
<213> ORGANISM: Homo sapiens

<400> SEQUENCE: 10
gactggtacc cgcagtggtt aggtcaaatg c                          31

<210> SEQ ID NO 11
<211> LENGTH: 58
<212> TYPE: DNA
```

-continued

```
<213> ORGANISM: Homo sapiens

<400> SEQUENCE: 11
gactctagat taagcgtagt ctgggacgtc gtatgggtaa atccccact gcagacac        58

<210> SEQ ID NO 12
<211> LENGTH: 57
<212> TYPE: DNA
<213> ORGANISM: Homo sapiens

<400> SEQUENCE: 12
gacggtacct taagcgtagt ctgggacgtc gtatgggtag tcagcttctt cctctga         57

<210> SEQ ID NO 13
<211> LENGTH: 10
<212> TYPE: PRT
<213> ORGANISM: Homo sapiens

<400> SEQUENCE: 13

Tyr Pro Tyr Asp Val Pro Asp Tyr Ala Gly
  1               5                  10
```